United States Patent
Kashyap et al.

(10) Patent No.: US 10,106,582 B2
(45) Date of Patent: Oct. 23, 2018

(54) COMPLEX-FORMATION-MODULATING AGENTS AND USES THEREFOR

(71) Applicant: Factor Therapeutics Limited, Darra (AU)

(72) Inventors: Abhishek Kashyap, Lutwyche (AU); Gary Keith Shooter, East Ipswich (AU); David Leavesley, Kenmore Hills (AU); Brett Hollier, Holland Park (AU); Adrian Charles Herington, Clayfield (AU); Zee Upton, Kenmore Hills (AU)

(73) Assignee: FACTOR THERAPEUTICS LIMITED, Darra (AU)

( * ) Notice: Subject to any disclaimer, the term of this patent is extended or adjusted under 35 U.S.C. 154(b) by 0 days.

(21) Appl. No.: 14/646,860

(22) PCT Filed: Nov. 21, 2013

(86) PCT No.: PCT/AU2013/001342
§ 371 (c)(1),
(2) Date: May 22, 2015

(87) PCT Pub. No.: WO2014/078896
PCT Pub. Date: May 30, 2014

(65) Prior Publication Data
US 2015/0299263 A1    Oct. 22, 2015

(30) Foreign Application Priority Data
Nov. 22, 2012    (AU) .................... 2012905085

(51) Int. Cl.
| A61K 38/00 | (2006.01) |
|---|---|
| C07K 9/00 | (2006.01) |
| C07K 14/72 | (2006.01) |
| A61K 38/14 | (2006.01) |
| A61K 45/06 | (2006.01) |

(52) U.S. Cl.
CPC .............. *C07K 9/00* (2013.01); *A61K 38/14* (2013.01); *A61K 45/06* (2013.01); *C07K 14/72* (2013.01); *A61K 38/00* (2013.01)

(58) Field of Classification Search
None
See application file for complete search history.

(56) References Cited

U.S. PATENT DOCUMENTS

| 7,514,398 B2 * | 4/2009 | Upton ................ A61K 38/1709 424/423 |
| 2009/0081685 A1 * | 3/2009 | Beyer ................ C12Q 1/6886 435/6.14 |
| 2010/0144038 A1 | 6/2010 | Miyake et al. |
| 2010/0303884 A1 | 12/2010 | Upton et al. |
| 2011/0183924 A1 | 7/2011 | Mintz et al. |

FOREIGN PATENT DOCUMENTS

| JP | 2003-216190 | 7/2003 |
| WO | WO 2006/072563 | 7/2006 |
| WO | WO 2006/116867 | 11/2006 |
| WO | WO 2007/110230 | 10/2007 |
| WO | WO 2011/112397 | 9/2011 |

OTHER PUBLICATIONS

Kashyap et al (Endocrinology 152: 1388-1401, 2011).*
NCBI Reference Sequence: NP_000629.3, downloaded on Oct. 12, 2016.*
Wang et al (Cell Death and Disease (2015) 6, e1796).*
NCBI Reference Sequence: NP_596867.1, downloaded on Oct. 12, 2016.*
Mol Cancer Ther; 15(7) Jul. 2016.*
GenBank Accession No. AC002094, Sep. 9, 1997, 39 pages.
GenBank Accession No. AFQ00545, Aug. 25, 2012, 1 page.
Haluska et al., In vitro and in vivo antitumor effects of the dual insulin-like growth factor-I/insulin receptor inhibitor, BMS-554417. Cancer Res. Jan. 1, 2006;66(1):362-71.
Sachdev et al., A chimeric humanized single-chain antibody against the type I insulin-like growth factor (IGF) receptor renders breast cancer cells refractory to the mitogenic effects of IGF-I. Cancer Res. Feb. 1, 2003;63(3):627-35.
Uniprot Accession No. H0YJW9, Feb. 22, 2012, 3 pages.
International Preliminary Report on Patentability for PCT/AU2013/01342, dated Mar. 20, 2015, 15 pages.
International Search Report and Written Opinion for PCT/AU2013/01342, dated Feb. 27, 2014, 14 pages.

* cited by examiner

*Primary Examiner* — James H Alstrum-Acevedo
*Assistant Examiner* — Sergio Coffa
(74) *Attorney, Agent, or Firm* — Casimir Jones, S.C.; Mary Ann D. Brow

(57) ABSTRACT

Disclosed are methods and agents for modulating proliferation, migration and/or survival of cells. More particularly, the present invention discloses molecules that have any one or more activities selected from: inhibiting binding of vitronectin to at least one vitronectin-binding partner selected from an IGF and IGFBP, inhibiting formation of a complex comprising vitronectin and at least one vitronectin-binding partner selected from an IGF and IGFBP, or inhibiting proliferation or survival of a hyperproliferative cell (e.g., a neoplastic cell or non-neoplastic cell), or inhibiting migration or invasion of a hyperproliferative cell (e.g., a neoplastic cell or a non-neoplastic cell). Additionally, the present invention discloses the use of these molecules in methods and compositions for treating or preventing hyperproliferative cell disorders including neoplastic (e.g., cancers such as epithelial cancers) and non-neoplastic disorders.

9 Claims, 6 Drawing Sheets
Specification includes a Sequence Listing.

A

```
              . . . . . . . . . 10 . . . . . . . . .
Human         [                              ] T       A
Mouse                                           A       E
Rabbit                                          A       A
Bovine                                          A       A
Goat                                            A       A
Pig                                             T       A
Rat                                             V       E
Consistency                                     6       6
```

B

```
              . . . . . . . . .
Human         [            ] R P
Pig                          V P
Bovine                       T S
Goat                         T S
Mouse                        T P
Rat                          T S
Rabbit                       T S
Consistency                  6 6
```

C

```
              . . . . . . . . . 10 . . . . . . . .
Human
Pig
Rat
Bovine
Goat
Rabbit
Mouse
Consistency
```

D

```
              .........10.........
Human        K Q
Mouse        K Q
Rat          K Q
Pig          K Q
Bovine       N H
Goat         N H
Rabbit       D K
Consistency  6 6
```

E

```
              .........10..........20.....
Human        E                   E
Bovine       K                   R
Goat         K                   R
Mouse        E                   E
Rabbit       E                   K
Rat          E                   E
Pig          A                   R
Consistency  6                   6
```

F

```
              .........10.........20..
Human                  Q   F
Rabbit                 Q   F
Rat                    G   F
Mouse                  E   F
Bovine                 Q   L
Goat                   Q   L
Pig                    E   V
Consistency            6   6
```

| | ..........10..........20.. |
|---|---|
| Human | Y |
| Pig | Y |
| Rabbit | Y |
| Bovine | Y |
| Goat | Y |
| Mouse | N |
| Rat | - |
| Consistency | 6 |

H

| | ..........10.......... |
|---|---|
| Human | T |
| Bovine | A |
| Goat | S |
| Mouse | S |
| Rabbit | T |
| Rat | S |
| Pig | T |
| Consistency | 6 |

FIGURE 1 cont'd

SEQUENCE LISTING

<160> NUMBER OF SEQ ID NOS: 128

<210> SEQ ID NO 1
<211> LENGTH: 57
<212> TYPE: DNA
<213> ORGANISM: Homo sapiens

<400> SEQUENCE: 1
tgccagtgcg acgagctgtg cagctactac cagagctgct gcaccgacta caccgcc        57

<210> SEQ ID NO 2
<211> LENGTH: 19
<212> TYPE: PRT
<213> ORGANISM: Homo sapiens

<400> SEQUENCE: 2

Cys Gln Cys Asp Glu Leu Cys Ser Tyr Tyr Gln Ser Cys Cys Thr Asp
1               5                   10                  15

Tyr Thr Ala

<210> SEQ ID NO 3
<211> LENGTH: 57
<212> TYPE: DNA
<213> ORGANISM: Sus scrofa

<400> SEQUENCE: 3
tgccagtgcg acgagctgtg cagctactac cagagctgct gcaccgacta cgtggcc        57

<210> SEQ ID NO 4
<211> LENGTH: 19
<212> TYPE: PRT
<213> ORGANISM: Sus scrofa

<400> SEQUENCE: 4

Cys Gln Cys Asp Glu Leu Cys Ser Tyr Tyr Gln Ser Cys Cys Thr Asp
1               5                   10                  15

Tyr Val Ala

<210> SEQ ID NO 5
<211> LENGTH: 57
<212> TYPE: DNA
<213> ORGANISM: Bos taurus

<400> SEQUENCE: 5
tgccagtgcg acgagctgtg cagctactac cagagctgct gcgccgactt catggcc         57

<210> SEQ ID NO 6
<211> LENGTH: 19
<212> TYPE: PRT
<213> ORGANISM: Bos taurus

<400> SEQUENCE: 6

Cys Gln Cys Asp Glu Leu Cys Ser Tyr Tyr Gln Ser Cys Cys Ala Asp
1               5                   10                  15

Phe Met Ala

<210> SEQ ID NO 7
<211> LENGTH: 57
<212> TYPE: DNA
<213> ORGANISM: Capra hircus

<400> SEQUENCE: 7
tgccagtgcg acgagctgtg cagctactac cagagctgct gcgccgactt catggcc         57

<210> SEQ ID NO 8
<211> LENGTH: 19
<212> TYPE: PRT
<213> ORGANISM: Capra hircus

<400> SEQUENCE: 8

Cys Gln Cys Asp Glu Leu Cys Ser Tyr Tyr Gln Ser Cys Cys Ala Asp
1               5                   10                  15

Phe Met Ala

<210> SEQ ID NO 9
<211> LENGTH: 57
<212> TYPE: DNA
<213> ORGANISM: Mus musculus

<400> SEQUENCE: 9
tgccagtgcg acgagctgtg cacctactac cagagctgct gcgccgacta catggag         57

<210> SEQ ID NO 10
<211> LENGTH: 19
<212> TYPE: PRT
<213> ORGANISM: Mus musculus

<400> SEQUENCE: 10

Cys Gln Cys Asp Glu Leu Cys Thr Tyr Tyr Gln Ser Cys Cys Ala Asp
1               5                   10                  15

Tyr Met Glu

<210> SEQ ID NO 11
<211> LENGTH: 57
<212> TYPE: DNA
<213> ORGANISM: Oryctolagus cuniculus

<400> SEQUENCE: 11
tgccagtgcg acgagctgtg ctcctactac cagtcctgct gcgccgacta cgccgcc    57

<210> SEQ ID NO 12
<211> LENGTH: 19
<212> TYPE: PRT
<213> ORGANISM: Oryctolagus cuniculus

<400> SEQUENCE: 12

Cys Gln Cys Asp Glu Leu Cys Ser Tyr Tyr Gln Ser Cys Cys Ala Asp
1               5                   10                  15

Tyr Ala Ala

<210> SEQ ID NO 13
<211> LENGTH: 57
<212> TYPE: DNA
<213> ORGANISM: Rattus rattus

<400> SEQUENCE: 13
tgccagtgcg acgagctgtg cacctactac cagagctgct gcgtggacta catggag    57

<210> SEQ ID NO 14
<211> LENGTH: 19
<212> TYPE: PRT
<213> ORGANISM: Rattus rattus

<400> SEQUENCE: 14

Cys Gln Cys Asp Glu Leu Cys Thr Tyr Tyr Gln Ser Cys Cys Val Asp
1               5                   10                  15

Tyr Met Glu

<210> SEQ ID NO 15
<211> LENGTH: 24
<212> TYPE: DNA
<213> ORGANISM: Homo sapiens

<400> SEQUENCE: 15
accctgcacc ccggcaggcc ccag    24

<210> SEQ ID NO 16
<211> LENGTH: 8
<212> TYPE: PRT
<213> ORGANISM: Homo sapiens

<400> SEQUENCE: 16

Thr Leu His Pro Gly Arg Pro Gln
1               5

<210> SEQ ID NO 17
<211> LENGTH: 24
<212> TYPE: DNA
<213> ORGANISM: Sus scrofa

<400> SEQUENCE: 17
accgacgacc tgggcgtgcc cgag    24

```
<210> SEQ ID NO 18
<211> LENGTH: 8
<212> TYPE: PRT
<213> ORGANISM: Sus scrofa

<400> SEQUENCE: 18

Thr Asp Asp Leu Gly Val Pro Glu
1               5

<210> SEQ ID NO 19
<211> LENGTH: 24
<212> TYPE: DNA
<213> ORGANISM: Bos taurus

<400> SEQUENCE: 19
accagcgacc tgggcaccag cgag                                          24

<210> SEQ ID NO 20
<211> LENGTH: 8
<212> TYPE: PRT
<213> ORGANISM: Bos taurus

<400> SEQUENCE: 20

Thr Ser Asp Leu Gly Thr Ser Glu
1               5

<210> SEQ ID NO 21
<211> LENGTH: 24
<212> TYPE: DNA
<213> ORGANISM: Capra hircus

<400> SEQUENCE: 21
accagcgacc tgggcaccag cgag                                          24

<210> SEQ ID NO 22
<211> LENGTH: 8
<212> TYPE: PRT
<213> ORGANISM: Capra hircus

<400> SEQUENCE: 22

Thr Ser Asp Leu Gly Thr Ser Glu
1               5

<210> SEQ ID NO 23
<211> LENGTH: 24
<212> TYPE: DNA
<213> ORGANISM: Mus musculus

<400> SEQUENCE: 23
accaccgacc agggcacccc cgag                                          24

<210> SEQ ID NO 24
<211> LENGTH: 8
<212> TYPE: PRT
<213> ORGANISM: Mus musculus

<400> SEQUENCE: 24

Thr Thr Asp Gln Gly Thr Pro Glu
1               5

<210> SEQ ID NO 25
<211> LENGTH: 24
<212> TYPE: DNA
```

<210> SEQ ID NO 25
<211> LENGTH: 24
<212> TYPE: DNA
<213> ORGANISM: Oryctolagus cuniculus

<400> SEQUENCE: 25
accaccgagc tgggcacctc cgcc                                          24

<210> SEQ ID NO 26
<211> LENGTH: 8
<212> TYPE: PRT
<213> ORGANISM: Oryctolagus cuniculus

<400> SEQUENCE: 26

Thr Thr Glu Leu Gly Thr Ser Ala
1               5

<210> SEQ ID NO 27
<211> LENGTH: 24
<212> TYPE: DNA
<213> ORGANISM: Rattus rattus

<400> SEQUENCE: 27
accaccgacg agggcaccag cgag                                          24

<210> SEQ ID NO 28
<211> LENGTH: 8
<212> TYPE: PRT
<213> ORGANISM: Rattus rattus

<400> SEQUENCE: 28

Thr Thr Asp Glu Gly Thr Ser Glu
1               5

<210> SEQ ID NO 29
<211> LENGTH: 57
<212> TYPE: DNA
<213> ORGANISM: Homo sapiens

<400> SEQUENCE: 29
gtggacgccg ccctggccct gcccgcccac agctacagcg gcagggagag ggtgtac     57

<210> SEQ ID NO 30
<211> LENGTH: 19
<212> TYPE: PRT
<213> ORGANISM: Homo sapiens

<400> SEQUENCE: 30

Val Asp Ala Ala Leu Ala Leu Pro Ala His Ser Tyr Ser Gly Arg Glu
1               5                   10                  15

Arg Val Tyr

<210> SEQ ID NO 31
<211> LENGTH: 57
<212> TYPE: DNA
<213> ORGANISM: Sus scrofa

<400> SEQUENCE: 31
gtggacgccg ccctggccct gcccgcccac agctacagcg gccgcgagcg cgtgtac     57

<210> SEQ ID NO 32
<211> LENGTH: 19
<212> TYPE: PRT
<213> ORGANISM: Sus scrofa

<400> SEQUENCE: 32

Val Asp Ala Ala Leu Ala Leu Pro Ala His Ser Tyr Ser Gly Arg Glu
1               5                   10                  15

Arg Val Tyr

<210> SEQ ID NO 33
<211> LENGTH: 57
<212> TYPE: DNA
<213> ORGANISM: Bos taurus

<400> SEQUENCE: 33
gtggacgccg ccctggccct gcccgcccac aacttcaacg gcagggagag ggtgtac         57

<210> SEQ ID NO 34
<211> LENGTH: 19
<212> TYPE: PRT
<213> ORGANISM: Bos taurus

<400> SEQUENCE: 34

Val Asp Ala Ala Leu Ala Leu Pro Ala His Asn Phe Asn Gly Arg Glu
1               5                   10                  15

Arg Val Tyr

<210> SEQ ID NO 35
<211> LENGTH: 57
<212> TYPE: DNA
<213> ORGANISM: Capra hircus

<400> SEQUENCE: 35
gtggacgccg ccctggccct gcccgcccac agctacaacg gccgcgagcg cgtgtac         57

<210> SEQ ID NO 36
<211> LENGTH: 19
<212> TYPE: PRT
<213> ORGANISM: Capra hircus

<400> SEQUENCE: 36

Val Asp Ala Ala Leu Ala Leu Pro Ala His Ser Tyr Asn Gly Arg Glu
1               5                   10                  15

Arg Val Tyr

<210> SEQ ID NO 37
<211> LENGTH: 57
<212> TYPE: DNA
<213> ORGANISM: Mus musculus

<400> SEQUENCE: 37
gtggacgccg ccttcgccct gcccgcccac aggtacagcg gcagggagag ggtgtac         57

<210> SEQ ID NO 38
<211> LENGTH: 19
<212> TYPE: PRT
<213> ORGANISM: Mus musculus

<400> SEQUENCE: 38

Val Asp Ala Ala Phe Ala Leu Pro Ala His Arg Tyr Ser Gly Arg Glu
1               5                   10                  15

Arg Val Tyr

<210> SEQ ID NO 39
<211> LENGTH: 57
<212> TYPE: DNA
<213> ORGANISM: Oryctolagus cuniculus

<400> SEQUENCE: 39
gtggacgccg ccttcgccct gcccgcccac tcctactccg gccgcgagcg cgtgtac      57

<210> SEQ ID NO 40
<211> LENGTH: 19
<212> TYPE: PRT
<213> ORGANISM: Oryctolagus cuniculus

<400> SEQUENCE: 40

Val Asp Ala Ala Phe Ala Leu Pro Ala His Ser Tyr Ser Gly Arg Glu
1               5                   10                  15

Arg Val Tyr

<210> SEQ ID NO 41
<211> LENGTH: 57
<212> TYPE: DNA
<213> ORGANISM: Rattus rattus

<400> SEQUENCE: 41
gtggacgccg ccctggccct gcccgcccac agctacagcg gcagggagag ggtgtac      57

<210> SEQ ID NO 42
<211> LENGTH: 19
<212> TYPE: PRT
<213> ORGANISM: Rattus rattus

<400> SEQUENCE: 42

Val Asp Ala Ala Leu Ala Leu Pro Ala His Ser Tyr Ser Gly Arg Glu
1               5                   10                  15

Arg Val Tyr

<210> SEQ ID NO 43
<211> LENGTH: 57
<212> TYPE: DNA
<213> ORGANISM: Homo sapiens

<400> SEQUENCE: 43
aagggcaagc agtactggga gtaccagttc cagcaccagc ccagccagga ggagtgc      57

<210> SEQ ID NO 44
<211> LENGTH: 19
<212> TYPE: PRT
<213> ORGANISM: Homo sapiens

<400> SEQUENCE: 44

Lys Gly Lys Gln Tyr Trp Glu Tyr Gln Phe Gln His Gln Pro Ser Gln
1               5                   10                  15

Glu Glu Cys

<210> SEQ ID NO 45
<211> LENGTH: 57
<212> TYPE: DNA
<213> ORGANISM: Sus scrofa

<400> SEQUENCE: 45
aagggcaagc agtactggga gtacgtgttc cagcagcagc ccagccgcga ggagtgc      57

<210> SEQ ID NO 46
<211> LENGTH: 19
<212> TYPE: PRT
<213> ORGANISM: Sus scrofa

<400> SEQUENCE: 46

Lys Gly Lys Gln Tyr Trp Glu Tyr Val Phe Gln Gln Gln Pro Ser Arg
1               5                   10                  15

Glu Glu Cys

<210> SEQ ID NO 47
<211> LENGTH: 57
<212> TYPE: DNA
<213> ORGANISM: Bos taurus

<400> SEQUENCE: 47
aagggcaacc actactggga gtacgtgttc cagcagcagc ccagccagga ggactgc     57

<210> SEQ ID NO 48
<211> LENGTH: 19
<212> TYPE: PRT
<213> ORGANISM: Bos taurus

<400> SEQUENCE: 48

Lys Gly Asn His Tyr Trp Glu Tyr Val Phe Gln Gln Gln Pro Ser Gln
1               5                   10                  15

Glu Asp Cys

<210> SEQ ID NO 49
<211> LENGTH: 57
<212> TYPE: DNA
<213> ORGANISM: Capra hircus

<400> SEQUENCE: 49
aagggcaacc actactggga gtacgtgttc cagcagcagc ccagccgcga ggagtgc     57

<210> SEQ ID NO 50
<211> LENGTH: 19
<212> TYPE: PRT
<213> ORGANISM: Capra hircus

<400> SEQUENCE: 50

Lys Gly Asn His Tyr Trp Glu Tyr Val Phe Gln Gln Gln Pro Ser Arg
1               5                   10                  15

Glu Glu Cys

<210> SEQ ID NO 51
<211> LENGTH: 57
<212> TYPE: DNA
<213> ORGANISM: Mus musculus

<400> SEQUENCE: 51
aagggcaagc agtactggga gtacgagttc cagcagcagc ccagccagga ggagtgc     57

<210> SEQ ID NO 52
<211> LENGTH: 19
<212> TYPE: PRT
<213> ORGANISM: Mus musculus

<400> SEQUENCE: 52

Lys Gly Lys Gln Tyr Trp Glu Tyr Glu Phe Gln Gln Gln Pro Ser Gln
1               5                   10                  15

Glu Glu Cys

<210> SEQ ID NO 53

```
<211> LENGTH: 57
<212> TYPE: DNA
<213> ORGANISM: Oryctolagus cuniculus

<400> SEQUENCE: 53
aagggcgaca agtactggga gtaccagttc cagcagcagc cctcccagga ggagtgc        57

<210> SEQ ID NO 54
<211> LENGTH: 19
<212> TYPE: PRT
<213> ORGANISM: Oryctolagus cuniculus

<400> SEQUENCE: 54

Lys Gly Asp Lys Tyr Trp Glu Tyr Gln Phe Gln Gln Gln Pro Ser Gln
1               5                   10                  15

Glu Glu Cys

<210> SEQ ID NO 55
<211> LENGTH: 57
<212> TYPE: DNA
<213> ORGANISM: Rattus rattus

<400> SEQUENCE: 55
aagggcaagc agtactggga gtacgagttc cagcagcagc ccagccagga ggagtgc        57

<210> SEQ ID NO 56
<211> LENGTH: 19
<212> TYPE: PRT
<213> ORGANISM: Rattus rattus

<400> SEQUENCE: 56

Lys Gly Lys Gln Tyr Trp Glu Tyr Glu Phe Gln Gln Gln Pro Ser Gln
1               5                   10                  15

Glu Glu Cys

<210> SEQ ID NO 57
<211> LENGTH: 75
<212> TYPE: DNA
<213> ORGANISM: Homo sapiens

<400> SEQUENCE: 57
ttcgagcact cgccatgat gcagagggac agctgggagg acatcttcga gctgctgttc       60
tggggcagga ccagc                                                      75

<210> SEQ ID NO 58
<211> LENGTH: 25
<212> TYPE: PRT
<213> ORGANISM: Homo sapiens

<400> SEQUENCE: 58

Phe Glu His Phe Ala Met Met Gln Arg Asp Ser Trp Glu Asp Ile Phe
1               5                   10                  15

Glu Leu Leu Phe Trp Gly Arg Thr Ser
            20                  25

<210> SEQ ID NO 59
<211> LENGTH: 75
<212> TYPE: DNA
<213> ORGANISM: Sus scrofa

<400> SEQUENCE: 59
ttcgcccact cgccctgat gcagcgcgac agctgggagg acatcttccg cctgctgttc       60
```

```
tggagccaca gcttc                                                          75

<210> SEQ ID NO 60
<211> LENGTH: 25
<212> TYPE: PRT
<213> ORGANISM: Sus scrofa

<400> SEQUENCE: 60

Phe Ala His Phe Ala Leu Met Gln Arg Asp Ser Trp Glu Asp Ile Phe
1               5                   10                  15

Arg Leu Leu Phe Trp Ser His Ser Phe
            20                  25

<210> SEQ ID NO 61
<211> LENGTH: 75
<212> TYPE: DNA
<213> ORGANISM: Bos taurus

<400> SEQUENCE: 61
ttcaagcact tcgccctgat gcagagggac agctgggtgg acatcttcag gctgctgttc       60
tggggcggca gctac                                                         75

<210> SEQ ID NO 62
<211> LENGTH: 25
<212> TYPE: PRT
<213> ORGANISM: Bos taurus

<400> SEQUENCE: 62

Phe Lys His Phe Ala Leu Met Gln Arg Asp Ser Trp Val Asp Ile Phe
1               5                   10                  15

Arg Leu Leu Phe Trp Gly Gly Ser Tyr
            20                  25

<210> SEQ ID NO 63
<211> LENGTH: 75
<212> TYPE: DNA
<213> ORGANISM: Capra hircus

<400> SEQUENCE: 63
ttcaagcact tcgccctgat gcagcgcgac agctgggagg acatcttccg cctgctgttc       60
tggggcggca gcttc                                                         75

<210> SEQ ID NO 64
<211> LENGTH: 25
<212> TYPE: PRT
<213> ORGANISM: Capra hircus

<400> SEQUENCE: 64

Phe Lys His Phe Ala Leu Met Gln Arg Asp Ser Trp Glu Asp Ile Phe
1               5                   10                  15

Arg Leu Leu Phe Trp Gly Gly Ser Phe
            20                  25

<210> SEQ ID NO 65
<211> LENGTH: 75
<212> TYPE: DNA
<213> ORGANISM: Mus musculus

<400> SEQUENCE: 65
ttcgagcact tcgccctgct gcagagggac agctgggaga acatcttcga gctgctgttc       60
```
tggggcagga gcagc                                                          75

<210> SEQ ID NO 66
<211> LENGTH: 25
<212> TYPE: PRT
<213> ORGANISM: Mus musculus

<400> SEQUENCE: 66

Phe Glu His Phe Ala Leu Leu Gln Arg Asp Ser Trp Glu Asn Ile Phe
1               5                   10                  15

Glu Leu Leu Phe Trp Gly Arg Ser Ser
            20                  25

<210> SEQ ID NO 67
<211> LENGTH: 75
<212> TYPE: DNA
<213> ORGANISM: Oryctolagus cuniculus

<400> SEQUENCE: 67
ttcgagcact cgccatgct gcaccgcgac tcctgggagg acatcttcaa gctgctgttc      60
tggggccgcc cctcc                                                          75

<210> SEQ ID NO 68
<211> LENGTH: 25
<212> TYPE: PRT
<213> ORGANISM: Oryctolagus cuniculus

<400> SEQUENCE: 68

Phe Glu His Phe Ala Met Leu His Arg Asp Ser Trp Glu Asp Ile Phe
1               5                   10                  15

Lys Leu Leu Phe Trp Gly Arg Pro Ser
            20                  25

<210> SEQ ID NO 69
<211> LENGTH: 75
<212> TYPE: DNA
<213> ORGANISM: Rattus rattus

<400> SEQUENCE: 69
ttcgagcact cgccctgct gcagagggac agctgggaga acatcttcga gctgctgttc      60
tggggcagga gcagc                                                          75

<210> SEQ ID NO 70
<211> LENGTH: 25
<212> TYPE: PRT
<213> ORGANISM: Rattus rattus

<400> SEQUENCE: 70

Phe Glu His Phe Ala Leu Leu Gln Arg Asp Ser Trp Glu Asn Ile Phe
1               5                   10                  15

Glu Leu Leu Phe Trp Gly Arg Ser Ser
            20                  25

<210> SEQ ID NO 71
<211> LENGTH: 66
<212> TYPE: DNA
<213> ORGANISM: Homo sapiens

<400> SEQUENCE: 71
ggcaggacca gcgccggcac caggcagccc cagttcatca gcagggactg gcacggcgtg      60
cccggc                                                                    66

<210> SEQ ID NO 72
<211> LENGTH: 22
<212> TYPE: PRT
<213> ORGANISM: Homo sapiens

<400> SEQUENCE: 72

Gly Arg Thr Ser Ala Gly Thr Arg Gln Pro Gln Phe Ile Ser Arg Asp
1               5                   10                  15

Trp His Gly Val Pro Gly
            20

<210> SEQ ID NO 73
<211> LENGTH: 60
<212> TYPE: DNA
<213> ORGANISM: Sus scrofa

<400> SEQUENCE: 73
agccacagct tcggcggcgc catcgagccc cgcgtgatca gccaggactg gctgggcctg        60

<210> SEQ ID NO 74
<211> LENGTH: 22
<212> TYPE: PRT
<213> ORGANISM: Sus scrofa

<400> SEQUENCE: 74

Ser His Ser Phe Gly Gly Ala Ile Glu Pro Arg Val Ile Ser Gln Asp
1               5                   10                  15

Trp Leu Gly Leu Pro Glu
            20

<210> SEQ ID NO 75
<211> LENGTH: 66
<212> TYPE: DNA
<213> ORGANISM: Bos taurus

<400> SEQUENCE: 75
ggcggcagct acggcggcgc cggccagccc cagctgatca gcaggaactg gttcggcctg        60
cccggc                                                                  66

<210> SEQ ID NO 76
<211> LENGTH: 22
<212> TYPE: PRT
<213> ORGANISM: Bos taurus

<400> SEQUENCE: 76

Gly Gly Ser Tyr Gly Gly Ala Gly Gln Pro Gln Leu Ile Ser Arg Asn
1               5                   10                  15

Trp Phe Gly Leu Pro Gly
            20

<210> SEQ ID NO 77
<211> LENGTH: 66
<212> TYPE: DNA
<213> ORGANISM: Capra hircus

<400> SEQUENCE: 77
ggcggcagct tcggcggcgc cggccagccc cagctgatca gccgcgactg gttcggcctg        60
cccggc                                                                  66

<210> SEQ ID NO 78

```
<211> LENGTH: 22
<212> TYPE: PRT
<213> ORGANISM: Capra hircus

<400> SEQUENCE: 78

Gly Gly Ser Phe Gly Gly Ala Gly Gln Pro Gln Leu Ile Ser Arg Asp
1               5                   10                  15

Trp Phe Gly Leu Pro Gly
            20

<210> SEQ ID NO 79
<211> LENGTH: 66
<212> TYPE: DNA
<213> ORGANISM: Mus musculus

<400> SEQUENCE: 79
ggcaggagca gcgacggcgc cagggagccc cagttcatca gcaggaactg gcacggcgtg      60
cccggc                                                                66

<210> SEQ ID NO 80
<211> LENGTH: 22
<212> TYPE: PRT
<213> ORGANISM: Mus musculus

<400> SEQUENCE: 80

Gly Arg Ser Ser Asp Gly Ala Arg Glu Pro Gln Phe Ile Ser Arg Asn
1               5                   10                  15

Trp His Gly Val Pro Gly
            20

<210> SEQ ID NO 81
<211> LENGTH: 66
<212> TYPE: DNA
<213> ORGANISM: Oryctolagus cuniculus

<400> SEQUENCE: 81
ggccgcccct ccggcggcgc ccgccagccc cagttcatct cccgcgactg gcacggcgtg      60
cccggc                                                                66

<210> SEQ ID NO 82
<211> LENGTH: 22
<212> TYPE: PRT
<213> ORGANISM: Oryctolagus cuniculus

<400> SEQUENCE: 82

Gly Arg Pro Ser Gly Gly Ala Arg Gln Pro Gln Phe Ile Ser Arg Asp
1               5                   10                  15

Trp His Gly Val Pro Gly
            20

<210> SEQ ID NO 83
<211> LENGTH: 66
<212> TYPE: DNA
<213> ORGANISM: Rattus rattus

<400> SEQUENCE: 83
ggcaggagca gcgacggcgc caagggcccc cagttcatca gcagggactg gcacggcgtg      60
cccggc                                                                66

<210> SEQ ID NO 84
<211> LENGTH: 22
```

```
<212> TYPE: PRT
<213> ORGANISM: Rattus rattus

<400> SEQUENCE: 84

Gly Arg Ser Ser Asp Gly Ala Lys Gly Pro Gln Phe Ile Ser Arg Asp
1               5                   10                  15

Trp His Gly Val Pro Gly
            20

<210> SEQ ID NO 85
<211> LENGTH: 66
<212> TYPE: DNA
<213> ORGANISM: Homo sapiens

<400> SEQUENCE: 85
ctgttcagca gcgaggagag caacctgggc gccaacaact acgacgacta caggatggac    60
tggctg                                                               66

<210> SEQ ID NO 86
<211> LENGTH: 22
<212> TYPE: PRT
<213> ORGANISM: Homo sapiens

<400> SEQUENCE: 86

Leu Phe Ser Ser Glu Glu Ser Asn Leu Gly Ala Asn Asn Tyr Asp Asp
1               5                   10                  15

Tyr Arg Met Asp Trp Leu
            20

<210> SEQ ID NO 87
<211> LENGTH: 66
<212> TYPE: DNA
<213> ORGANISM: Sus scrofa

<400> SEQUENCE: 87
tggttcagca gcgaggagac cggccccggc ggctacaact acgacgacta caagatggac    60
tggctg                                                               66

<210> SEQ ID NO 88
<211> LENGTH: 22
<212> TYPE: PRT
<213> ORGANISM: Sus scrofa

<400> SEQUENCE: 88

Trp Phe Ser Ser Glu Glu Thr Gly Pro Gly Gly Tyr Asn Tyr Asp Asp
1               5                   10                  15

Tyr Lys Met Asp Trp Leu
            20

<210> SEQ ID NO 89
<211> LENGTH: 66
<212> TYPE: DNA
<213> ORGANISM: Bos taurus

<400> SEQUENCE: 89
tggctgagca gcgaggagct gggcctgggc gccaacaact acgacagctt cgagatggac    60
tggctg                                                               66

<210> SEQ ID NO 90
<211> LENGTH: 22
<212> TYPE: PRT
```

<213> ORGANISM: Bos taurus

<400> SEQUENCE: 90

Trp Leu Ser Ser Glu Glu Leu Gly Leu Gly Ala Asn Asn Tyr Asp Ser
1               5                   10                  15

Phe Glu Met Asp Trp Leu
            20

<210> SEQ ID NO 91
<211> LENGTH: 66
<212> TYPE: DNA
<213> ORGANISM: Capra hircus

<400> SEQUENCE: 91
tggttcagca gcgaggagct gggcctgggc gccgacaact acgacaacta cgagatggac    60
tggctg                                                               66

<210> SEQ ID NO 92
<211> LENGTH: 22
<212> TYPE: PRT
<213> ORGANISM: Capra hircus

<400> SEQUENCE: 92

Trp Phe Ser Ser Glu Glu Leu Gly Leu Gly Ala Asp Asn Tyr Asp Asn
1               5                   10                  15

Tyr Glu Met Asp Trp Leu
            20

<210> SEQ ID NO 93
<211> LENGTH: 66
<212> TYPE: DNA
<213> ORGANISM: Mus musculus

<400> SEQUENCE: 93
ctgttcagca gcgaggagag cggcctgggc acctacaaca actacgacta cgacatggac    60
tggctg                                                               66

<210> SEQ ID NO 94
<211> LENGTH: 22
<212> TYPE: PRT
<213> ORGANISM: Mus musculus

<400> SEQUENCE: 94

Leu Phe Ser Ser Glu Glu Ser Gly Leu Gly Thr Tyr Asn Asn Tyr Asp
1               5                   10                  15

Tyr Asp Met Asp Trp Leu
            20

<210> SEQ ID NO 95
<211> LENGTH: 66
<212> TYPE: DNA
<213> ORGANISM: Oryctolagus cuniculus

<400> SEQUENCE: 95
tggttctcct ccgaggaggt gtccctgggc ccctacaact acgaggacta cgagacctcc    60
tggctg                                                               66

<210> SEQ ID NO 96
<211> LENGTH: 22
<212> TYPE: PRT
<213> ORGANISM: Oryctolagus cuniculus

<400> SEQUENCE: 96

Trp Phe Ser Ser Glu Glu Val Ser Leu Gly Pro Tyr Asn Tyr Glu Asp
1               5                   10                  15

Tyr Glu Thr Ser Trp Leu
            20

<210> SEQ ID NO 97
<211> LENGTH: 63
<212> TYPE: DNA
<213> ORGANISM: Rattus rattus

<400> SEQUENCE: 97
ctgctgagca gcgaggagag cggcctgggc acctacaact acgactacga catgaactgg      60
ctg                                                                   63

<210> SEQ ID NO 98
<211> LENGTH: 21
<212> TYPE: PRT
<213> ORGANISM: Rattus rattus

<400> SEQUENCE: 98

Leu Leu Ser Ser Glu Glu Ser Gly Leu Gly Thr Tyr Asn Tyr Asp Tyr
1               5                   10                  15

Asp Met Asn Trp Leu
            20

<210> SEQ ID NO 99
<211> LENGTH: 57
<212> TYPE: DNA
<213> ORGANISM: Homo sapiens

<400> SEQUENCE: 99
agggtgaacc tgaggaccag gagggtggac accgtggacc cccctaccc caggagc          57

<210> SEQ ID NO 100
<211> LENGTH: 19
<212> TYPE: PRT
<213> ORGANISM: Homo sapiens

<400> SEQUENCE: 100

Arg Val Asn Leu Arg Thr Arg Arg Val Asp Thr Val Asp Pro Pro Tyr
1               5                   10                  15

Pro Arg Ser

<210> SEQ ID NO 101
<211> LENGTH: 57
<212> TYPE: DNA
<213> ORGANISM: Sus scrofa

<400> SEQUENCE: 101
cgcgtgaacc tgcgcaccca gcgcgtggac accgtgaccc cccctaccc ccgcagc          57

<210> SEQ ID NO 102
<211> LENGTH: 19
<212> TYPE: PRT
<213> ORGANISM: Sus scrofa

<400> SEQUENCE: 102

Arg Val Asn Leu Arg Thr Gln Arg Val Asp Thr Val Thr Pro Pro Tyr
1               5                   10                  15

Pro Arg Ser

<210> SEQ ID NO 103
<211> LENGTH: 57
<212> TYPE: DNA
<213> ORGANISM: Bos taurus

<400> SEQUENCE: 103
agggtgaacc tgaggaccag gagggtggac gccgtgatcc ccccctaccc caggagc        57

<210> SEQ ID NO 104
<211> LENGTH: 19
<212> TYPE: PRT
<213> ORGANISM: Bos taurus

<400> SEQUENCE: 104

Arg Val Asn Leu Arg Thr Arg Arg Val Asp Ala Val Ile Pro Pro Tyr
1               5                   10                  15

Pro Arg Ser

<210> SEQ ID NO 105
<211> LENGTH: 57
<212> TYPE: DNA
<213> ORGANISM: Capra hircus

<400> SEQUENCE: 105
cgcgtgaacc tgcgcacccg ccgcgtggac agcgtgatcc ccccctaccc ccgcagc        57

<210> SEQ ID NO 106
<211> LENGTH: 19
<212> TYPE: PRT
<213> ORGANISM: Capra hircus

<400> SEQUENCE: 106

Arg Val Asn Leu Arg Thr Arg Arg Val Asp Ser Val Ile Pro Pro Tyr
1               5                   10                  15

Pro Arg Ser

<210> SEQ ID NO 107
<211> LENGTH: 57
<212> TYPE: DNA
<213> ORGANISM: Mus musculus

<400> SEQUENCE: 107
agggtgaacc tgaggaccag gagggtggac agcgtgaacc ccccctaccc caggagc        57

<210> SEQ ID NO 108
<211> LENGTH: 19
<212> TYPE: PRT
<213> ORGANISM: Mus musculus

<400> SEQUENCE: 108

Arg Val Asn Leu Arg Thr Arg Arg Val Asp Ser Val Asn Pro Pro Tyr
1               5                   10                  15

Pro Arg Ser

<210> SEQ ID NO 109
<211> LENGTH: 57
<212> TYPE: DNA
<213> ORGANISM: Oryctolagus cuniculus

<400> SEQUENCE: 109

```
cgcgtgaacc tgcgcaccca gcgcgtggac accgtgaacc cccctaccc ccgctcc        57
```

<210> SEQ ID NO 110
<211> LENGTH: 19
<212> TYPE: PRT
<213> ORGANISM: Oryctolagus cuniculus

<400> SEQUENCE: 110

Arg Val Asn Leu Arg Thr Gln Arg Val Asp Thr Val Asn Pro Pro Tyr
1               5                   10                  15

Pro Arg Ser

<210> SEQ ID NO 111
<211> LENGTH: 57
<212> TYPE: DNA
<213> ORGANISM: Rattus rattus

<400> SEQUENCE: 111

```
agggtgaacc tgaggaccag gagggtggac agcgtgaacc cccctaccc caggagc        57
```

<210> SEQ ID NO 112
<211> LENGTH: 19
<212> TYPE: PRT
<213> ORGANISM: Rattus rattus

<400> SEQUENCE: 112

Arg Val Asn Leu Arg Thr Arg Arg Val Asp Ser Val Asn Pro Pro Tyr
1               5                   10                  15

Pro Arg Ser

<210> SEQ ID NO 113
<211> LENGTH: 19
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: is selected from small amino acid residues, or
      modified forms thereof
<220> FEATURE:
<221> NAME/KEY: MISC_FEATURE
<222> LOCATION: (15)..(15)
<223> OTHER INFORMATION: is selected from small amino acid residues, or
      modified forms thereof, or hydrophobic amino acid residues, or
      modified forms thereof
<220> FEATURE:
<221> NAME/KEY: MISC_FEATURE
<222> LOCATION: (17)..(17)
<223> OTHER INFORMATION: is selected from hydrophobic amino acid
      residues, or modified forms thereof
<220> FEATURE:
<221> NAME/KEY: MISC_FEATURE
<222> LOCATION: (18)..(18)
<223> OTHER INFORMATION: is selected from small amino acid residues, or
      modified forms thereof, or hydrophobic amino acid residues, or
      modified forms thereof; and
<220> FEATURE:
<221> NAME/KEY: MISC_FEATURE
<222> LOCATION: (19)..(19)
<223> OTHER INFORMATION: is selected from small amino acid residues, or
      modified forms thereof, or acidic amino acid residues, or modified
      forms thereof

<400> SEQUENCE: 113

Cys Gln Cys Asp Glu Leu Cys Xaa Tyr Tyr Gln Ser Cys Cys Xaa Asp
1               5                   10                  15

Xaa Xaa Xaa

```
<210> SEQ ID NO 114
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: is selected from any amino acid residue, or
      modified forms thereof, or small amino acid residues, or modified
      forms thereof, or hydrophobic amino acid residues, or modified
      forms thereof
<220> FEATURE:
<221> NAME/KEY: MISC_FEATURE
<222> LOCATION: (3)..(3)
<223> OTHER INFORMATION: is selected from charged amino acid residues,
      or modified forms thereof, or acidic amino acid residues, or
      modified forms thereof
<220> FEATURE:
<221> NAME/KEY: MISC_FEATURE
<222> LOCATION: (4)..(4)
<223> OTHER INFORMATION: is selected from any amino acid residue, or
      modified forms thereof, or hydrophobic amino acid residues, or
      modified forms thereof, or neutral/polar amino acid residues, or
      modified forms thereof, or acidic amino acid residues, or modified
      forms thereof
<220> FEATURE:
<221> NAME/KEY: MISC_FEATURE
<222> LOCATION: (6)..(6)
<223> OTHER INFORMATION: is selected from any amino acid residue, or
      modified forms thereof, or hydrophobic amino acid residues, or
      modified forms thereof, or small amino acid residues, or modified
      forms thereof
<220> FEATURE:
<221> NAME/KEY: MISC_FEATURE
<222> LOCATION: (7)..(7)
<223> OTHER INFORMATION: is selected from small amino acid residues, or
      modified forms thereof
<220> FEATURE:
<221> NAME/KEY: MISC_FEATURE
<222> LOCATION: (8)..(8)
<223> OTHER INFORMATION: is selected from any amino acid residue, or
      modified forms thereof, or acidic amino acid residues, or modified
      forms thereof, or small amino acid residues, or modified forms
      thereof

<400> SEQUENCE: 114

Thr Xaa Xaa Xaa Gly Xaa Xaa Xaa
1               5

<210> SEQ ID NO 115
<211> LENGTH: 19
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: is selected from hydrophobic amino acid
      residues, or modified forms thereof, and aromatic amino acid
      residues, or modified forms thereof
<220> FEATURE:
<221> NAME/KEY: MISC_FEATURE
<222> LOCATION: (11)..(11)
<223> OTHER INFORMATION: is selected from any amino acid residue, or
      modified forms thereof, or neutral/polar amino acid residues, or
      modified forms thereof, or basic amino acid residues, or modified
      forms thereof
<220> FEATURE:
<221> NAME/KEY: MISC_FEATURE
<222> LOCATION: (12)..(12)
<223> OTHER INFORMATION: is selected from hydrophobic amino acid
      residues, or modified forms thereof
<220> FEATURE:
<221> NAME/KEY: MISC_FEATURE
<222> LOCATION: (13)..(13)
<223> OTHER INFORMATION: is selected from small amino acid residues, or
      modified forms thereof, or neutral/polar amino acid residues, or
```

```
              modified forms thereof

<400> SEQUENCE: 115

Val Asp Ala Ala Xaa Ala Leu Pro Ala His Xaa Xaa Xaa Gly Arg Glu
1               5                   10                  15

Arg Val Tyr

<210> SEQ ID NO 116
<211> LENGTH: 19
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: is selected from charged amino acid residues,
      or modified forms thereof, and acidic amino acid residues, or
      modified forms thereof, or neutral/polar amino acid residues, or
      modified forms thereof
<220> FEATURE:
<221> NAME/KEY: MISC_FEATURE
<222> LOCATION: (4)..(4)
<223> OTHER INFORMATION: is selected from neutral/polar amino acid
      residues, or modified forms thereof, or basic amino acid residues,
      or modified forms thereof
<220> FEATURE:
<221> NAME/KEY: MISC_FEATURE
<222> LOCATION: (9)..(9)
<223> OTHER INFORMATION: is selected from any amino acid residue, or
      modified forms thereof, or hydrophobic amino acid residues, or
      modified forms thereof, or acidic amino acid residues, or modified
      forms thereof
<220> FEATURE:
<221> NAME/KEY: MISC_FEATURE
<222> LOCATION: (12)..(12)
<223> OTHER INFORMATION: is selected from basic amino acid residues, or
      modified forms thereof, or neutral/polar amino acid residues, or
      modified forms thereof
<220> FEATURE:
<221> NAME/KEY: MISC_FEATURE
<222> LOCATION: (16)..(16)
<223> OTHER INFORMATION: is selected from neutral/polar amino acid
      residues, or modified forms thereof, or basic amino acid residues,
      or modified forms thereof
<220> FEATURE:
<221> NAME/KEY: MISC_FEATURE
<222> LOCATION: (18)..(18)
<223> OTHER INFORMATION: is selected from acidic amino acid residues, or
      modified forms thereof

<400> SEQUENCE: 116

Lys Gly Xaa Xaa Tyr Trp Glu Tyr Xaa Phe Gln Xaa Gln Pro Ser Xaa
1               5                   10                  15

Glu Xaa Cys

<210> SEQ ID NO 117
<211> LENGTH: 25
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: is selected from charged amino acid residues,
      or modified forms thereof, and basic amino acid residues, or
      modified forms thereof, or small amino acid residues, or modified
      forms thereof
<220> FEATURE:
<221> NAME/KEY: MISC_FEATURE
<222> LOCATION: (6)..(7)
<223> OTHER INFORMATION: is selected from hydrophobic amino acid
      residues, or modified forms thereof
<220> FEATURE:
<221> NAME/KEY: MISC_FEATURE
<222> LOCATION: (8)..(8)
```

```
<223> OTHER INFORMATION: is selected from neutral/polar amino acid
      residues, or modified forms thereof, or basic amino acid
      residues, or modified forms thereof
<220> FEATURE:
<221> NAME/KEY: MISC_FEATURE
<222> LOCATION: (13)..(13)
<223> OTHER INFORMATION: is selected from acidic amino acid residues,
      or modified forms thereof, or hydrophobic amino acid residues, or
      modified forms thereof
<220> FEATURE:
<221> NAME/KEY: MISC_FEATURE
<222> LOCATION: (14)..(14)
<223> OTHER INFORMATION: is selected from acidic amino acid residues, or
      modified forms thereof , or neutral/polar amino acid residues, or
      modified forms thereof
<220> FEATURE:
<221> NAME/KEY: MISC_FEATURE
<222> LOCATION: (17)..(17)
<223> OTHER INFORMATION: is selected from charged amino acid residues,
      or modified forms thereof, or acidic amino acid residues, or
      modified forms thereof
<220> FEATURE:
<221> NAME/KEY: MISC_FEATURE
<222> LOCATION: (22)..(22)
<223> OTHER INFORMATION: is selected from small amino acid residues,
      or modified forms thereof
<220> FEATURE:
<221> NAME/KEY: MISC_FEATURE
<222> LOCATION: (23)..(23)
<223> OTHER INFORMATION: is selected from basic amino acid residues, or
      modified forms thereof, or small amino acid residues, or modified
      forms thereof
<220> FEATURE:
<221> NAME/KEY: MISC_FEATURE
<222> LOCATION: (24)..(24)
<223> OTHER INFORMATION: is selected from small amino acid residues, or
      modified forms thereof
<220> FEATURE:
<221> NAME/KEY: MISC_FEATURE
<222> LOCATION: (25)..(25)
<223> OTHER INFORMATION: is selected from small amino acid residues, or
      modified forms thereof, or hydrophobic amino acid residues, or
      modified forms thereof

<400> SEQUENCE: 117

Phe Xaa His Phe Ala Xaa Xaa Xaa Arg Asp Ser Trp Xaa Xaa Ile Phe
1               5                   10                  15

Xaa Leu Leu Phe Trp Xaa Xaa Xaa Xaa
            20                  25

<210> SEQ ID NO 118
<211> LENGTH: 22
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: is selected from small amino acid residues,
      or modified forms thereof
<220> FEATURE:
<221> NAME/KEY: MISC_FEATURE
<222> LOCATION: (2)..(2)
<223> OTHER INFORMATION: is selected from basic amino acid residues, or
      modified forms thereof, and small amino acid residues, or modified
      forms thereof
<220> FEATURE:
<221> NAME/KEY: MISC_FEATURE
<222> LOCATION: (3)..(3)
<223> OTHER INFORMATION: is selected from small amino acid residues, or
      modified forms thereof
<220> FEATURE:
<221> NAME/KEY: MISC_FEATURE
<222> LOCATION: (4)..(4)
<223> OTHER INFORMATION: is selected from small amino acid residues, or
      modified forms thereof, or hydrophobic amino acid residues, or
      modified forms thereof
```

```
<220> FEATURE:
<221> NAME/KEY: MISC_FEATURE
<222> LOCATION: (5)..(5)
<223> OTHER INFORMATION: is selected from small amino acid residues, or
      modified forms thereof, or acidic amino acid residues, or modified
      forms thereof
<220> FEATURE:
<221> NAME/KEY: MISC_FEATURE
<222> LOCATION: (7)..(7)
<223> OTHER INFORMATION: is selected from small amino acid residues, or
      modified forms thereof
<220> FEATURE:
<221> NAME/KEY: MISC_FEATURE
<222> LOCATION: (8)..(8)
<223> OTHER INFORMATION: is selected from any amino acid residue, or
      modified forms thereof, or hydrophobic amino acid residues, or
      modified forms thereof, or small amino acid residues, or modified
      forms thereof
<220> FEATURE:
<221> NAME/KEY: MISC_FEATURE
<222> LOCATION: (9)..(9)
<223> OTHER INFORMATION: is selected from any amino acid residue, or
      modified forms thereof, or acidic amino acid residues, or modified
      forms thereof, or small amino acid residues, or modified forms
      thereof
<220> FEATURE:
<221> NAME/KEY: MISC_FEATURE
<222> LOCATION: (11)..(11)
<223> OTHER INFORMATION: is selected from neutral/polar amino acid
      residues, or modified forms thereof, or basic amino acid residues,
      or modified forms thereof
<220> FEATURE:
<221> NAME/KEY: MISC_FEATURE
<222> LOCATION: (12)..(12)
<223> OTHER INFORMATION: is selected from hydrophobic amino acid
      residues, or modified forms thereof, and aliphatic amino acid
      residues, or modified forms thereof
<220> FEATURE:
<221> NAME/KEY: MISC_FEATURE
<222> LOCATION: (15)..(15)
<223> OTHER INFORMATION: is selected from basic amino acid residues, or
      modified forms thereof, or neutral/polar amino acid residues, or
      modified forms thereof
<220> FEATURE:
<221> NAME/KEY: MISC_FEATURE
<222> LOCATION: (16)..(16)
<223> OTHER INFORMATION: is selected from acidic amino acid residues, or
      modified forms, or neutral/polar amino acid residues, or modified
      forms thereof
<220> FEATURE:
<221> NAME/KEY: MISC_FEATURE
<222> LOCATION: (18)..(18)
<223> OTHER INFORMATION: is selected from basic amino acid residues, or
      modified forms thereof, or hydrophobic amino acid residues, or
      modified forms thereof, and aromatic amino acid residues, or
      modified forms thereof
<220> FEATURE:
<221> NAME/KEY: MISC_FEATURE
<222> LOCATION: (20)..(20)
<223> OTHER INFORMATION: is selected from hydrophobic amino acid
      residues, or modified forms thereof
<220> FEATURE:
<221> NAME/KEY: MISC_FEATURE
<222> LOCATION: (22)..(22)
<223> OTHER INFORMATION: is selected from small amino acid residues, or
      modified forms thereof, or acidic amino acid residues, or modified
      forms thereof

<400> SEQUENCE: 118

Xaa Xaa Xaa Xaa Xaa Gly Xaa Xaa Xaa Pro Xaa Xaa Ile Ser Xaa Xaa
1               5                   10                  15

Trp Xaa Gly Xaa Pro Xaa
            20

<210> SEQ ID NO 119
<211> LENGTH: 22
```

```
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: is selected from hydrophobic amino acid
      residues, or modified forms thereof, and aromatic amino acid
      residues, or modified forms thereof
<220> FEATURE:
<221> NAME/KEY: MISC_FEATURE
<222> LOCATION: (2)..(2)
<223> OTHER INFORMATION: is selected from hydrophobic amino acid
      residues, or modified forms thereof, and aromatic amino acide
      residues, or modified forms thereof
<220> FEATURE:
<221> NAME/KEY: MISC_FEATURE
<222> LOCATION: (7)..(7)
<223> OTHER INFORMATION: is selected from small amino acid residues, or
      modified forms thereof, or hydrophobic amino acid residues, or
      modified forms thereof
<220> FEATURE:
<221> NAME/KEY: MISC_FEATURE
<222> LOCATION: (8)..(8)
<223> OTHER INFORMATION: is selected from small amino acid residues, or
      modified forms thereof, or neutral/polar amino acid residues, or
      modified forms thereof
<220> FEATURE:
<221> NAME/KEY: MISC_FEATURE
<222> LOCATION: (9)..(9)
<223> OTHER INFORMATION: is selected from small amino acid residues, or
      modified forms thereof, or hydrophobic amino acid residues, or
      modified forms thereof
<220> FEATURE:
<221> NAME/KEY: MISC_FEATURE
<222> LOCATION: (11)..(11)
<223> OTHER INFORMATION: is selected from small amino acid residues, or
      modified forms thereof
<220> FEATURE:
<221> NAME/KEY: MISC_FEATURE
<222> LOCATION: (12)..(12)
<223> OTHER INFORMATION: is selected from any amino acid residue, or
      modified forms thereof, or acidic amino acid residues, or modified
      forms thereof, or hydrophobic amino acid residues, or modified
      forms thereof
<220> FEATURE:
<221> NAME/KEY: MISC_FEATURE
<222> LOCATION: (14)..(14)
<223> OTHER INFORMATION: is absent or is selected from neutral/polar
      amino acid residues, or modified forms thereof, or hydrophobic
      amino acid residues, or modified forms thereof
<220> FEATURE:
<221> NAME/KEY: MISC_FEATURE
<222> LOCATION: (15)..(15)
<223> OTHER INFORMATION: is selected from acidic amino acid residues, or
      modified forms thereof, or hydrophoic amino acid residues, or
      modified forms thereof
<220> FEATURE:
<221> NAME/KEY: MISC_FEATURE
<222> LOCATION: (16)..(16)
<223> OTHER INFORMATION: is selected from any amino acid residues, or
      modified forms thereof, or neutral/polar amino acid residues, or
      modified forms thereof, or small amino acid residues, or modified
      forms thereof
<220> FEATURE:
<221> NAME/KEY: MISC_FEATURE
<222> LOCATION: (17)..(17)
<223> OTHER INFORMATION: is selected from hydrophobic amino acid
      residues, or modified forms thereof
<220> FEATURE:
<221> NAME/KEY: MISC_FEATURE
<222> LOCATION: (18)..(18)
<223> OTHER INFORMATION: is selected from charged amino acid residues,
      or modified forms thereof, or acidic amino acid residues, or
      modified forms thereof
<220> FEATURE:
<221> NAME/KEY: MISC_FEATURE
<222> LOCATION: (19)..(19)
<223> OTHER INFORMATION: is selected from hydrophobic amino acid
      residues, or modified forms thereof, or small amino acid residues,
```

```
        or modified forms thereof; and
<220> FEATURE:
<221> NAME/KEY: MISC_FEATURE
<222> LOCATION: (20)..(20)
<223> OTHER INFORMATION: is selected from any amino acid residues, or
      modified forms thereof, or small amino acid residues, or modified
      forms thereof, or neutral/polar amino acid residues, or modified
      forms thereof

<400> SEQUENCE: 119

Xaa Xaa Ser Ser Glu Glu Xaa Xaa Xaa Gly Xaa Xaa Asn Xaa Xaa Xaa
1               5                   10                  15

Xaa Xaa Xaa Xaa Trp Leu
            20

<210> SEQ ID NO 121
<211> LENGTH: 19
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: is selected from basic amino acid residues, or
      modified forms thereof, and neutral/polar amino acid residues, or
      modified forms thereof
<220> FEATURE:
<221> NAME/KEY: MISC_FEATURE
<222> LOCATION: (11)..(11)
<223> OTHER INFORMATION: is selected from small amino acid residues, or
      modified forms thereof
<220> FEATURE:
<221> NAME/KEY: MISC_FEATURE
<222> LOCATION: (13)..(13)
<223> OTHER INFORMATION: is selected from any amino acid residue, or
      modified forms thereof, or small amino acid residues, or modified
      forms thereof, or neutral/polar amino acid residues, or modified
      forms thereof, or hydrophobic amino acid residues, or modified
      forms thereof

<400> SEQUENCE: 120

Arg Val Asn Leu Arg Thr Xaa Arg Val Asp Xaa Val Xaa Pro Pro Tyr
1               5                   10                  15

Pro Arg Ser

<210> SEQ ID NO 121
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: is absent or is selected from at least one of a
      proteinaceous moiety comprising from about 1 to about 50 amino
      acid residues (and all integer amino acid residues therebetween),
      and a protecting moiety
<220> FEATURE:
<221> NAME/KEY: MISC_FEATURE
<222> LOCATION: (9)..(9)
<223> OTHER INFORMATION: is selected from small amino acid residues, or
      modified forms thereof;
<220> FEATURE:
<221> NAME/KEY: MISC_FEATURE
<222> LOCATION: (16)..(16)
<223> OTHER INFORMATION: is selected from small amino acid residues, or
      modified forms thereof, or hydrophobic amino acid residues, or
      modified forms thereof
<220> FEATURE:
<221> NAME/KEY: MISC_FEATURE
<222> LOCATION: (18)..(18)
<223> OTHER INFORMATION: is selected from hydrophobic amino acid
      residues, or modified forms thereof
<220> FEATURE:
<221> NAME/KEY: MISC_FEATURE
```

```
<222> LOCATION: (19)..(19)
<223> OTHER INFORMATION: is selected from small amino acid residues, or
      modified forms thereof, or hydrophobic amino acid residues, or
      modified forms thereof; and
<220> FEATURE:
<221> NAME/KEY: MISC_FEATURE
<222> LOCATION: (20)..(20)
<223> OTHER INFORMATION: is selected from small amino acid residues, or
      modified forms thereof, or acidic amino acid residues, or modified
      forms thereof
<220> FEATURE:
<221> NAME/KEY: MISC_FEATURE
<222> LOCATION: (21)..(21)
<223> OTHER INFORMATION: is absent or is a proteinaceous moiety
      comprising from about 1 to about 50 amino acid residues (and all
      integer amino acid residues therebetween).

<400> SEQUENCE: 121

Xaa Cys Gln Cys Asp Glu Leu Cys Xaa Tyr Tyr Gln Ser Cys Cys Xaa
1               5                   10                  15

Asp Xaa Xaa Xaa Xaa
            20

<210> SEQ ID NO 122
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: is absent or is selected from at least one of
      a proteinaceous moiety comprising from about 1 to about 50 amino
      acid residues (and all integer amino acid residues therebetween),
      and a protecting moiety
<220> FEATURE:
<221> NAME/KEY: MISC_FEATURE
<222> LOCATION: (3)..(3)
<223> OTHER INFORMATION: is selected from any amino acid residue, or
      modified forms thereof, or small amino acid residues, or modified
      forms thereof, or hydrophobic amino acid residues, or modified
      forms thereof
<220> FEATURE:
<221> NAME/KEY: MISC_FEATURE
<222> LOCATION: (4)..(4)
<223> OTHER INFORMATION: is selected from charged amino acid residues,
      or modified forms thereof, or acidic amino acid residues, or
      modified forms thereof
<220> FEATURE:
<221> NAME/KEY: MISC_FEATURE
<222> LOCATION: (5)..(5)
<223> OTHER INFORMATION: is selected from any amino acid residue, or
      modified forms thereof, or hydrophobic amino acid residues, or
      modified forms thereof, or neutral/polar amino acid residues, or
      modified forms thereof, or acidic amino acid residues, or modified
      forms
<220> FEATURE:
<221> NAME/KEY: MISC_FEATURE
<222> LOCATION: (7)..(7)
<223> OTHER INFORMATION: is selected from any amino acid residue, or
      modified forms thereof, or hydrophobic amino acid residues, or
      modified forms thereof, or small amino acid residues, or modified
      forms thereof
<220> FEATURE:
<221> NAME/KEY: MISC_FEATURE
<222> LOCATION: (8)..(8)
<223> OTHER INFORMATION: is selected from small amino acid residues, or
      modified forms thereof
<220> FEATURE:
<221> NAME/KEY: MISC_FEATURE
<222> LOCATION: (9)..(9)
<223> OTHER INFORMATION: is selected from any amino acid residue, or
      modified forms thereof, or acidic amino acid residues, or modified
      forms thereof, or small amino acid residues, or modified forms
      thereof
<220> FEATURE:
<221> NAME/KEY: MISC_FEATURE
```

```
<222> LOCATION: (10)..(10)
<223> OTHER INFORMATION: is absent or is a proteinaceous moiety
      comprising from about 1 to about 50 amino acid residues (and all
      integer amino acid residues therebetween)

<400> SEQUENCE: 122

Xaa Thr Xaa Xaa Xaa Gly Xaa Xaa Xaa Xaa
1               5                   10

<210> SEQ ID NO 123
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: is absent or is selected from at least one of
      a proteinaceous moiety comprising from about 1 to about 50 amino
      acid residues (and all integer amino acid residues therebetween),
      and a protecting moiety
<220> FEATURE:
<221> NAME/KEY: MISC_FEATURE
<222> LOCATION: (6)..(6)
<223> OTHER INFORMATION: is selected from hydrophobic amino acid
      residues, or modified forms thereof, and aromatic amino acid
      residues, or modified forms thereof
<220> FEATURE:
<221> NAME/KEY: MISC_FEATURE
<222> LOCATION: (12)..(12)
<223> OTHER INFORMATION: is selected from any amino acid residue, or
      modified forms thereof, or neutral/polar amino acid residues, or
      modified forms thereof, or basic amino acid residues, or modified
      forms thereof
<220> FEATURE:
<221> NAME/KEY: MISC_FEATURE
<222> LOCATION: (13)..(13)
<223> OTHER INFORMATION: is selected from hydrophobic amino acid
      residues, or modified forms thereof
<220> FEATURE:
<221> NAME/KEY: MISC_FEATURE
<222> LOCATION: (14)..(14)
<223> OTHER INFORMATION: s selected from small amino acid residues, or
      modified forms thereof, or neutral/polar amino acid residues, or
      modified forms thereof
<220> FEATURE:
<221> NAME/KEY: MISC_FEATURE
<222> LOCATION: (21)..(21)
<223> OTHER INFORMATION: is absent or is a proteinaceous moiety
      comprising from about 1 to about 50 amino acid residues (and all
      integer amino acid residues therebetween)

<400> SEQUENCE: 123

Xaa Val Asp Ala Ala Xaa Ala Leu Pro Ala His Xaa Xaa Xaa Gly Arg
1               5                   10                  15

Glu Arg Val Tyr Xaa
            20

<210> SEQ ID NO 124
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: is absent or is selected from at least one of
      a proteinaceous moiety comprising from about 1 to about 50 amino
      acid residues (and all integer amino acid residues therebetween),
      and a protecting moiety
<220> FEATURE:
<221> NAME/KEY: MISC_FEATURE
<222> LOCATION: (4)..(4)
<223> OTHER INFORMATION: is selected from charged amino acid residues,
      or modified forms thereof, and acidic amino acid residues, or
      modified forms thereof, or neutral/polar amino acid residues, or
```

```
      modified forms thereof
<220> FEATURE:
<221> NAME/KEY: MISC_FEATURE
<222> LOCATION: (5)..(5)
<223> OTHER INFORMATION: is selected from neutral/polar amino acid
      residues, or modified forms thereof, or basic amino acid residues,
      or modified forms thereof
<220> FEATURE:
<221> NAME/KEY: MISC_FEATURE
<222> LOCATION: (10)..(10)
<223> OTHER INFORMATION: is selected from any amino acid residue, or
      modified forms thereof, or hydrophobic amino acid residues, or
      modified forms thereof, or acidic amino acid residues, or modified
      forms thereof
<220> FEATURE:
<221> NAME/KEY: MISC_FEATURE
<222> LOCATION: (13)..(13)
<223> OTHER INFORMATION: is selected from basic amino acid residues, or
      modified forms thereof, or neutral/polar amino acid residues, or
      modified forms thereof
<220> FEATURE:
<221> NAME/KEY: MISC_FEATURE
<222> LOCATION: (17)..(17)
<223> OTHER INFORMATION: is selected from neutral/polar amino acid
      residues, or modified forms thereof, or basic amino acid residues,
      or modified forms thereof
<220> FEATURE:
<221> NAME/KEY: MISC_FEATURE
<222> LOCATION: (19)..(19)
<223> OTHER INFORMATION: is selected from acidic amino acid residues, or
      modified forms thereof
<220> FEATURE:
<221> NAME/KEY: MISC_FEATURE
<222> LOCATION: (21)..(21)
<223> OTHER INFORMATION: is absent or is a proteinaceous moiety
      comprising from about 1 to about 50 amino acid residues (and all
      integer amino acid residues therebetween)

<400> SEQUENCE: 124

Xaa Lys Gly Xaa Xaa Tyr Trp Glu Tyr Xaa Phe Gln Xaa Gln Pro Ser
1               5                   10                  15

Xaa Glu Xaa Cys Xaa
            20

<210> SEQ ID NO 125
<211> LENGTH: 27
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: is absent or is selected from at least one of
      a proteinaceous moiety comprising from about 1 to about 50 amino
      acid residues (and all integer amino acid residues therebetween),
      and a protecting moiety
<220> FEATURE:
<221> NAME/KEY: MISC_FEATURE
<222> LOCATION: (3)..(3)
<223> OTHER INFORMATION: is selected from charged amino acid residues,
      or modified forms thereof, and basic amino acid residues, or
      modified forms thereof, or small amino acid residues, or modified
      forms thereof
<220> FEATURE:
<221> NAME/KEY: MISC_FEATURE
<222> LOCATION: (7)..(7)
<223> OTHER INFORMATION: is selected from hydrophobic amino acid
      residues, or modified forms thereof
<220> FEATURE:
<221> NAME/KEY: MISC_FEATURE
<222> LOCATION: (8)..(8)
<223> OTHER INFORMATION: is selected from hydrophobic amino acid
      residues, or modified forms thereof
<220> FEATURE:
<221> NAME/KEY: MISC_FEATURE
<222> LOCATION: (9)..(9)
<223> OTHER INFORMATION: is selected from neutral/polar amino acid
```

```
        residues, or modified forms thereof, or basic amino acid residues,
        or modified forms thereof
<220>   FEATURE:
<221>   NAME/KEY: MISC_FEATURE
<222>   LOCATION: (14)..(14)
<223>   OTHER INFORMATION: is selected from acidic amino acid residues, or
        modified forms thereof, or hydrophobic amino acid residues, or
        modified forms thereof
<220>   FEATURE:
<221>   NAME/KEY: MISC_FEATURE
<222>   LOCATION: (15)..(15)
<223>   OTHER INFORMATION: is selected from acidic amino acid residues, or
        modified forms thereof, or neutral/polar amino acid residues, or
        modified forms thereof
<220>   FEATURE:
<221>   NAME/KEY: MISC_FEATURE
<222>   LOCATION: (18)..(18)
<223>   OTHER INFORMATION: is selected from charged amino acid residues,
        or modified forms thereof, or acidic amino acid residues, or
        modified forms thereof
<220>   FEATURE:
<221>   NAME/KEY: MISC_FEATURE
<222>   LOCATION: (23)..(23)
<223>   OTHER INFORMATION: is selected from small amino acid residues, or
        modified forms thereof
<220>   FEATURE:
<221>   NAME/KEY: MISC_FEATURE
<222>   LOCATION: (24)..(24)
<223>   OTHER INFORMATION: is selected from basic amino acid residues, or
        modified forms thereof, or small amino acid residues, or modified
        forms thereof
<220>   FEATURE:
<221>   NAME/KEY: MISC_FEATURE
<222>   LOCATION: (25)..(25)
<223>   OTHER INFORMATION: is selected from small amino acid residues, or
        modified forms thereof
<220>   FEATURE:
<221>   NAME/KEY: MISC_FEATURE
<222>   LOCATION: (26)..(26)
<223>   OTHER INFORMATION: is selected from small amino acid residues, or
        modified forms thereof, or hydrophobic amino acid residues, or
        modified forms thereof
<220>   FEATURE:
<221>   NAME/KEY: MISC_FEATURE
<222>   LOCATION: (27)..(27)
<223>   OTHER INFORMATION: is absent or is a proteinaceous moiety
        comprising from about 1 to about 50 amino acid residues (and all
        integer amino acid residues therebetween)

<400>   SEQUENCE: 125

Xaa Phe Xaa His Phe Ala Xaa Xaa Xaa Arg Asp Ser Trp Xaa Xaa Ile
1               5                   10                  15

Phe Xaa Leu Leu Phe Trp Xaa Xaa Xaa Xaa Xaa
            20                  25

<210>   SEQ ID NO 126
<211>   LENGTH: 24
<212>   TYPE: PRT
<213>   ORGANISM: Homo sapiens
<220>   FEATURE:
<221>   NAME/KEY: MISC_FEATURE
<222>   LOCATION: (1)..(1)
<223>   OTHER INFORMATION: is absent or is selected from at least one of
        a proteinaceous moiety comprising from about 1 to about 50 amino
        acid residues (and all integer amino acid residues therebetween),
        and a protecting moiety
<220>   FEATURE:
<221>   NAME/KEY: MISC_FEATURE
<222>   LOCATION: (2)..(2)
<223>   OTHER INFORMATION: is selected from small amino acid residues, or
        modified forms thereof
<220>   FEATURE:
<221>   NAME/KEY: MISC_FEATURE
<222>   LOCATION: (3)..(3)
<223>   OTHER INFORMATION: is selected from basic amino acid residues, or
        modified forms thereof, and small amino acid residues, or modified
```

```
            forms thereof
<220> FEATURE:
<221> NAME/KEY: MISC_FEATURE
<222> LOCATION: (4)..(4)
<223> OTHER INFORMATION: is selected from small amino acid residues, or
      modified forms thereof
<220> FEATURE:
<221> NAME/KEY: MISC_FEATURE
<222> LOCATION: (5)..(5)
<223> OTHER INFORMATION: is selected from small amino acid residues, or
      modified forms thereof, or hydrophobic amino acid residues, or
      modified forms thereof
<220> FEATURE:
<221> NAME/KEY: MISC_FEATURE
<222> LOCATION: (6)..(6)
<223> OTHER INFORMATION: is selected from small amino acid residues, or
      modified forms thereof, or acidic amino acid residues, or modified
      forms thereof
<220> FEATURE:
<221> NAME/KEY: MISC_FEATURE
<222> LOCATION: (8)..(8)
<223> OTHER INFORMATION: is selected from small amino acid residues, or
      modified forms thereof
<220> FEATURE:
<221> NAME/KEY: MISC_FEATURE
<222> LOCATION: (9)..(9)
<223> OTHER INFORMATION: is selected from any amino acid residue, or
      modified forms thereof, or hydrophobic amino acid residues, or
      modified forms thereof, or small amino acid residues, or modified
      forms thereof
<220> FEATURE:
<221> NAME/KEY: MISC_FEATURE
<222> LOCATION: (10)..(10)
<223> OTHER INFORMATION: is selected from any amino acid residue, or
      modified forms thereof, or acidic amino acid residues, or modified
      forms thereof, or small amino acid residues, or modified forms
      thereof
<220> FEATURE:
<221> NAME/KEY: MISC_FEATURE
<222> LOCATION: (12)..(12)
<223> OTHER INFORMATION: is selected from neutral/polar amino acid
      residues, or modified forms thereof, or basic amino acid residues,
      or modified forms thereof
<220> FEATURE:
<221> NAME/KEY: MISC_FEATURE
<222> LOCATION: (13)..(13)
<223> OTHER INFORMATION: is selected from hydrophobic amino acid
      residues, or modified forms thereof, and aliphatic amino acid
      residues, or modified forms thereof
<220> FEATURE:
<221> NAME/KEY: MISC_FEATURE
<222> LOCATION: (16)..(16)
<223> OTHER INFORMATION: is selected from basic amino acid residues, or
      modified forms thereof, or neutral/polar amino acid residues, or
      modified forms thereof
<220> FEATURE:
<221> NAME/KEY: MISC_FEATURE
<222> LOCATION: (17)..(17)
<223> OTHER INFORMATION: is selected from acidic amino acid residues, or
      modified forms, or neutral/polar amino acid residues, or modified
      forms thereof
<220> FEATURE:
<221> NAME/KEY: MISC_FEATURE
<222> LOCATION: (19)..(19)
<223> OTHER INFORMATION: is selected from basic amino acid residues, or
      modified forms thereof, or hydrophobic amino acid residues, or
      modified forms thereof, and aromatic amino acid residues, or
      modified forms thereof
<220> FEATURE:
<221> NAME/KEY: MISC_FEATURE
<222> LOCATION: (21)..(21)
<223> OTHER INFORMATION: is selected from hydrophobic amino acid
      residues, or modified forms thereof
<220> FEATURE:
<221> NAME/KEY: MISC_FEATURE
<222> LOCATION: (23)..(23)
<223> OTHER INFORMATION: is selected from small amino acid residues, or
      modified forms thereof, or acidic amino acid residues, or modified
      forms thereof
```

```
<220> FEATURE:
<221> NAME/KEY: MISC_FEATURE
<222> LOCATION: (24)..(24)
<223> OTHER INFORMATION: is absent or is a proteinaceous moiety
      comprising from about 1 to about 50 amino acid residues (and all
      integer amino acid residues therebetween)

<400> SEQUENCE: 126

Xaa Xaa Xaa Xaa Xaa Xaa Gly Xaa Xaa Xaa Pro Xaa Xaa Ile Ser Xaa
1               5                   10                  15

Xaa Trp Xaa Gly Xaa Pro Xaa Xaa
            20

<210> SEQ ID NO 127
<211> LENGTH: 24
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: is absent or is selected from at least one of
      a proteinaceous moiety comprising from about 1 to about 50 amino
      acid residues (and all integer amino acid residues therebetween),
      and a protecting moiety
<220> FEATURE:
<221> NAME/KEY: MISC_FEATURE
<222> LOCATION: (2)..(2)
<223> OTHER INFORMATION: is selected from hydrophobic amino acid
      residues, or modified forms thereof, and aromatic amino acid
      residues, or modified forms thereof
<220> FEATURE:
<221> NAME/KEY: MISC_FEATURE
<222> LOCATION: (3)..(3)
<223> OTHER INFORMATION: is selected from hydrophobic amino acid
      residues, or modified forms thereof, and aromatic amino acid
      residues, or modified forms thereof
<220> FEATURE:
<221> NAME/KEY: MISC_FEATURE
<222> LOCATION: (8)..(8)
<223> OTHER INFORMATION: is selected from small amino acid residues, or
      modified forms thereof, or hydrophobic amino acid residues, or
      modified forms thereof
<220> FEATURE:
<221> NAME/KEY: MISC_FEATURE
<222> LOCATION: (9)..(9)
<223> OTHER INFORMATION: is selected from small amino acid residues, or
      modified forms thereof, or neutral/polar amino acid residues, or
      modified forms thereof
<220> FEATURE:
<221> NAME/KEY: MISC_FEATURE
<222> LOCATION: (10)..(10)
<223> OTHER INFORMATION: is selected from small amino acid residues, or
      modified forms thereof, or hydrophobic amino acid residues, or
      modified forms thereof
<220> FEATURE:
<221> NAME/KEY: MISC_FEATURE
<222> LOCATION: (12)..(12)
<223> OTHER INFORMATION: is selected from small amino acid residues, or
      modified forms thereof
<220> FEATURE:
<221> NAME/KEY: MISC_FEATURE
<222> LOCATION: (13)..(13)
<223> OTHER INFORMATION: is selected from any amino acid residue, or
      modified forms thereof, or acidic amino acid residues, or modified
      forms thereof, or hydrophobic amino acid residues, or modified
      forms thereof
<220> FEATURE:
<221> NAME/KEY: MISC_FEATURE
<222> LOCATION: (15)..(15)
<223> OTHER INFORMATION: is absent or is selected from neutral/polar
      amino acid residues, or modified forms thereof, or hydrophobic
      amino acid residues, or modified forms thereof
<220> FEATURE:
<221> NAME/KEY: MISC_FEATURE
<222> LOCATION: (16)..(16)
<223> OTHER INFORMATION: is selected from acidic amino acid residues, or
```

-continued

```
      modified forms thereof, or hydrophobic amino acid residues, or
      modified forms thereof
<220> FEATURE:
<221> NAME/KEY: MISC_FEATURE
<222> LOCATION: (17)..(17)
<223> OTHER INFORMATION: is selected from any amino acid residues, or
      modified forms thereof, or neutral/polar amino acid residues, or
      modified forms thereof, or small amino acid residues, or modified
      forms thereof
<220> FEATURE:
<221> NAME/KEY: MISC_FEATURE
<222> LOCATION: (18)..(18)
<223> OTHER INFORMATION: is selected from hydrophobic amino acid
      residues, or modified forms thereof
<220> FEATURE:
<221> NAME/KEY: MISC_FEATURE
<222> LOCATION: (19)..(19)
<223> OTHER INFORMATION: is selected from charged amino acid residues,
      or modified forms thereof, or acidic amino acid residues, or
      modified forms thereof
<220> FEATURE:
<221> NAME/KEY: MISC_FEATURE
<222> LOCATION: (20)..(20)
<223> OTHER INFORMATION: is selected from hydrophobic amino acid
      residues, or modified forms thereof, or small amino acid residues,
      or modified forms thereof
<220> FEATURE:
<221> NAME/KEY: MISC_FEATURE
<222> LOCATION: (21)..(21)
<223> OTHER INFORMATION: is selected from any amino acid residues, or
      modified forms thereof, or small amino acid residues, or modified
      forms thereof, or neutral/polar amino acid residues, or modified
      forms thereof
<220> FEATURE:
<221> NAME/KEY: MISC_FEATURE
<222> LOCATION: (24)..(24)
<223> OTHER INFORMATION: is absent or is a proteinaceous moiety
      comprising from about 1 to about 50 amino acid residues (and all
      integer amino acid residues therebetween)

<400> SEQUENCE: 127

Xaa Xaa Xaa Ser Ser Glu Glu Xaa Xaa Xaa Gly Xaa Xaa Asn Xaa Xaa
1               5                   10                  15

Xaa Xaa Xaa Xaa Xaa Trp Leu Xaa
            20

<210> SEQ ID NO 128
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: is absent or is selected from at least one of
      a proteinaceous moiety comprising from about 1 to about 50 amino
      acid residues (and all integer amino acid residues therebetween),
      and a protecting moiety
<220> FEATURE:
<221> NAME/KEY: MISC_FEATURE
<222> LOCATION: (8)..(8)
<223> OTHER INFORMATION: is selected from basic amino acid residues, or
      modified forms thereof, and neutral/polar amino acid residues, or
      modified forms thereof
<220> FEATURE:
<221> NAME/KEY: MISC_FEATURE
<222> LOCATION: (12)..(12)
<223> OTHER INFORMATION: is selected from small amino acid residues, or
      modified forms thereof
<220> FEATURE:
<221> NAME/KEY: MISC_FEATURE
<222> LOCATION: (14)..(14)
<223> OTHER INFORMATION: is selected from any amino acid residue, or
      modified forms thereof, or small amino acid residues, or modified
      forms thereof, or neutral/polar amino acid residues, or modified
      forms thereof, or from hydrophobic amino acid residues, or
      modified forms
```

```
<220> FEATURE:
<221> NAME/KEY: MISC_FEATURE
<222> LOCATION: (21)..(21)
<223> OTHER INFORMATION: is absent or is a proteinaceous moiety
      comprising from about 1 to about 50 amino acid residues (and all
      integer amino acid residues therebetween)

<400> SEQUENCE: 128

Xaa Arg Val Asn Leu Arg Thr Xaa Arg Val Asp Xaa Val Xaa Pro Pro
1               5                   10                  15

Tyr Pro Arg Ser Xaa
                20
```

COMPLEX-FORMATION-MODULATING AGENTS AND USES THEREFOR

This application is a § 371 US National Entry of International Application No. PCT/AU2013/001342, filed Nov. 21, 2013, which claims the benefit of Australian Application No. 2012905085, Nov. 22, 2012.

FIELD OF THE INVENTION

This invention relates generally to methods and agents for modulating proliferation, migration and/or survival of cells. More particularly, the present invention relates to molecules that have any one or more activities selected from: inhibiting binding of vitronectin to at least one vitronectin-binding partner selected from an IGF and IGFBP, inhibiting formation of a complex comprising vitronectin and at least one vitronectin-binding partner selected from an IGF and IGFBP, or inhibiting proliferation or survival of a hyperproliferative cell (e.g., a neoplastic cell or non-neoplastic cell), or inhibiting migration or invasion of a hyperproliferative cell (e.g., a neoplastic cell or a non-neoplastic cell). Additionally, the present invention relates to the use of these molecules in methods and compositions for treating or preventing hyperproliferative cell disorders including neoplastic (e.g., cancers such as epithelial cancers) and non-neoplastic disorders.

Bibliographic details of various citations referred to by author in the present specification are listed at the end of the description.

RELATED APPLICATION

This application claims priority to Australian Provisional Application No. 2012905085, entitled "Complex-Formation-Modulating Agents and Uses Therefor", filed on 22 Nov. 2012, the subject matter of which is incorporated herein by reference in its entirety.

BACKGROUND OF THE INVENTION

The ability of cells to invade and migrate from the primary tumor site and subsequently survive within distal microenvironments forms the basic mechanisms underlying cancer progression and are the major cause of cancer-related morbidity and mortality. Altered interactions between mitogenic hormones, growth factors, and the extracellular matrix (ECM) are considered to be among the more important factors contributing to cancer progression (Beattie et al., 2010). One such growth factor family is the insulin-like growth factor (IGF) system, members of which have well documented roles in the development and progression of numerous malignancies, including breast cancer (Annunziata et al., 2011; Fox et al., 2011). The IGFs are also tightly regulated by a family of specific binding proteins, termed insulin like growth factor binding proteins (IGFBPs; IGFBPs 1-6), whose primary role is to bind free IGFs and thereby moderate their half-life, specificity and activity. The IGF system includes the IGF receptor type-1 (IGF-1R) which is a transmembrane receptor with tyrosine kinase activity. IGF-1R mediates proliferation when activated by the stimulatory ligands IGF-I and IGF-II (Dupont and LeRoith, 2001). The insulin receptor is also a key component of the IGF signaling pathway. Although the classic insulin receptor isoform-B (IR-B) binds only insulin and elicits insulin-related metabolic effects, insulin receptor isoform-A (IR-A) binds IGF-II in addition to insulin and initiates mitogenic signaling (Pandini et al., 2002). An important feature of the IGF system, including the expression of IGF-1R, is its ubiquitous presence in most carcinomas (Boone and Lee, 2012). For example, in breast cancer, IGF-1R expression is found in nearly 90% of tumors (Bonneterre et al., 1990; Nielsen et al., 2004), with over expression of IGF-1R observed in 44% of breast cancer tissue specimens (Shimizu et al., 2004). Apart from increased expression levels, the role of IGF-1R signaling in malignant transformation and in tumor cell proliferation makes it an attractive therapeutic target.

There have been several reports, both in vitro and in vivo, targeting IGF-1R activation using various strategies, including antisense technology (Schillaci et al., 2006), dominant negative IGF-1R (Sachdev et al., 2004), small molecule chemical inhibitors (Blum et al., 2003; Garcia-Echeverria et al., 2004; Haluska et al., 2006) and inhibitory antibodies, an approach most frequently used (Sachdev et al., 2003; Cohen et al., 2005). Indeed, more than 70 clinical trials across 30 candidate drugs have been tested, with a few currently progressing through phase-II, in a wide variety of human malignancies (Gombos et al., 2012). Most trials have used antibodies and small molecule inhibitors for the therapeutic blockade of IGF-1R including the fully human monoclonal antibodies cixutumumab (ImClone) and AMG-479 (Amgen). The IGF-1R antagonizing monoclonal antibodies currently used are very specific owing to the specific epitope recognition within the IGF-1R and demonstrate no binding to the insulin receptor. This is designed to overcome concerns of the off-target induction of insulin resistance and hyperglycemia driven by cross-targeting the IR-B (Haluska et al., 2007). However, monoclonal antibodies targeting only the IGF-1R will have no inhibitory effects on IR-A-mediated signaling. This could be a potential liability if IR-A or Hybrid IGF-1R/IR receptor (HyR)-mediated signaling can overcome the IGF-1R blockade (Pandini et al., 2002), given that excess circulating levels of IGF-I and IGF-II can signal through IR-A or HyR after anti-IGF-1R therapy (Huang et al., 2009). This could be potentially subverted by the use of tyrosine kinase inhibitors which are currently in clinical and preclinical development (e.g., BMS-536924 and BMS-554417 (Bristol-Myers Squibb)). A particular disadvantage of tyrosine kinase inhibitors is that these therapies indiscriminately inhibit the kinase domains of all IGF system receptors, including the IR-A and -B, since the primary sequences of IGF-1R and IRs share near absolute conservation in the kinase domains (Munshi et al., 2003). In spite of their advantages of potentially inhibiting the IR-A-mediated compensatory effects on IGF-1R blockade, these broad spectrum inhibitors will also inhibit the IR-B receptor which may represent a significant liability on insulin metabolism. Recently, a few tyrosine kinase inhibitors have been developed, namely NVP-AEW541 and NVP-ADW742 (Novartis), and BVP.51004 (Biovitrium) that have been shown in cellular assays to selectively inhibit only IGF-1R kinases and not the IR kinases. Nevertheless, no clinical data are available on these inhibitors to date. Furthermore, no therapies yet exist in the clinic that can demonstrate the combined benefits of IGF-1R-specific and tyrosine kinase therapies. In summary, current therapies are associated with insulin resistance or IR-A-mediated compensations seen in the IGF-1R-specific therapies, or disregulated insulin metabolism seen in the broad-spectrum tyrosine kinase therapies.

Hence, there is a need to develop novel modulators that block the activation of the tumorigenic receptors within the IGF system whilst simultaneously permitting the normal insulin signaling to occur through the IR-B receptor.

SUMMARY OF THE INVENTION

The present invention is based in part on a novel strategy for targeting the accessibility of IGF-I and IGF-II to receptors (e.g., IGF-1R, IR-A and Hybrid-Receptors) of the IGF system to thereby inhibit activation of these receptors and at the same time allow for insulin signaling to occur through the IR-B receptor. In accordance with the present invention this is achieved through the use of peptide antagonist compounds that inhibit binding of a vitronectin to at least one vitronectin-binding partner selected from an IGF (e.g., IGF-I and IGF-II) and an IGFBP (e.g., IGFBP-3 and IGFBP-5) and/or that inhibit formation of a complex comprising a vitronectin and at least one vitronectin-binding partner selected from an IGF (e.g., IGF-I and IGF-II) and an IGFBP (e.g., IGFBP-3 and IGFBP-5). These compounds find utility in a range of applications including inter alia ones that require inhibition of migration, proliferation and/or survival of cells associated with hyperproliferative cell conditions or disorders, as described hereafter.

Accordingly, in one aspect, the present invention provides isolated or purified proteinaceous molecules that are fragments of vitronectin and that have at least one activity selected from: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

In related aspects, the present invention provides isolated or purified proteinaceous molecules that consist or consist essentially of an amino acid sequence represented by any one of formulae I-VIII:

$$CQCDELCX_1YYQSCCX_2DX_3X_4X_5 \text{ [SEQ ID NO:113]} \quad (I)$$

wherein:
$X_1$ is selected from small amino acid residues such as S or T, or modified forms thereof;
$X_2$ is selected from small amino acid residues such as T or A, or modified forms thereof, or hydrophobic amino acid residues including aliphatic amino acid residues such as V, or modified forms thereof;
$X_3$ is selected from hydrophobic amino acid residues including aromatic amino acid residues such as Y or F, or modified forms thereof;
$X_4$ is selected from small amino acid residues such as T or A, or modified forms thereof, or hydrophobic amino acid residues including aliphatic amino acid residues such as M or V, or modified forms thereof; and
$X_5$ is selected from small amino acid residues such as A, or modified forms thereof, or acidic amino acid residues such as E, or modified forms thereof, $$TX_1X_2X_3GX_4X_5X_6 \text{ [SEQ ID NO:114]} \quad (II)$$

wherein:
$X_1$ is selected from any amino acid residue including for example acidic amino acid residues such as D, or modified forms thereof, or small amino acid residues such as S or T, or modified forms thereof, or hydrophobic amino acid residues including aliphatic amino acid residues such as L, or modified forms thereof;
$X_2$ is selected from charged amino acid residues including basic amino acid residues such as H, or modified forms thereof, or acidic amino acid residues such as D or E, or modified forms thereof;
$X_3$ is selected from any amino acid residue including for example small amino acid residues such as P, or modified forms thereof, or hydrophobic amino acid residues including aliphatic amino acid residues such as L, or modified forms thereof, or neutral/polar amino acid residues such as Q, or modified forms thereof, or acidic amino acid residues such as E, or modified forms thereof;
$X_4$ is selected from any amino acid residue including for example basic amino acid residues such as R, or modified forms thereof, or hydrophobic amino acid residues including aliphatic amino acid residues such as V, or modified forms thereof, or small amino acid residues such as T, or modified forms thereof;
$X_5$ is selected from small amino acid residues such as P or S, or modified forms thereof; and
$X_6$ is selected from any amino acid residue including for example neutral/polar amino acid residues such as Q, or modified forms thereof, or acidic amino acid residues such as E, or modified forms thereof, or small amino acid residues such as A, or modified forms thereof, $$VDAAX_1ALPAHX_2X_3X_4GRERVY \text{ [SEQ ID NO:115]} \quad (III)$$

wherein:
$X_1$ is selected from hydrophobic amino acid residues including aliphatic amino acid residues such as L, or modified forms thereof, and aromatic amino acid residues such as F, or modified forms thereof;
$X_2$ is selected from any amino acid residue including for example small amino acid residues such as S, or modified forms thereof, or neutral/polar amino acid residues such as N, or modified forms thereof, or basic amino acid residues such as R, or modified forms thereof;
$X_3$ is selected from hydrophobic amino acid residues including aromatic amino acid residues such as Y or F, or modified forms thereof; and
$X_4$ is selected from small amino acid residues such as S, or modified forms thereof, or neutral/polar amino acid residues such as N, or modified forms thereof, $$KGX_1X_2YWEYX_3FQX_4QPSX_5EX_6C \text{ [SEQ ID NO:116]} \quad (IV)$$

wherein:
X$_1$ is selected from charged amino acid residues including basic amino acid residues such as K or modified forms thereof, and acidic amino acid residues such as D, or modified forms thereof, or neutral/polar amino acid residues such as N, or modified forms thereof;
X$_2$ is selected from neutral/polar amino acid residues such as Q, or modified forms thereof, or basic amino acid residues such as H or K, or modified forms thereof;
X$_3$ is selected from any amino acid residue including for example neutral/polar amino acid residues such as Q, or modified forms thereof, or hydrophobic amino acid residues including aliphatic amino acid residues such as V, or modified forms thereof, or acidic amino acid residues such as E, or modified forms thereof;
X$_4$ is selected from basic amino acid residues such as H, or modified forms thereof, or neutral/polar amino acid residues such as Q, or modified forms thereof;
X$_5$ is selected from neutral/polar amino acid residues such as Q, or modified forms thereof, or basic amino acid residues such as R, or modified forms thereof; and
X$_6$ is selected from acidic amino acid residues such as E or D, or modified forms thereof, FX$_1$HFAX$_2$X$_3$X$_4$RDSWX$_5$X$_6$IFX$_7$LLFWX$_8$X$_9$X$_{10}$X$_{11}$ [SEQ ID NO:117]  (V)

wherein:
X$_1$ is selected from charged amino acid residues including acidic amino acid residues such as E, or modified forms thereof, and basic amino acid residues such as K or modified forms thereof, or small amino acid residues such as A, or modified forms thereof;
X$_2$ is selected from hydrophobic amino acid residues including aliphatic amino acid residues such as M or L, or modified forms thereof;
X$_3$ is selected from hydrophobic amino acid residues including aliphatic amino acid residues such as M or L, or modified forms thereof;
X$_4$ is selected from neutral/polar amino acid residues such as Q, or modified forms thereof, or basic amino acid residues such H, or modified forms thereof;
X$_5$ is selected from acidic amino acid residues such as E, or modified forms thereof, or hydrophobic amino acid residues including aliphatic amino acid residues such as V or modified forms thereof;
X$_6$ is selected from acidic amino acid residues such as D, or modified forms thereof, or neutral/polar amino acid residues such as N, or modified forms thereof;
X$_7$ is selected from charged amino acid residues including basic amino acid residues such as R or K or modified forms thereof, or acidic amino acid residues such as E, or modified forms thereof;
X$_8$ is selected from small amino acid residues such as G or S, or modified forms thereof;
X$_9$ is selected from basic amino acid residues such R or H, or modified forms thereof, or small amino acid residues such as G, or modified forms thereof;
X$_{10}$ is selected from small amino acid residues such as T, S or P, or modified forms thereof, and
X$_{11}$ is selected from small amino acid residues such as S, or modified forms thereof, or hydrophobic amino acid residues including aromatic amino acid residues such as F or Y, or modified forms thereof X$_1$X$_2$X$_3$X$_4$X$_5$GX$_6$X$_7$X$_8$PX$_9$X$_{10}$ISX$_{11}$X$_{12}$WX$_{13}$GX$_{14}$PX$_{15}$ [SEQ ID NO:118]  (VI)

wherein:
X$_1$ is selected from small amino acid residues such as G or S, or modified forms thereof;
X$_2$ is selected from basic amino acid residues such as R or H, or modified forms thereof, and small amino acid residues such as G, or modified forms thereof;
X$_3$ is selected from small amino acid residues such as T, S or P, or modified forms thereof;
X$_4$ is selected from small amino acid residues such as S, or modified forms thereof, or hydrophobic amino acid residues including aromatic amino acid residues such as F or Y, or modified forms thereof;
X$_5$ is selected from small amino acid residues such as A or G, or modified forms thereof, or acidic amino acid residues such as D, or modified forms thereof;
X$_6$ is selected from small amino acid residues such as T or A, or modified forms thereof;
X$_7$ is selected from any amino acid residue including for example basic amino acid residues such as R or K, or modified forms thereof, or hydrophobic amino acid residues including aliphatic amino acid residues such as I, or modified forms thereof, or small amino acid residues such as G, or modified forms thereof;
X$_8$ is selected from any amino acid residue including for example neutral/polar amino acid residues such as Q, or modified forms thereof, or acidic amino acid residues such E, or modified forms thereof, or small amino acid residues such as G, or modified forms thereof;
X$_9$ is selected from neutral/polar amino acid residues such as Q, or modified forms thereof, or basic amino acid residues such R, or modified forms thereof;
X$_{10}$ is selected from hydrophobic amino acid residues including aromatic amino acid residues such as F, or modified forms thereof, and aliphatic amino acid residues such as V or L, or modified forms thereof;
X$_{11}$ is selected from basic amino acid residues such R, or modified forms thereof, or neutral/polar amino acid residues such as Q, or modified forms thereof;
X$_{12}$ is selected from acidic amino acid residues such D, or modified forms, or neutral/polar amino acid residues such as N, or modified forms thereof;
X$_{13}$ is selected from basic amino acid residues such as H, or modified forms thereof, or hydrophobic amino acid residues including aliphatic amino acid residues such as L, or modified forms thereof, and aromatic amino acid residues such as F, or modified forms thereof;
X$_{14}$ is selected from hydrophobic amino acid residues including aliphatic amino acid residues such as V or L, or modified forms thereof, and
X$_{15}$ is selected from small amino acid residues such as G, or modified forms thereof, or acidic amino acid residues such E, or modified forms thereof.

X$_1$X$_2$SSEEX$_3$X$_4$X$_5$GX$_6$X$_7$NX$_8$X$_9$X$_{10}$X$_{11}$X$_{12}$X$_{13}$X$_{14}$WL [SEQ ID NO:119]  (VII)

wherein:
X$_1$ is selected from hydrophobic amino acid residues including aliphatic amino acid residues such as L, or modified forms thereof, and aromatic amino acid residues such as W, or modified forms thereof;
X$_2$ is selected from hydrophobic amino acid residues including aliphatic amino acid residues such as L, or modified forms thereof, and aromatic amino acid residues such as F, or modified forms thereof;
X$_3$ is selected from small amino acid residues such as S or T, or modified forms thereof, or hydrophobic amino acid residues including aliphatic amino acid residues such as L or V, or modified forms thereof;

$X_4$ is selected from small amino acid residues such as G or S, or modified forms thereof, or neutral/polar amino acid residues such as N, or modified forms thereof, $X_5$ is selected from small amino acid residues such as P, or modified forms thereof, or hydrophobic amino acid residues including aliphatic amino acid residues such as L, or modified forms thereof, $X_6$ is selected from small amino acid residues such as P, A, G or T, or modified forms thereof;

$X_7$ is selected from any amino acid residue including for example neutral/polar amino acid residues such as N, or modified forms thereof, or acidic amino acid residues such as D, or modified forms thereof, or hydrophobic amino acid residues including aromatic amino acid residues such as Y, or modified forms thereof;

$X_8$ is absent or is selected from neutral/polar amino acid residues such as N, or modified forms thereof, or hydrophobic amino acid residues including aromatic amino acid residues such Y, or modified forms thereof;

$X_9$ is selected from acidic amino acid residues such as E or D, or modified forms thereof, or hydrophobic amino acid residues including aromatic amino acid residues such as Y, or modified forms thereof;

$X_{10}$ is selected from any amino acid residues including acidic amino acid residues such as D, or modified forms thereof, or neutral/polar amino acid residues such as N, or modified forms thereof, or small amino acid residues such as S, or modified forms thereof;

$X_{11}$ is selected from hydrophobic amino acid residues including aromatic amino acid residues such as Y or F, or modified forms thereof;

$X_{12}$ is selected from charged amino acid residues including basic amino acid residues such as K or R, or modified forms thereof, or acidic amino acid residues such as E or D, or modified forms thereof;

$X_{13}$ is selected from hydrophobic amino acid residues including aliphatic amino acid residues such as M, or modified forms thereof, or small amino acid residues such as T, or modified forms thereof; and $X_{14}$ is selected from any amino acid residues including acidic amino acid residues such as D, or modified forms thereof, or small amino acid residues such as S, or modified forms thereof, or neutral/polar amino acid residues such as N, or modified forms thereof, $$RVNLRTX_1RVDX_2VX_3PPYPRS \text{ [SEQ ID NO:120]} \quad (VIII)$$

wherein:

$X_1$ is selected from basic amino acid residues such as R, or modified forms thereof, and neutral/polar amino acid residues such as Q, or modified forms thereof;

$X_2$ is selected from small amino acid residues such as S, A or T, or modified forms thereof; and $X_3$ is selected from any amino acid residue including for example acidic amino acid residues such as D, or modified forms thereof, or small amino acid residues such as T, or modified forms thereof, or neutral/polar amino acid residues such as N, or modified forms thereof, or from hydrophobic amino acid residues including aliphatic amino acid residues such as I, or modified forms thereof;

In some embodiments, the proteinaceous molecules are represented by formula IX:

$$Z_1CQCDELCX_1YYQSCCX_2DX_3X_4X_5Z_2 \text{[SEQ ID NO:121]} \quad (IX)$$

wherein:

$X_1$-$X_5$ are as broadly defined above for formula I;

$Z_1$ is absent or is selected from at least one of a proteinaceous moiety comprising from about 1 to about 50 amino acid residues (and all integer amino acid residues therebetween), and a protecting moiety; and $Z_2$ is absent or is a proteinaceous moiety comprising from about 1 to about 50 amino acid residues (and all integer amino acid residues therebetween).

In some embodiments, the proteinaceous molecules are represented by formula X:

$$Z_1TX_1X_2X_3GX_4X_5X_6Z_2 \text{ [SEQ ID NO:122]} \quad (X)$$

wherein:

$X_1$-$X_6$ are as broadly defined above for formula II;

$Z_1$ is absent or is selected from at least one of a proteinaceous moiety comprising from about 1 to about 50 amino acid residues (and all integer amino acid residues therebetween), and a protecting moiety; and $Z_2$ is absent or is a proteinaceous moiety comprising from about 1 to about 50 amino acid residues (and all integer amino acid residues therebetween).

In some embodiments, the proteinaceous molecules are represented by formula XI:

$$Z_1VDAAX_1ALPAHX_2X_3X_4GRERVYZ_2 \text{ [SEQ ID NO:123]} \quad (XI)$$

wherein:

$X_1$-$X_4$ are as broadly defined above for formula III;

$Z_1$ is absent or is selected from at least one of a proteinaceous moiety comprising from about 1 to about 50 amino acid residues (and all integer amino acid residues therebetween), and a protecting moiety; and $Z_2$ is absent or is a proteinaceous moiety comprising from about 1 to about 50 amino acid residues (and all integer amino acid residues therebetween).

In some embodiments, the proteinaceous molecules are represented by formula XII:

$$Z_1KGX_1X_2YWEYX_3FQX_4QPSX_5EX_6CZ_2 \text{ [SEQ ID NO:124]} \quad (XII)$$

wherein:

$X_1$-$X_6$ are as broadly defined above for formula IV;

$Z_1$ is absent or is selected from at least one of a proteinaceous moiety comprising from about 1 to about 50 amino acid residues (and all integer amino acid residues therebetween), and a protecting moiety; and $Z_2$ is absent or is a proteinaceous moiety comprising from about 1 to about 50 amino acid residues (and all integer amino acid residues therebetween).

In some embodiments, the proteinaceous molecules are represented by formula XIII:

$$Z_1FX_1HFAX_2X_3X_4RDSWX_5X_6IFX_7LLFWX_8X_9X_{10}X_{11}Z_2 \text{ [SEQ ID NO:125]} \quad (XIII)$$

wherein:

$X_1$-$X_{11}$ are as broadly defined above for formula V;

$Z_1$ is absent or is selected from at least one of a proteinaceous moiety comprising from about 1 to about 50 amino acid residues (and all integer amino acid residues therebetween), and a protecting moiety; and $Z_2$ is absent or is a proteinaceous moiety comprising from about 1 to about 50 amino acid residues (and all integer amino acid residues therebetween).

In some embodiments, the proteinaceous molecules are represented by formula XIV:

$$Z_1X_1X_2X_3X_4X_5GX_6X_7X_8PX_9X_{10}ISX_{11}X_{12}WX_{13}GX_{14}PX_{15}Z_2 \text{ [SEQ ID NO:126]} \quad (XIV)$$

wherein:

$X_1$-$X_{15}$ are as broadly defined above for formula VI;

$Z_1$ is absent or is selected from at least one of a proteinaceous moiety comprising from about 1 to about 50 amino acid residues (and all integer amino acid residues therebetween), and a protecting moiety; and $Z_2$ is absent or is a proteinaceous moiety comprising from about 1 to about 50 amino acid residues (and all integer amino acid residues therebetween).

In some embodiments, the proteinaceous molecules are represented by formula XV:

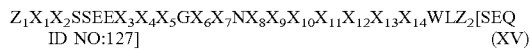
$$Z_1X_1X_2SSEEX_3X_4X_5GX_6X_7NX_8X_9X_{10}X_{11}X_{12}X_{13}X_{14}WLZ_2 \text{[SEQ ID NO:127]} \quad (XV)$$

wherein:

$X_1$-$X_{14}$ are as broadly defined above for formula VII;

$Z_1$ is absent or is selected from at least one of a proteinaceous moiety comprising from about 1 to about 50 amino acid residues (and all integer amino acid residues therebetween), and a protecting moiety; and $Z_2$ is absent or is a proteinaceous moiety comprising from about 1 to about 50 amino acid residues (and all integer amino acid residues therebetween).

In some embodiments, the proteinaceous molecules are represented by formula XVI:

$$Z_1RVNLRTX_1RVDX_2VX_3PPYPRSZ_2 \text{[SEQ ID NO:128]} \quad (XVI)$$

wherein:

$X_1$-$X_3$ are as broadly defined above for formula VIII;

$Z_1$ is absent or is selected from at least one of a proteinaceous moiety comprising from about 1 to about 50 amino acid residues (and all integer amino acid residues therebetween), and a protecting moiety; and $Z_2$ is absent or is a proteinaceous moiety comprising from about 1 to about 50 amino acid residues (and all integer amino acid residues therebetween).

In illustrative examples, the proteinaceous molecules consist or consists essentially of an amino acid sequence (also referred to herein as "class I amino acid sequence") selected from the group consisting of:

(a) an amino acid sequence selected from: CQCDELCSYYQSCCTDYTA [SEQ ID NO:2, from human vitronectin]; CQCDELCSYYQSCCTDYVA [SEQ ID NO:4, from pig vitronectin]; CQCDELCSYYQSCCADFMA [SEQ ID NO:6, from bovine vitronectin]; CQCDELCSYYQSCCADFMA [SEQ ID NO:8, from goat vitronectin]; CQCDELCTYYQSCCADYME [SEQ ID NO:10, from mouse vitronectin]; CQCDELCSYYQSCCADYAA [SEQ ID NO:12, from rabbit vitronectin]; and CQCDELCTYYQSCCVDYME [SEQ ID NO:14, from rat vitronectin];

(b) an amino acid sequence that shares at least 60% (and at least 61% to at least 99% and all integer percentages in between) sequence similarity or sequence identity with the sequence set forth in any one of SEQ ID NO: 2, 4, 6, 8, 10, 12 or 14; or (c) an amino acid sequence which is encoded by the nucleotide sequence set forth in any one of SEQ ID NO:1 (nucleotide sequence encoding SEQ ID NO:2), SEQ ID NO:3 (nucleotide sequence encoding SEQ ID NO:4), SEQ ID NO:5 (nucleotide sequence encoding SEQ ID NO:6), SEQ ID NO:7 (nucleotide sequence encoding SEQ ID NO:8), SEQ ID NO:9 (nucleotide sequence encoding SEQ ID NO:10), SEQ ID NO:11 (nucleotide sequence encoding SEQ ID NO:12) or SEQ ID NO:13 (nucleotide sequence encoding SEQ ID NO:14);

(d) an amino acid sequence which is encoded by a nucleotide sequence that shares at least 60% (and at least 61% to at least 99% and all integer percentages in between) sequence identity with the sequence set forth in any one of SEQ ID NO: 1, 3, 5, 7, 9, 11 or 13, or a complement thereof; or (e) an amino acid sequence which is encoded by a nucleotide sequence that hybridizes under at least medium stringency conditions to the sequence set forth in any one of SEQ ID NO: 1, 3, 5, 7, 9, 11 or 13, or a complement thereof, wherein the amino acid sequence of (a), (b), (c), (d) or (e) has any one or more activities selected from the group consisting of: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

In other illustrative examples, the proteinaceous molecules consist or consists essentially of an amino acid sequence (also referred to herein as a "class II amino acid sequence") selected from the group consisting of:

(a) an amino acid sequence selected from: TLHPGRPQ [SEQ ID NO:16, from human vitronectin]; TDDLGVPE [SEQ ID NO:18, from pig vitronectin]; TSDLGTSE [SEQ ID NO:20, from bovine vitronectin]; TSDLGTSE [SEQ ID NO:22, from goat vitronectin]; TTDQGTPE [SEQ ID NO:24, from mouse vitronectin]; TTELGTSA [SEQ ID NO:26, from rabbit vitronectin]; and TTDEGTSE [SEQ ID NO:28, from rat vitronectin];

(b) an amino acid sequence that shares at least 60% (and at least 61% to at least 99% and all integer percentages in between) sequence similarity or sequence identity with the sequence set forth in any one of SEQ ID NO: 14, 16, 18, 20, 22, 24, 26 or 28; or (c) an amino acid sequence which is encoded by the nucleotide sequence set forth in any one of SEQ ID NO:15 (nucleotide sequence encoding SEQ ID NO:16), SEQ ID NO:17 (nucleotide sequence encoding SEQ ID NO:18), SEQ ID NO:19 (nucleotide sequence encoding SEQ ID NO:20), SEQ ID NO:21 (nucleotide sequence encoding SEQ ID NO:22), SEQ ID NO:23 (nucleotide sequence encoding SEQ ID NO:24), SEQ ID NO:25 (nucleotide sequence encoding SEQ ID NO:26) or SEQ ID NO:27 (nucleotide sequence encoding SEQ ID NO:28);

(d) an amino acid sequence which is encoded by a nucleotide sequence that shares at least 60% (and at least 61% to at least 99% and all integer percentages in between)

sequence identity with the sequence set forth in any one of SEQ ID NO: 15, 17, 19, 21, 23, 25 or 27, or a complement thereof; or (e) an amino acid sequence which is encoded by a nucleotide sequence that hybridizes under at least medium stringency conditions to the sequence set forth in any one of SEQ ID NO: 15, 17, 19, 21, 23, 25 or 27, or a complement thereof, wherein the amino acid sequence of (a), (b), (c), (d) or (e) has any one or more activities selected from the group consisting of: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (5) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

In still other illustrative examples, the proteinaceous molecules consist or consists essentially of an amino acid sequence (also referred to herein as a "class III amino acid sequence") selected from the group consisting of:

(a) an amino acid sequence selected from: VDAALALPAHSYSGRERVY [SEQ ID NO:30, from human vitronectin]; VDAALALPAHSYSGRERVY [SEQ ID NO:32, from pig vitronectin]; VDAALALPAHNFNGRERVY [SEQ ID NO:34, from bovine vitronectin]; VDAALALPAHSYNGRERVY [SEQ ID NO:36, from goat vitronectin]; VDAAFALPAHRYSGRERVY [SEQ ID NO:38, from mouse vitronectin]; VDAAFALPAHSYSGRERVY [SEQ ID NO:40, from rabbit vitronectin]; and VDAALALPAHSYSGRERVY [SEQ ID NO:42, from rat vitronectin];

(b) an amino acid sequence that shares at least 60% (and at least 61% to at least 99% and all integer percentages in between) sequence similarity or sequence identity with the sequence set forth in any one of SEQ ID NO: 30, 32, 34, 36, 38 40 or 42; or (c) an amino acid sequence which is encoded by the nucleotide sequence set forth in any one of SEQ ID NO:29 (nucleotide sequence encoding SEQ ID NO:30), SEQ ID NO:31 (nucleotide sequence encoding SEQ ID NO:32), SEQ ID NO:33 (nucleotide sequence encoding SEQ ID NO:34), SEQ ID NO:35 (nucleotide sequence encoding SEQ ID NO:36), SEQ ID NO:37 (nucleotide sequence encoding SEQ ID NO:38), SEQ ID NO:39 (nucleotide sequence encoding SEQ ID NO:40) or SEQ ID NO:41 (nucleotide sequence encoding SEQ ID NO:42)

(d) an amino acid sequence which is encoded by a nucleotide sequence that shares at least 60% (and at least 61% to at least 99% and all integer percentages in between) sequence identity with the sequence set forth in any one of SEQ ID NO: 29, 31, 33, 35, 37, 39 or 41, or a complement thereof; or (e) an amino acid sequence which is encoded by a nucleotide sequence that hybridizes under at least medium stringency conditions to the sequence set forth in any one of SEQ ID NO: 29, 31, 33, 35, 37, 39 or 41, or a complement thereof, wherein the amino acid sequence of (a), (b), (c), (d) or (e) has any one or more activities selected from the group consisting of: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

In still other illustrative examples, the proteinaceous molecules consist or consists essentially of an amino acid sequence (also referred to herein as a "class IV amino acid sequence") selected from the group consisting of:

(a) an amino acid sequence selected from: KGKQYWEYQFQHQPSQEEC [SEQ ID NO:44, from human vitronectin]; KGKQYWEYVFQQQPSREEC [SEQ ID NO:46, from pig vitronectin]; KGNHYWEYVFQQQPSQEDC [SEQ ID NO:48, from bovine vitronectin]; KGNHYWEYVFQQQPSREEC [SEQ ID NO:50, from goat vitronectin]; KGKQYWEYEFQQQPSQEEC [SEQ ID NO:52, from mouse vitronectin]; KGDKYWEYQFQQQPSQEEC [SEQ ID NO:54, from rabbit vitronectin]; and KGKQYWEYEFQQQPSQEEC [SEQ ID NO:56, from rat vitronectin];

(b) an amino acid sequence that shares at least 60% (and at least 61% to at least 99% and all integer percentages in between) sequence similarity or sequence identity with the sequence set forth in any one of SEQ ID NO: 44, 46, 48, 50, 52, 54 or 56; or (c) an amino acid sequence which is encoded by the nucleotide sequence set forth in any one of SEQ ID NO:43 (nucleotide sequence encoding SEQ ID NO:44), SEQ ID NO:45 (nucleotide sequence encoding SEQ ID NO:46), SEQ ID NO:47 (nucleotide sequence encoding SEQ ID NO:48), SEQ ID NO:49 (nucleotide sequence encoding SEQ ID NO:50), SEQ ID NO:51 (nucleotide sequence encoding SEQ ID NO:52), SEQ ID NO:53 (nucleotide sequence encoding SEQ ID NO:54) or SEQ ID NO:55 (nucleotide sequence encoding SEQ ID NO:56);

(d) an amino acid sequence which is encoded by a nucleotide sequence that shares at least 60% (and at least 61% to at least 99% and all integer percentages in between) sequence identity with the sequence set forth in any one of SEQ ID NO: 43, 45, 47, 49, 51, 53 or 55, or a complement thereof; or (e) an amino acid sequence which is encoded by a nucleotide sequence that hybridizes under at least medium stringency conditions to the sequence set forth in any one of SEQ ID NO: 43, 45, 47, 49, 51, 53 or 55, or a complement thereof, wherein the amino acid sequence of (a), (b), (c), (d) or (e) has any one or more activities selected from the group consisting of: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

In other illustrative examples, the proteinaceous molecules consist or consists essentially of an amino acid sequence (also referred to herein as a "class V amino acid sequence") selected from the group consisting of:

(a) an amino acid sequence selected from: FEHFAMMQRDSWEDIFELLFWGRTS [SEQ ID NO:58, from human vitronectin]; FAHFALMQRDSWEDIFRLLFWSHSF [SEQ ID NO:60, from pig vitronectin]; FKHFALMQRDSWVDIFRLLFWGGSY [SEQ ID NO:62, from bovine vitronectin]; FKHFALMQRDSWEDIFRLLFWGGSF [SEQ ID NO:64, from goat vitronectin]; FEHFALLQRDSWENIFELLFWGRSS [SEQ ID NO:66, from mouse vitronectin]; FEHFAMLHRDSWEDIFKLLFWGRPS [SEQ ID NO:68, from rabbit vitronectin]; and FEHFALLQRDSWENIFELLFWGRSS [SEQ ID NO:70, from rat vitronectin];

(b) an amino acid sequence that shares at least 60% (and at least 61% to at least 99% and all integer percentages in between) sequence similarity or sequence identity with the sequence set forth in any one of SEQ ID NO: 58, 60, 62, 64, 66, 68 or 70; or (c) an amino acid sequence which is encoded by the nucleotide sequence set forth in any one of SEQ ID NO:57 (nucleotide sequence encoding SEQ ID NO:58), SEQ ID NO:59 (nucleotide sequence encoding SEQ ID NO:60), SEQ ID NO:61 (nucleotide sequence encoding SEQ ID NO:62), SEQ ID NO:63 (nucleotide sequence encoding SEQ ID NO:64), SEQ ID NO:65 (nucleotide sequence encoding SEQ ID NO:66), SEQ ID NO:67 (nucleotide sequence encoding SEQ ID NO:68) or SEQ ID NO:69 (nucleotide sequence encoding SEQ ID NO:70);

(d) an amino acid sequence which is encoded by a nucleotide sequence that shares at least 60% (and at least 61% to at least 99% and all integer percentages in between) sequence identity with the sequence set forth in any one of SEQ ID NO: 57, 61, 63, 65, 67 or 69, or a complement thereof; or (e) an amino acid sequence which is encoded by a nucleotide sequence that hybridizes under at least medium stringency conditions to the sequence set forth in any one of SEQ ID NO: 57, 61, 63, 65, 67 or 69, or a complement thereof, wherein the amino acid sequence of (a), (b), (c), (d) or (e) has any one or more activities selected from the group consisting of: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

In still other illustrative examples, the proteinaceous molecules consist or consists essentially of an amino acid sequence (also referred to herein as a "class VI amino acid sequence") selected from the group consisting of:

(a) an amino acid sequence selected from: GRTSAGTRQPQFISRDWHGVPG [SEQ ID NO:72, from human vitronectin]; SHSFGGAIEPRVISQDWLGLPE [SEQ ID NO:74, from pig vitronectin]; GGSYGGAGQPQLISRNWFGLPG [SEQ ID NO:76, from bovine vitronectin]; GGSFGGAGQPQLISRDWFGLPG [SEQ ID NO:78, from goat vitronectin]; GRSSDGAREPQFISRNWHGVPG [SEQ ID NO:80, from mouse vitronectin]; GRPSGGARQPQFISRDWHGVPG [SEQ ID NO:82, from rabbit vitronectin]; and GRSSDGAKGPQFISRDWHGVPG [SEQ ID NO:84, from rat vitronectin];

(b) an amino acid sequence that shares at least 60% (and at least 61% to at least 99% and all integer percentages in between) sequence similarity or sequence identity with the sequence set forth in any one of SEQ ID NO: 72, 74, 76, 78, 80, 82 or 84; or (c) an amino acid sequence which is encoded by the nucleotide sequence set forth in any one of SEQ ID NO:71 (nucleotide sequence encoding SEQ ID NO:72), SEQ ID NO:73 (nucleotide sequence encoding SEQ ID NO:74), SEQ ID NO:75 (nucleotide sequence encoding SEQ ID NO:76), SEQ ID NO:77 (nucleotide sequence encoding SEQ ID NO:78), SEQ ID NO:79 (nucleotide sequence encoding SEQ ID NO:80), SEQ ID NO:81 (nucleotide sequence encoding SEQ ID NO:82) or SEQ ID NO:83 (nucleotide sequence encoding SEQ ID NO:84);

(d) an amino acid sequence which is encoded by a nucleotide sequence that shares at least 60% (and at least 61% to at least 99% and all integer percentages in between) sequence identity with the sequence set forth in any one of SEQ ID NO: 71, 73, 75, 77, 79, 81 or 83, or a complement thereof; or (e) an amino acid sequence which is encoded by a nucleotide sequence that hybridizes under at least medium stringency conditions to the sequence set forth in any one of SEQ ID NO: 71, 73, 75, 77, 79, 81 or 83, or a complement thereof, wherein the amino acid sequence of (a), (b), (c), (d) or (e) has any one or more activities selected from the group consisting of: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

In other illustrative examples, the proteinaceous molecules consist or consists essentially of an amino acid sequence (also referred to herein as a "class VII amino acid sequence") selected from the group consisting of:

(a) an amino acid sequence selected from: LFSSEESNLGANNYDDYRMDWL [SEQ ID NO:86, from human vitronectin]; WFSSEETGPGGYNYDDYKMDWL [SEQ ID NO:88, from pig vitronectin]; WLSSEELGLGANNYDSFEMDWL [SEQ ID NO:90 from bovine vitronectin]; WFSSEELGLGADNYDNYEMDWL [SEQ ID NO:92, from goat vitronectin]; LFSSEESGLGTYNNYDYDMDWL [SEQ ID NO:94, from mouse vitronectin]; WFSSEEVSLGPYNYEDYETSWL [SEQ ID NO:96, from rabbit vitronectin]; and LLSSEESGLGTYNYDYDMNWL [SEQ ID NO:98, from rat vitronectin];

(b) an amino acid sequence that shares at least 60% (and at least 61% to at least 99% and all integer percentages in between) sequence similarity or sequence identity with the sequence set forth in any one of SEQ ID NO: 86, 88, 90, 92, 94, 96 or 98; or (c) an amino acid sequence which is encoded by the nucleotide sequence set forth in any one of SEQ ID NO:85 (nucleotide sequence encoding SEQ ID NO:86), SEQ ID NO:87 (nucleotide sequence encoding SEQ ID NO:88), SEQ ID NO:89 (nucleotide sequence encoding SEQ ID NO:90), SEQ ID NO:91 (nucleotide sequence encoding SEQ ID NO:92), SEQ ID NO:93 (nucleotide sequence encoding SEQ ID NO:94), SEQ ID NO:95 (nucleotide sequence encoding SEQ ID NO:96) or SEQ ID NO:97 (nucleotide sequence encoding SEQ ID NO:98);

(d) an amino acid sequence which is encoded by a nucleotide sequence that shares at least 60% (and at least 61% to at least 99% and all integer percentages in between) sequence identity with the sequence set forth in any one of SEQ ID NO: 85, 87, 89, 91, 93, 95 or 97, or a complement thereof; or (e) an amino acid sequence which is encoded by a nucleotide sequence that hybridizes under at least medium stringency conditions to the sequence set forth in any one of SEQ ID NO: 85, 87, 89, 91, 93, 95 or 97, or a complement thereof, wherein the amino acid sequence of (a), (b), (c), (d) or (e) has any one or more activities selected from the group consisting of: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

In still other illustrative examples, the proteinaceous molecules consist or consists essentially of an amino acid sequence (also referred to herein as a "class VIII amino acid sequence") selected from the group consisting of:

(a) an amino acid sequence selected from: RVNLRTRRVDTVDPPYPRS [SEQ ID NO:100, from human vitronectin]; RVNLRTQRVDTVTPPYPRS [SEQ ID NO:102, from pig vitronectin]; RVNLRTRRVDAVIPPYPRS [SEQ ID NO:104, from bovine vitronectin]; RVNLRTRRVDSVIPPYPRS [SEQ ID NO:106, from goat vitronectin]; RVNLRTRRVDSVNPPYPRS [SEQ ID NO:108, from mouse vitronectin]; RVNLRTQRVDTVNPPYPRS [SEQ ID NO:110, from rabbit vitronectin]; and RVNLRTRRVDSVNPPYPRS [SEQ ID NO:112, from rat vitronectin];

(b) an amino acid sequence that shares at least 60% (and at least 61% to at least 99% and all integer percentages in between) sequence similarity or sequence identity with the sequence set forth in any one of SEQ ID NO: 100, 102, 104, 106, 108, 110 or 112; or (c) an amino acid sequence which is encoded by the nucleotide sequence set forth in any one of SEQ ID NO:99 (nucleotide sequence encoding SEQ ID NO:100), SEQ ID NO:101 (nucleotide sequence encoding SEQ ID NO:102), SEQ ID NO:103 (nucleotide sequence encoding SEQ ID NO:104), SEQ ID NO:105 (nucleotide sequence encoding SEQ ID NO:106), SEQ ID NO:107 (nucleotide sequence encoding SEQ ID NO:108), SEQ ID NO:109 (nucleotide sequence encoding SEQ ID NO:110) or SEQ ID NO:111 (nucleotide sequence encoding SEQ ID NO:112);

(d) an amino acid sequence which is encoded by a nucleotide sequence that shares at least 60% (and at least 61% to at least 99% and all integer percentages in between) sequence identity with the sequence set forth in any one of SEQ ID NO: 99, 101, 103, 105, 107, 109 or 111, or a complement thereof; or (e) an amino acid sequence which is encoded by a nucleotide sequence that hybridizes under at least medium stringency conditions to the sequence set forth in any one of SEQ ID NO: 99, 101, 103, 105, 107, 109 or 111, or a complement thereof, wherein the amino acid sequence of (a), (b), (c), (d) or (e) has any one or more activities selected from the group consisting of: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

In a related aspect, the present invention provides proteinaceous molecules consisting or consisting essentially of an amino acid sequence selected from the group consisting of (a) to (e), as broadly defined in any one or more of the aspects defined above.

Another aspect of the present invention provides isolated nucleic acid molecules that comprise, consist or consist essentially of a nucleotide sequence encoding the amino acid sequence of a proteinaceous molecule as broadly defined above. In some embodiments, the nucleic acid molecules comprise, consist or consist essentially of a nucleotide sequence selected from:

(a) a nucleotide sequence selected from: [SEQ ID NO:1; nucleotide sequence encoding SEQ ID NO:2]; [SEQ ID NO:3; nucleotide sequence encoding SEQ ID NO:4]; [SEQ ID NO:5; nucleotide sequence SEQ ID NO:6]; [SEQ ID NO:7; nucleotide sequence encoding SEQ ID NO:8]; [SEQ ID NO:9; nucleotide sequence SEQ ID NO:10]; [SEQ ID NO:11; nucleotide sequence encoding SEQ ID NO:12]; [SEQ ID NO:13; nucleotide sequence encoding SEQ ID NO:14]; [SEQ ID NO:15; nucleotide sequence encoding SEQ ID NO:16]; [SEQ ID NO:17; nucleotide sequence SEQ ID NO:18]; [SEQ ID NO:19; nucleotide sequence encoding SEQ ID NO:20]; [SEQ ID NO:21; nucleotide sequence SEQ ID NO:22]; [SEQ ID NO:23; nucleotide sequence encoding SEQ ID NO:24]; [SEQ ID NO:25; nucleotide sequence encoding SEQ ID NO:26]; [SEQ ID NO:27; nucleotide sequence encoding SEQ ID NO:28]; [SEQ ID NO:29; nucleotide sequence SEQ ID NO:30]; [SEQ ID NO:31; nucleotide sequence encoding SEQ ID NO:32]; [SEQ ID NO:33; nucleotide sequence SEQ ID NO:34]; [SEQ ID NO:35; nucleotide sequence encoding SEQ ID NO:36]; [SEQ ID NO:37; nucleotide sequence encoding SEQ ID NO:38]; [SEQ ID NO:39; nucleotide sequence encoding SEQ ID NO:40]; [SEQ ID NO:41; nucleotide sequence SEQ ID NO:42]; [SEQ ID NO:43; nucleotide sequence encoding SEQ ID NO:44]; [SEQ ID NO:45; nucleotide sequence SEQ ID NO:46]; [SEQ ID NO:47; nucleotide sequence encoding SEQ ID NO:48]; [SEQ ID NO:49; nucleotide sequence encoding SEQ ID NO:50]; [SEQ ID NO:51; nucleotide sequence encoding SEQ ID NO:52]; [SEQ ID NO:53; nucleotide sequence SEQ ID NO:54]; [SEQ ID NO:55; nucleotide sequence encoding SEQ ID NO:56]; [SEQ ID NO:57; nucleotide sequence SEQ ID NO:58]; [SEQ ID NO:59; nucleotide sequence encoding SEQ ID NO:60]; [SEQ ID NO:61; nucleotide sequence encoding SEQ ID NO:62]; [SEQ ID NO:63; nucleotide sequence encoding SEQ ID NO:64]; [SEQ ID NO:65; nucleotide sequence SEQ ID NO:66]; [SEQ ID NO:67; nucleotide sequence encoding SEQ ID NO:68]; [SEQ ID NO:69; nucleotide sequence SEQ ID NO:70]; [SEQ ID NO:71; nucleotide sequence encoding SEQ ID NO:72]; [SEQ ID NO:73; nucleotide sequence encoding SEQ ID NO:74]; [SEQ ID NO:75; nucleotide sequence encoding SEQ ID NO:76]; [SEQ ID NO:77; nucleotide sequence SEQ ID NO:78]; [SEQ ID NO:79; nucleotide sequence encoding SEQ ID NO:80]; [SEQ ID NO:81; nucleotide sequence SEQ ID NO:82]; [SEQ ID NO:83; nucleotide sequence encoding SEQ ID NO:84]; [SEQ ID NO:85; nucleotide sequence encoding SEQ ID NO:86]; [SEQ ID NO:87; nucleotide sequence encoding SEQ ID NO:88]; [SEQ ID NO:89; nucleotide sequence SEQ ID NO:90]; [SEQ ID NO:91; nucleotide sequence encoding SEQ ID NO:92]; [SEQ ID NO:93; nucleotide sequence SEQ ID NO:94]; [SEQ ID NO:95; nucleotide sequence encoding SEQ ID NO:96]; [SEQ ID NO:97; nucleotide sequence SEQ ID NO:98]; [SEQ ID NO:99; nucleotide sequence encoding SEQ ID NO:100]; [SEQ ID NO:101; nucleotide sequence SEQ ID NO:102]; [SEQ ID NO:103; nucleotide sequence encoding SEQ ID NO:104]; [SEQ ID NO:105; nucleotide sequence encoding SEQ ID NO:106]; [SEQ ID NO:107; nucleotide sequence encoding SEQ ID NO:108]; [SEQ ID NO:109; nucleotide sequence encoding SEQ ID NO:110]; [SEQ ID NO:111; nucleotide sequence encoding SEQ ID NO:112];

(b) a nucleotide sequence that shares at least 60% (and at least 61% to at least 99% and all integer percentages in between) sequence identity with the sequence set forth in any one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109 or 111, or a complement thereof;

(c) a nucleotide sequence that hybridizes under at least medium stringency conditions to the sequence set forth in any one of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109 or 111, or a complement thereof, wherein the amino acid sequence encoded by the nucleotide sequence of (a), (b) or (c) has any one or more activities selected from the group consisting of: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell).

A further aspect of the present invention provides nucleic acid constructs comprising, consisting or consisting essentially of a nucleic acid molecule, as broadly described above.

Still another aspect of the present invention provides constructs for expressing a nucleic acid molecule, as broadly described above. These constructs generally comprise the nucleic acid molecule operably connected to a regulatory sequence. In some embodiments, the construct further comprises a sequence for transport of the protein to the cell surface or to the extracellular environment.

In a related aspect, the present invention provides host cells that contain a construct as broadly described above.

In yet another aspect, the present invention provides pharmaceutical compositions that comprise an agent selected from a proteinaceous molecule, nucleic acid molecule, construct or cell, as broadly described above, and a pharmaceutically acceptable carrier or diluent. In some embodiments, the pharmaceutical compositions comprise at least one (e.g., 1, 2, 3, 4, 5, 6, 7, 8, or more) proteinaceous molecule as broadly described above, or at least one (e.g., 1, 2, 3, 4, 5, 6, 7, 8, or more) nucleic acid molecule as broadly described above, or at least one (e.g., 1, 2, 3, 4, 5, 6, 7, 8, or more) construct as broadly described above, or at least one (e.g., 1, 2, 3, 4, 5, 6, 7, 8, or more) host cell as broadly described above, or any combination of these. In specific embodiments, pharmaceutical compositions comprise a proteinaceous molecule consisting or consisting essentially of an amino acid sequence selected from an amino acid sequence represented by formula VII, an amino acid sequence represented by formula VIII, an amino acid sequence represented by formula XV, an amino acid sequence represented by formula XVI, a class VII amino acid sequence or a class VIII amino acid sequence). In some embodiments, the compositions further comprise at least one ancillary agent selected from an anti-infective agent (e.g., selected from antibiotics, amebicides, antifungals, antiprotozoals, antimalarials, antituberculotics and antivirals, etc.), a chemotherapeutic agent (e.g., selected from antiproliferative/antineoplastic drugs, cytostatic agents, agents that inhibit cancer cell invasion, inhibitors of growth factor function, anti-angiogenic agents, vascular damaging agents, etc.), or an immunotherapeutic agent (e.g., cytokines, cytokine-expressing cells, antibodies, etc.).

A further aspect of the present invention provides methods for: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); and (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell). These methods generally comprise contacting the IGF or IGFBP defined in (1), (2) or (3), or an IGF or IGFBP in the extracellular environment of the hyperproliferative cell defined in (4), (5), (6) or (7), with a proteinaceous molecule as broadly described above.

In yet another aspect, the present invention provides methods for inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell), or for inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell), or for inhibiting invasion of a hyperproliferative cell (e.g., a neoplastic cell such as an epithelial cancer cell), or for inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell) in a subject. These methods generally comprise administering to the subject an effective amount of a proteinaceous molecule, nucleic acid molecule, construct or cell as broadly described above.

Still another aspect of the present invention provides methods for treating or preventing a hyperproliferative cell disorder (e.g., non-neoplastic disorder such as keloid or glial scarring or a neoplastic disorder such as an epithelial cancer) in a subject. These methods generally comprise administering to the subject an effective amount of a proteinaceous molecule, nucleic acid molecule, construct or cell, as broadly described above, which are optionally in the form of a pharmaceutical composition as broadly described above.

In some embodiments, the above methods involving administration to the subject, further comprise concurrently administering to the subject with the proteinaceous molecule, nucleic acid molecule, construct or cell as broadly described at least one ancillary agent selected from an anti-infective agent (e.g., selected from antibiotics, amebicides, antifungals, antiprotozoals, antimalarials, antituberculotics and antivirals, etc.), a chemotherapeutic agent (e.g., selected from antiproliferative/antineoplastic drugs, cytostatic agents, agents that inhibit cancer cell invasion, inhibitors of growth factor function, anti-angiogenic agents, vascular damaging agents, etc.), or an immunotherapeutic agent (e.g., cytokines, cytokine-expressing cells, antibodies, etc.).

In related aspects, the present invention provides the use of a proteinaceous molecule, nucleic acid molecule, construct or cell as broadly described, and optionally at least one ancillary agent as broadly defined above, which are optionally in the form of a pharmaceutical composition as broadly described above for: (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibiting proliferation of a hyperproliferative cell (e.g., a non-neoplastic cell such as a normal epithelial (e.g., keratinocyte) or glial (e.g., astrocyte) cell or a neoplastic cell such as an epithelial cancer cell); (5) inhibiting migration of a hyperproliferative cell (e.g., a non-neoplastic cell such as a normal epithelial (e.g., keratinocyte) or glial (e.g., astrocyte) cell or a neoplastic cell such as an epithelial cancer cell); (6) inhibiting invasion of a hyperproliferative cell (e.g., a neoplastic cell such as an epithelial cancer cell); (7) inhibiting survival or viability of a hyperproliferative cell (e.g., a non-neoplastic cell such as a normal epithelial (e.g., keratinocyte) or glial (e.g., astrocyte) cell or a neoplastic cell such as an epithelial cancer cell) and/or (8) treating or preventing a hyperproliferative cell disorder (e.g., non-neoplastic disorder such as keloid or glial scarring or a neoplastic disorder such as an epithelial cancer)

Figure 1:
FIG. 1 is a diagrammatic representation showing the results of a PRALINE sequence alignment of the following vitronectin (VN) amino acid sequences: A. Peptide 1 sequences: SEQ ID NO:2, from human vitronectin; SEQ ID NO:4, from pig vitronectin; SEQ ID NO:6, from bovine vitronectin; SEQ ID NO:8, from goat vitronectin; SEQ ID NO:10, from mouse vitronectin; SEQ ID NO:12, from rabbit vitronectin; and SEQ ID NO:14, from rat vitronectin; B. Peptide 2 sequences: SEQ ID NO:16, from human vitronectin; SEQ ID NO:18, from pig vitronectin; SEQ ID NO:20, from bovine vitronectin; SEQ ID NO:22, from goat vitronectin; SEQ ID NO:24, from mouse vitronectin; SEQ ID NO:26, from rabbit vitronectin; and SEQ ID NO:28, from rat vitronectin; C. Peptide 3 sequences: SEQ ID NO:30, from human vitronectin; SEQ ID NO:32, from pig vitronectin; SEQ ID NO:34, from bovine vitronectin; SEQ ID NO:36, from goat vitronectin; SEQ ID NO:38, from mouse vitronectin; SEQ ID NO:40, from rabbit vitronectin; and SEQ ID NO:42, from rat vitronectin; D. Peptide 4 sequences: SEQ ID NO:44, from human vitronectin; SEQ ID NO:46, from pig vitronectin; SEQ ID NO:48, from bovine vitronectin; SEQ ID NO:50, from goat vitronectin; SEQ ID NO:52, from mouse vitronectin; SEQ ID NO:54, from rabbit vitronectin; and SEQ ID NO:56, from rat vitronectin; E. Peptide 5 sequences: SEQ ID NO:58, from human vitronectin; SEQ ID NO:60, from pig vitronectin; SEQ ID NO:62, from bovine vitronectin; SEQ ID NO:64, from goat vitronectin; SEQ ID NO:66, from mouse vitronectin; SEQ ID NO:68, from rabbit vitronectin; and SEQ ID NO:70, from rat vitronectin; F. Peptide 6 sequences: SEQ ID NO:72, from human vitronectin; SEQ ID NO:74, from pig vitronectin; SEQ ID NO:76, from bovine vitronectin; SEQ ID NO:78, from goat vitronectin; SEQ ID NO:80, from mouse vitronectin; SEQ ID NO:82, from rabbit vitronectin; and SEQ ID NO:84, from rat vitronectin; G. Peptide 7 sequences: SEQ ID NO:86, from human vitronectin; SEQ ID NO:88, from pig vitronectin; SEQ ID NO:90 from bovine vitronectin; SEQ ID NO:92, from goat vitronectin; SEQ ID NO:94, from mouse vitronectin; SEQ ID NO:96, from rabbit vitronectin; and SEQ ID NO:98, from rat vitronectin; H. Peptide 8 sequences: SEQ ID NO:100, from human vitronectin; SEQ ID NO:102, from pig vitronectin; SEQ ID NO:104, from bovine vitronectin; SEQ ID NO:106, from goat vitronectin; SEQ ID NO:108, from mouse vitronectin; SEQ ID NO:110, from rabbit vitronectin; and SEQ ID NO:112, from rat vitronectin.

Some figures contain color representations or entities. Color illustrations are available from the Applicant upon request or from an appropriate Patent Office. A fee may be imposed if obtained from the Patent Office.

TABLE 1

| BRIEF DESCRIPTION OF THE SEQUENCES | | |
|---|---|---|
| SEQUENCE ID NUMBER | SEQUENCE | LENGTH |
| SEQ ID NO: 1 | Nucleotide sequence from *Homo sapiens*, which encodes a VN peptide falling within the scope of formula I | 57 nts |
| SEQ ID NO: 2 | Peptide encoded by SEQ ID NO: 1 | 19 aa |
| SEQ ID NO: 3 | Nucleotide sequence from *Sus scrofa*, which encodes a VN peptide falling within the scope of formula I | 57 nts |
| SEQ ID NO: 4 | Peptide encoded by SEQ ID NO: 3 | 19 aa |
| SEQ ID NO: 5 | Nucleotide sequence from *Bos taurus*, which encodes a VN peptide falling within the scope of formula I | 57 nts |
| SEQ ID NO: 6 | Peptide encoded by SEQ ID NO: 5 | 19 aa |
| SEQ ID NO: 7 | Nucleotide sequence from *Capra hircus*, which encodes a VN peptide falling within the scope of formula I | 57 nts |
| SEQ ID NO: 8 | Peptide encoded by SEQ ID NO: 7 | 19 aa |
| SEQ ID NO: 9 | Nucleotide sequence from *Mus musculus*, which encodes a VN peptide falling within the scope of formula I | 57 nts |
| SEQ ID NO: 10 | Peptide encoded by SEQ ID NO: 9 | 19 aa |
| SEQ ID NO: 11 | Nucleotide sequence from *Oryctolagus cuniculus*, which encodes a VN peptide falling within the scope of formula I | 57 nts |
| SEQ ID NO: 12 | Peptide encoded by SEQ ID NO: 11 | 19 aa |
| SEQ ID NO: 13 | Nucleotide sequence from *Rattus norvegicus*, which encodes a VN peptide falling within the scope of formula I | 57 nts |

TABLE 1-continued

BRIEF DESCRIPTION OF THE SEQUENCES

| SEQUENCE ID NUMBER | SEQUENCE | LENGTH |
|---|---|---|
| SEQ ID NO: 14 | Peptide encoded by SEQ ID NO: 13 | 19 aa |
| SEQ ID NO: 15 | Nucleotide sequence from *H. sapiens*, which encodes a VN peptide falling within the scope of formula II | 24 nts |
| SEQ ID NO: 16 | Peptide encoded by SEQ ID NO: 15 | 8 aa |
| SEQ ID NO: 17 | Nucleotide sequence from *S. scrofa*, which encodes a VN peptide falling within the scope of formula II | 24 nts |
| SEQ ID NO: 18 | Peptide encoded by SEQ ID NO: 17 | 8 aa |
| SEQ ID NO: 19 | Nucleotide sequence from *B. taurus*, which encodes a VN peptide falling within the scope of formula II | 24 nts |
| SEQ ID NO: 20 | Peptide encoded by SEQ ID NO: 19 | 8 aa |
| SEQ ID NO: 21 | Nucleotide sequence from *C. hircus*, which encodes a VN peptide falling within the scope of formula II | 24 nts |
| SEQ ID NO: 22 | Peptide encoded by SEQ ID NO: 21 | 8 aa |
| SEQ ID NO: 23 | Nucleotide sequence from *M. musculus*, which encodes a VN peptide falling within the scope of formula II | 24 nts |
| SEQ ID NO: 24 | Peptide encoded by SEQ ID NO: 23 | 8 aa |
| SEQ ID NO: 25 | Nucleotide sequence from *O. cuniculus*, which encodes a VN peptide falling within the scope of formula II | 24 nts |
| SEQ ID NO: 26 | Peptide encoded by SEQ ID NO: 25 | 8 aa |
| SEQ ID NO: 27 | Nucleotide sequence from *R. norvegicus*, which encodes a VN peptide falling within the scope of formula II | 24 nts |
| SEQ ID NO: 28 | Peptide encoded by SEQ ID NO: 27 | 8 aa |
| SEQ ID NO: 29 | Nucleotide sequence from *H. sapiens*, which encodes a VN peptide falling within the scope of formula III | 57 nts |
| SEQ ID NO: 30 | Peptide encoded by SEQ ID NO: 29 | 19 aa |
| SEQ ID NO: 31 | Nucleotide sequence from *S. scrofa*, which encodes a VN peptide falling within the scope of formula III | 57 nts |
| SEQ ID NO: 32 | Peptide encoded by SEQ ID NO: 31. | 19 aa |
| SEQ ED NO: 33 | Nucleotide sequence from *B. taurus*, which encodes a VN peptide falling within the scope of formula III | 57 nts |
| SEQ ID NO: 34 | Peptide encoded by SEQ ID NO: 33 | 19 aa |
| SEQ ID NO: 35 | Nucleotide sequence from *C. hircus*, which encodes a VN peptide falling within the scope of formula III | 57 nts |
| SEQ ID NO: 36 | Peptide encoded by SEQ ID NO: 35 | 19 aa |
| SEQ ID NO: 37 | Nucleotide sequence from *M. musculus*, which encodes a VN peptide falling within the scope of formula III | 57 nts |
| SEQ ID NO: 38 | Peptide encoded by SEQ ID NO: 37 | 19 aa |
| SEQ ID NO: 39 | Nucleotide sequence from *O. cuniculus*, which encodes a VN peptide falling within the scope of formula III | 57 nts |
| SEQ ID NO: 40 | Peptide encoded by SEQ ID NO: 39 | 19 aa |
| SEQ ID NO: 41 | Nucleotide sequence from *R. norvegicus*, which encodes a VN peptide falling within the scope of formula III | 57 nts |
| SEQ ID NO: 42 | Peptide encoded by SEQ ID NO: 41 | 19 aa |
| SEQ ID NO: 43 | Nucleotide sequence from *H. sapiens*, which encodes a VN peptide falling within the scope of formula IV | 57 nts |
| SEQ ID NO: 44 | Peptide encoded by SEQ ID NO: 43 | 19 aa |
| SEQ ID NO: 45 | Nucleotide sequence from *S. scrofa*, which encodes a VN peptide falling within the scope of formula IV | 57 nts |
| SEQ ID NO: 46 | Peptide encoded by SEQ ID NO: 45 | 19 aa |
| SEQ ID NO: 47 | Nucleotide sequence from *B. taurus*, which encodes a VN peptide falling within the scope of formula IV | 57 nts |
| SEQ ID NO: 48 | Peptide encoded by SEQ ID NO: 47 | 19 aa |
| SEQ ID NO: 49 | Nucleotide sequence from *C. hircus*, which encodes a VN peptide falling within the scope of formula IV | 57 nts |
| SEQ ID NO: 50 | Peptide encoded by SEQ ID NO: 49 | 19 aa |
| SEQ ID NO: 51 | Nucleotide sequence from *M. musculus*, which encodes a VN peptide falling within the scope of formula IV | 57 nts |
| SEQ ID NO: 52 | Peptide encoded by SEQ ID NO: 51 | 19 aa |
| SEQ ID NO: 53 | Nucleotide sequence from *O. cuniculus*, which encodes a VN peptide falling within the scope of formula IV | 57 nts |
| SEQ ID NO: 54 | Peptide encoded by SEQ ID NO: 53 | 19 aa |
| SEQ ID NO: 55 | Nucleotide sequence from *R. norvegicus*, which encodes a VN peptide falling within the scope of formula IV | 57 nts |
| SEQ ID NO: 56 | Peptide encoded by SEQ ID NO: 55 | 19 aa |
| SEQ ID NO: 57 | Nucleotide sequence from *H. sapiens*, which encodes a VN peptide falling within the scope of formula V | 75 nts |
| SEQ ID NO: 58 | Peptide encoded by SEQ ID NO: 57 | 25 aa |
| SEQ ID NO: 59 | Nucleotide sequence from *S. scrofa*, which encodes a VN peptide falling within the scope of formula V | 75 nts |
| SEQ ID NO: 60 | Peptide encoded by SEQ ID NO: 59 | 25 aa |
| SEQ ID NO: 61 | Nucleotide sequence from *B. taurus*, which encodes a VN peptide falling within the scope of formula V | 75 nts |
| SEQ ID NO: 62 | Peptide encoded by SEQ ID NO: 61 | 25 aa |
| SEQ ID NO: 63 | Nucleotide sequence from *C. hircus*, which encodes a VN peptide falling within the scope of formula V | 75 nts |

TABLE 1-continued

BRIEF DESCRIPTION OF THE SEQUENCES

| SEQUENCE ID NUMBER | SEQUENCE | LENGTH |
|---|---|---|
| SEQ ID NO: 64 | Peptide encoded by SEQ ID NO: 63 | 25 aa |
| SEQ ID NO: 65 | Nucleotide sequence from *M. musculus*, which encodes a VN peptide falling within the scope of formula V | 75 nts |
| SEQ ID NO: 66 | Peptide encoded by SEQ ID NO: 65 | 25 aa |
| SEQ ID NO: 67 | Nucleotide sequence from *O. cuniculus*, which encodes a VN peptide falling within the scope of formula V | 75 nts |
| SEQ ID NO: 68 | Peptide encoded by SEQ ID NO: 67 | 25 aa |
| SEQ ID NO: 69 | Nucleotide sequence from *R. norvegicus*, which encodes a VN peptide falling within the scope of formula V | 75 nts |
| SEQ ID NO: 70 | Peptide encoded by SEQ ID NO: 69 | 25 aa |
| SEQ ID NO: 71 | Nucleotide sequence from *H. sapiens*, which encodes a VN peptide falling within the scope of formula VI | 66 nts |
| SEQ ID NO: 72 | Peptide encoded by SEQ ID NO: 71 | 22 aa |
| SEQ ID NO: 73 | Nucleotide sequence from *S. scrofa*, which encodes a VN peptide falling within the scope of formula VI | 66 nts |
| SEQ ID NO: 74 | Peptide encoded by SEQ ID NO: 73 | 22 aa |
| SEQ ID NO: 75 | Nucleotide sequence from *B. taurus*, which encodes a VN peptide falling within the scope of formula VI | 66 nts |
| SEQ ID NO: 76 | Peptide encoded by SEQ ID NO: 75 | 22 aa |
| SEQ ID NO: 77 | Nucleotide sequence from *C. hircus*, which encodes a VN peptide falling within the scope of formula VI | 66 nts |
| SEQ ID NO: 78 | Peptide encoded by SEQ ID NO: 77 | 22 aa |
| SEQ ID NO: 79 | Nucleotide sequence from *M. musculus*, which encodes a VN peptide falling within the scope of formula VI | 66 nts |
| SEQ ID NO: 80 | Peptide encoded by SEQ ID NO: 79 | 22 aa |
| SEQ ID NO: 81 | Nucleotide sequence from *O. cuniculus*, which encodes a VN peptide falling within the scope of formula VI | 66 nts |
| SEQ ID NO: 82 | Peptide encoded by SEQ ID NO: 81 | 22 aa |
| SEQ ID NO: 83 | Nucleotide sequence from *R. norvegicus*, which encodes a VN peptide falling within the scope of formula VI | 66 nts |
| SEQ ID NO: 84 | Peptide encoded by SEQ ID NO: 83 | 22 aa |
| SEQ ID NO: 85 | Nucleotide sequence from *H. sapiens*, which encodes a VN peptide falling within the scope of formula VII | 66 nts |
| SEQ ID NO: 86 | Peptide encoded by SEQ ID NO: 85 | 22 aa |
| SEQ ID NO: 87 | Nucleotide sequence from *S. scrofa*, which encodes a VN peptide falling within the scope of formula VII | 66 nts |
| SEQ ID NO: 88 | Peptide encoded by SEQ ID NO: 87 | 22 aa |
| SEQ ID NO: 89 | Nucleotide sequence from *B. taurus*, which encodes a VN peptide falling within the scope of formula VII | 66 nts |
| SEQ ID NO: 90 | Peptide encoded by SEQ ID NO: 89 | 22 aa |
| SEQ ID NO: 91 | Nucleotide sequence from *C. hircus*, which encodes a VN peptide falling within the scope of formula VII | 66 nts |
| SEQ ID NO: 92 | Peptide encoded by SEQ ID NO: 91 | 22 aa |
| SEQ ID NO: 93 | Nucleotide sequence from *M. musculus*, which encodes a VN peptide falling within the scope of formula VII | 66 nts |
| SEQ ID NO: 94 | Peptide encoded by SEQ ID NO: 93 | 22 aa |
| SEQ ID NO: 95 | Nucleotide sequence from *O. cuniculus*, which encodes a VN peptide falling within the scope of formula VII | 66 nts |
| SEQ ED NO: 96 | Peptide encoded by SEQ ID NO: 95 | 22 aa |
| SEQ ID NO: 97 | Nucleotide sequence from *R. norvegicus*, which encodes a VN peptide falling within the scope of formula VII | 63 nts |
| SEQ ID NO: 98 | Peptide encoded by SEQ ID NO: 97 | 21 aa |
| SEQ ID NO: 99 | Nucleotide sequence from *H. sapiens*, which encodes a VN peptide falling within the scope of formula VIII | 57 nts |
| SEQ ID NO: 100 | Peptide encoded by SEQ ID NO: 99 | 19 aa |
| SEQ ID NO: 101 | Nucleotide sequence from *S. scrofa*, which encodes a VN peptide falling within the scope of formula VIII | 57 nts |
| SEQ ID NO: 102 | Peptide encoded by SEQ ID NO: 101 | 19 aa |
| SEQ ID NO: 103 | Nucleotide sequence from *B. taurus*, which encodes a VN peptide falling within the scope of formula VIII | 57 nts |
| SEQ ID NO: 104 | Peptide encoded by SEQ ID NO: 103 | 19 aa |
| SEQ ID NO: 105 | Nucleotide sequence from *C. hircus*, which encodes a VN peptide falling within the scope of formula VIII | 57 nts |
| SEQ ID NO: 106 | Peptide encoded by SEQ ID NO: 105 | 19 aa |
| SEQ ID NO: 107 | Nucleotide sequence from *M. musculus*, which encodes a VN peptide falling within the scope of formula VIII | 57 nts |
| SEQ ID NO: 108 | Peptide encoded by SEQ ID NO: 107 | 19 aa |
| SEQ ID NO: 109 | Nucleotide sequence from *O. cuniculus*, which encodes a VN peptide falling within the scope of formula VIII | 57 nts |
| SEQ ID NO: 110 | Peptide encoded by SEQ ID NO: 109 | 19 aa |
| SEQ ID NO: 111 | Nucleotide sequence from *R. norvegicus*, which encodes a VN peptide falling within the scope of formula VIII | 57 nts |
| SEQ ID NO: 112 | Peptide encoded by SEQ ID NO: 111 | 19 aa |
| SEQ ID NO: 113 | Non-binding negative control VN-peptide | 16 aa |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element. As used herein, the use of the singular includes the plural (and vice versa) unless specifically stated otherwise.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" or "modulatory agent" includes a compound that induces a desired pharmacological and/or physiological effect. The term also encompass pharmaceutically acceptable and pharmacologically active ingredients of those compounds specifically mentioned herein including but not limited to, salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and nucleic acid molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. Thus, the term "agent" extends to nucleic acid constructs including vectors such as viral or non-viral vectors, expression vectors and plasmids for expression in and secretion in a range of cells.

By "coding sequence" is meant any nucleic acid sequence that contributes to the code for the peptide or polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. In some embodiments, the phrase "consisting essentially of" in the context of a recited subunit sequence (e.g., amino acid sequence or nucleic acid sequence) indicates that the sequence may comprise at least one additional upstream subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more upstream subunits; e.g., amino acids or nucleotides) and/or at least one additional downstream subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more upstream subunits; e.g., amino acids or nucleotides), wherein the number of upstream subunits and the number of downstream subunits are independently selectable.

By "corresponds to" or "corresponding to" is meant a nucleic acid sequence that displays substantial sequence identity to a reference nucleic acid sequence (e.g., at least about 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence identity to all or a portion of the reference nucleic acid sequence) or an amino acid sequence that displays substantial sequence similarity or identity to a reference amino acid sequence (e.g., at least 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to all or a portion of the reference amino acid sequence).

By "effective amount," in the context of treating or preventing a disease or condition (e.g., a hyperproliferative cell disorder) is meant the administration of an amount of active agent to a subject, either in a single dose or as part of a series or slow release system, which is effective for the treatment or prevention of that disease or condition. The effective amount will vary depending upon the health and physical condition of the subject and the taxonomic group of individual to be treated, the formulation of the composition, the assessment of the medical situation, and other relevant factors.

The terms "expression" or "gene expression" refer to either production of RNA message or translation of RNA message into proteins or polypeptides.

By "expression vector" is meant any genetic element capable of directing the transcription of a polynucleotide contained within the vector and suitably the synthesis of a peptide or polypeptide encoded by the polynucleotide. Such expression vectors are known to practitioners in the art.

As used herein, the terms "function," "functional" and the like refer to a biological, enzymatic, or therapeutic function.

The term "gene" as used herein refers to any and all discrete coding regions of the cell's genome, as well as associated non-coding and regulatory regions. The term is intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances as known to those of skill in the art.

The phrase "hybridizing specifically to" and the like refer to the binding, duplexing, or hybridizing of a molecule only to a particular nucleotide sequence under stringent conditions when that sequence is present in a complex mixture (e.g., total cellular) DNA or RNA.

As used herein, the term "hyperproliferative cell disorder" refers to a disorder in which cellular hyperproliferation causes or contributes to the pathological state or symptoms of the disorder. Illustrative hyperproliferative cell disorders include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. Exemplary hyperproliferative cell disorders include: cancers; blood vessel proliferative disorders such as restenosis, atherosclerosis, in-stent stenosis, vascular graft restenosis, etc.; fibrotic disorders; psoriasis; inflammatory disorders, e.g., arthritis, etc.; glomerular nephritis; endometriosis; macular degenerative disorders; benign growth disorders such as prostate enlargement and lipomas; autoimmune disorders; and scarring disorders such as post-operative scarring, hypertrophic scarring, keloid scarring and glial scarring. In some embodiments, the hyperproliferative cell disorder is a precancer or a precancerous condition. A "precancer cell" or "precancerous cell" is a cell manifesting a hyperproliferative cell disorder that is a pre-cancer or a precancerous condition. In other embodiments, the hyperproliferative cell disorder is a cancer. The term "cancer" is used interchangeably herein with the term "neoplastic" to refer to a disease or condition involving cells that metastasize or have the potential to metastasize to distal sites and exhibit phenotypic traits that differ from those of non-neoplastic cells, for example, formation of colonies in a three-dimensional substrate such as soft agar or the formation of tubular networks or web-like matrices in a three-dimensional basement membrane or extracellular matrix preparation, such as Matrigel™. Non-neoplastic cells do not form colonies in soft agar and form distinct sphere-like structures in three-dimensional basement membrane or extracellular matrix preparations. Neoplastic cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. Thus, "non-neoplastic" means that the condition, disease, or disorder does not involve cancer cells. Exemplary cancers includes solid tumors, as well as, hematologic tumors and/or malignancies. A "cancer cell," "cancerous cell" or "neoplastic cell" is a cell manifesting a hyperproliferative cell disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers. Representative cancers contemplated by the present invention include, but are not limited to, sarcomas, melanomas, adenomas, carcinomas of solid tissue (e.g., breast, ovary, prostate, colon, lung, skin, kidney, bladder, pancreas, head and neck) including squamous cell carcinomas of the mouth, throat, larynx, and lung; hypoxic tumors; hematopoietic cancers; nervous system cancers; benign lesions such as papillomas; leukemias, and lymphomas (Hodgkins and non-Hodgkins). As used herein, the term "cancer" refers to primary or metastatic cancers. In other embodiments, the hyperproliferative cell disorder is a non-neoplastic disorder in which cellular hyperproliferation causes or contributes to the pathological state or symptoms of the disorder.

As used herein, the terms "inhibit," "inhibiting" and the like are used interchangeably herein to refer to blocking, stopping, diminishing, reducing, impeding or impairing an activity, function or characteristic such as but not limited to binding, formation of a complex, proliferation, migration, invasion, survival or viability, in any setting including in vivo, ex vivo or in vitro. By way of example, "inhibit" can refer to a decrease of about 10%, 20%, 30%, 40%, 50%, 60%, 70%, 80%, 90% or 100% in an activity, function or characteristic.

By "isolated" is meant material that is substantially or essentially free from components that normally accompany it in its native state, or from components present during its production when purified or produced by synthetic means. Thus, the term "isolated" also includes within its scope purified or synthetic material.

By "modulating" is meant increasing or decreasing, either directly or indirectly, the level or functional activity of a target molecule. For example, an agent may indirectly modulate the level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably connected" or "operably linked" as used herein means placing a structural gene under the regulatory control of a regulatory element including but not limited to a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The terms "patient," "subject," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (Pan troglodytes)), rodents (e.g., mice, rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars), marine mammals (e.g., dolphins, whales), reptiles (e.g., snakes, frogs, lizards), and fish. In specific embodiments, the subject is a primate such as a human. However, it will be understood that the aforementioned terms do not imply that symptoms are present.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, amide, prodrug or derivative of a compound as provided herein is a salt, ester, amide, prodrug or derivative that this not biologically or otherwise undesirable.

The terms "polynucleotide," "genetic material," "genetic forms," "nucleic acids" and "nucleotide sequence" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art.

The terms "polynucleotide variant" and "variant" refer to polynucleotides displaying substantial sequence identity with a reference polynucleotide sequence or polynucleotides that hybridize with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally occurring allelic variants.

The terms "polypeptide," "proteinaceous molecule," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject proteinaceous molecules are particularly useful. Included within the definition are, for example, polypeptides containing one or more analogs of an amino acid including, for example, unnatural amino acids or polypeptides with substituted linkages.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

As used herein, the terms "prevent," "prevented," or "preventing," refer to a prophylactic treatment which increases the resistance of a subject to developing the disease or condition or, in other words, decreases the likelihood that the subject will develop the disease or condition as well as a treatment after the disease or condition has begun in order to reduce or eliminate it altogether or prevent it from becoming worse. These terms also include within their scope preventing the disease or condition from occurring in a subject which may be predisposed to the disease or condition but has not yet been diagnosed as having it.

As used herein, the term "purified" refers to material (e.g., a nucleic acid, peptide or polypeptide) that is substantially free of cellular components or other contaminating material from the cell or tissue source from which the material is derived, or substantially free from chemical precursors or other chemicals when chemically synthesized. "Substantially free" means that a preparation of a material (e.g., a nucleic acid, peptide or polypeptide) is at least 10%, 20%, 30%, 40%, 50%, 60%, 70%, 80%, 90%, 95%, 96%, 97%, 98%, 99% pure. In a preferred embodiment, the preparation of a material has less than about 40%, 30%, 20%, 10% and more suitably 5%, 4%, 3%, 2%, 1% (by dry weight), of non-material components or of chemical precursors or of non-material chemicals (also referred to herein as a "contaminating components"). When a material (e.g., a peptide or polypeptide is recombinantly produced, it is also suitably substantially free of culture medium, i.e., culture medium represents less than about 20%, 15%, 10%, 5%, 4%, 3%, 2%, 1% of the volume of the material preparation. The invention includes isolated or purified preparations of at least 0.01, 0.1, 1.0, and 10 milligrams in dry weight.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table 2.

TABLE 2

| ORIGINAL RESIDUE | EXEMPLARY SUBSTITUTIONS |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Similarity may be determined using sequence comparison programs such as GAP (Deveraux et al. 1984, *Nucleic Acids Research* 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12, 13, 14, 15, 16, 17, 18, 19, 20, 21, 22, 23, 24, 25, 26, 27, 28, 29, 30, 35, 40, 45, 50, 60, 70, 80, 90, 100, 110, 120, 130, 140, 150, 200, 250, 300, 350, 400, 450, 500, 600, 700, 800, 900 or 1000 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology," John Wiley & Sons Inc, 1994-1998, Chapter 15.

"Stringency" as used herein refers to the temperature and ionic strength conditions, and presence or absence of certain organic solvents, during hybridization. The higher the stringency, the higher will be the observed degree of complementarity between sequences. "Stringent conditions" as used herein refers to temperature and ionic conditions under which only polynucleotides having a high proportion of complementary bases, preferably having exact complementarity, will hybridize. The stringency required is nucleotide sequence dependent and depends upon the various components present during hybridization, and is greatly changed when nucleotide analogues are used. Generally, stringent conditions are selected to be about 10° C. to 20° C. less than the thermal melting point (Tm) for the specific sequence at a defined ionic strength and pH. The Tm is the temperature (under defined ionic strength and pH) at which 50% of a target sequence hybridizes to a complementary probe. It will be understood that a polynucleotide will hybridize to a target sequence under at least low stringency conditions, preferably under at least medium stringency conditions and more preferably under high stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. Medium stringency conditions include and encompass from at least about 16% v/v to at least about 30% v/v formamide and from at least about 0.5 M to at least about 0.9 M salt for hybridization at 42° C., and at least about 0.5 M to at least about 0.9 M salt for washing at 42° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 42° C. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing 0.5 M sodium phosphate, 7% SDS at 65° C., followed by one or more washes at 0.2×SSC, 1% SDS at 65° C. Other stringent conditions are well known in the art. A skilled addressee will recognize that various factors can be manipulated to optimize the specificity of the hybridization. Optimization of the stringency of the final washes can serve to ensure a high degree of hybridization. For detailed examples, see CURRENT PROTOCOLS IN MOLECULAR BIOLOGY (supra) at pages 2.10.1 to 2.10.16 and MOLECULAR CLONING. A LABORATORY MANUAL (Sambrook, et al., eds.) (Cold Spring Harbor Press 1989) at sections 1.101 to 1.104.

By "substantially complementary" it is meant that an oligonucleotide or a subsequence thereof is sufficiently complementary to hybridize with a target sequence. Accordingly, the nucleotide sequence of the oligonucleotide or subsequence need not reflect the exact complementary sequence of the target sequence. In a preferred embodiment, the oligonucleotide contains no mismatches and with the target sequence.

As used herein, by "synthetic" is meant not naturally occurring but made through human technical intervention. In the context of synthetic proteins, peptides and nucleic acids, this encompasses molecules produced by recombinant, chemical synthetic or combinatorial techniques as are well understood in the art.

As used herein, the terms "treatment," "treating," and the like, refer to obtaining a desired pharmacologic and/or physiologic effect. The effect may be therapeutic in terms of a partial or complete cure for a disease or condition (e.g., a hyperproliferative cell disorder) and/or adverse effect attributable to the disease or condition. These terms also cover any treatment of a condition or disease in a mammal, particularly in a human, and include: (a) inhibiting the disease or condition, i.e., arresting its development; or (b) relieving the disease or condition, i.e., causing regression of the disease or condition.

By "vector" is meant a polynucleotide molecule, suitably a DNA molecule derived, for example, from a plasmid, bacteriophage, virus, yeast or higher order eukaryote including plant, vertebrate or invertebrate animal, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In some embodiments, the vector is a viral or viral-derived vector, which is operably functional in vertebrate or invertebrate animal and suitably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene, which confers resistance to the antibiotic hygromycin B.

The terms "wild-type" and "naturally occurring" are used interchangeably to refer to a gene or gene product that has the characteristics (e.g., nucleotide sequence, amino acid sequence, etc.) of that gene or gene product when isolated from a naturally occurring source. A wild type gene or gene product (e.g., a polypeptide) is that which is most frequently observed in a population and is thus arbitrarily designed the "normal" or "wild-type" form of the gene.

Each embodiment described herein is to be applied mutatis mutandis to each and every embodiment unless specifically stated otherwise.

2. Abbreviations

The following abbreviations are used throughout the application:
nt=nucleotide
nts=nucleotides
aa=amino acid(s)
d=day
h=hour
s=seconds 3. IGF-Containing Complex Formation-Modulating Agents The present invention is based in part on the determination that certain fragments of human VN can: (1) bind to at least one vitronectin-binding partner selected from an IGF (e.g., IGF-I and IGF-II) and an IGFBP (e.g., IGFBP-3 and IGFBP-5); (2) inhibit binding of a vitronectin to at least one vitronectin-binding partner selected from an IGF (e.g., IGF-I and IGF-II) and an IGFBP (e.g., IGFBP-3 and IGFBP-5); (3) inhibit formation of a complex comprising a vitronectin and at least one vitronectin-binding partner selected from an IGF (e.g., IGF-I and IGF-II) and an IGFBP (e.g., IGFBP-3 and IGFBP-5), illustrative examples of which include (i) a complex comprising, consisting or consisting essentially of vitronectin, IGF-I and an IGFBP; (e.g., IGFBP-3 or IGFBP-5), and (ii) a complex comprising, consisting or consisting essentially of vitronectin and IGF-II; (4) inhibit proliferation of a hyperproliferative cell (e.g., a non-neoplastic cell or a neoplastic cell such as an epithelial cancer cell); (5) inhibit migration of a hyperproliferative cell (e.g., a neoplastic cell such as an epithelial cancer cell); (6) inhibit invasion of a hyperproliferative cell (e.g., a neoplastic cell such as an epithelial cancer cell); (7) inhibit survival or viability of a hyperproliferative cell (e.g., a non-neoplastic cell or a neoplastic cell such as an epithelial cancer cell). Several orthologs of these fragments have been identified from other mammals including pig, bovine, goat, mouse, rabbit and rat. In view of their close structural similarity to their human counterparts (i.e., Peptide 1: SEQ ID NO: 2; Peptide 2: SEQ ID NO:16; Peptide 3: SEQ ID NO:30; Peptide 4: SEQ ID NO:44; Peptide 5: SEQ ID NO:58; Peptide 6: SEQ ID NO:72, Peptide 7: SEQ ID NO:86; and Peptide 8: SEQ ID NO:100), as for example shown in FIG. 1, these orthologs are considered to have the same or similar activity as their human counterparts.

Accordingly, the present invention provides VN peptide antagonists in methods and pharmaceutical compositions for eliciting any one or more of activities (1) to (7) as defined above and/or for treating or preventing conditions (e.g., hyperproliferative cell disorders) that benefit or ameliorate through elicitation of these activities. When included in pharmaceutical compositions, the VN peptide antagonists are suitably combined with a pharmaceutically acceptable carrier or diluent. The VN peptide antagonists of the present invention can be administered by any suitable route including for example subcutaneously (s.c.), intraperitoneally (i.p.), intravenously (i.v.) by direct injection into a site (e.g., an affected site such as a tumor), by topical or mucosal application, by inhalation or via the oral route including modified-release modes of administration.

In some embodiments, the VN peptide antagonists comprise, consist or consist essentially of an amino acid sequence that corresponds to a VN peptide as defined herein. Illustrative corresponding VN peptide antagonists may be obtained from any mammal including from the orders: (e.g., Monotremata, Didelphimorphia, Paucituberculata, Microbiotheria, Notoryctemorphia, Dasyuromorphia, Peramelemorphia, Diprotodontia, Tubulidentata, Sirenia, Afrosoricida, Macroscelidea, Hyracoidea, Proboscidea, Cingulata, Pilosa, Scandentia, Dermoptera, Primates, Rodentia, Lagomorpha, Erinaceomorpha, Soricomorpha, Chiroptera, Pholidota, Carnivora, Perissodactyla, Artiodactyla, Cetacea). In some embodiments, the VN peptide antagonists are produced by recombinant DNA techniques or by chemical synthesis.

The VN peptide antagonists of the present invention include peptides which arise as a result of the existence of alternative translational and post-translational events. The VN peptide antagonists can be expressed in systems, e.g., cultured cells, which result in substantially the same post-translational modifications present when VN is expressed in a native cell, or in systems which result in the alteration or omission of post-translational modifications, e.g., glycosylation or cleavage, present when expressed in a native cell.

In some embodiments, a VN peptide comprises, consists or consists essentially of an about 19-residue sequence, as shown for example in FIG. 1A, or a sequence corresponding thereto. In non-limiting examples of this type, the VN peptide may comprise: C, or modified form thereof, at position 1; Q, or modified form thereof, at position 2; C, or modified form thereof, at position 3; D, or modified form thereof, at position 4; E, or modified form thereof, at position 5; L, or modified form thereof, at position 6; C, or modified form thereof, at position 7; a small amino acid residue such as S or T, or modified form thereof, at position 8; Y, or modified form thereof, at position 9; Y, or modified form thereof, at position 10; Q, or modified form thereof, at position 11; S, or modified form thereof, at position 12; C, or modified form thereof, at position 13; C, or modified form thereof, at position 14; a small amino acid residue such as T or A, or modified form thereof, or an hydrophobic amino acid residue including an aliphatic amino acid residues such as V, or modified form thereof at position 15; D, or modified form thereof, at position 16; an hydrophobic amino acid residue including an aromatic amino acid residue such as Y or F, or modified form thereof, at position 17; a small amino acid residue such as T or A, or modified form thereof, or an hydrophobic amino acid residue including an aliphatic amino acid residue such as M or V, or modified form thereof, at position 18; and a small amino acid residue such as A, or modified form thereof, or an acidic amino acid residue such as E, or modified form thereof, at position 19, relative to the consensus numbering of FIG. 1A.

In some embodiments, a VN peptide comprises, consists or consists essentially of an about 8-residue sequence, as shown for example in FIG. 1B, or a sequence corresponding thereto. In non-limiting examples of this type, the VN peptide may comprise: T, or modified form thereof, at position 1; any amino acid residue including for example an acidic amino acid residue such as D, or modified form thereof, or a small amino acid residue such as S or T, or modified form thereof, or an hydrophobic amino acid residue including an aliphatic amino acid residue such as L, or modified forms thereof, at position 2; a charged amino acid residue including a basic amino acid residue such as H, or modified form thereof, or an acidic amino acid residue such as D or E, or modified form thereof, at position 3; any amino acid residue including for example a small amino acid residue such as P, or modified form thereof, or an hydrophobic amino acid residue including an aliphatic amino acid residue such as L, or modified form thereof, or a neutral/polar amino acid residue such as Q, or modified form thereof, or an acidic amino acid residue such as E, or modified form thereof, at position 4; G, or modified form thereof, at position 5; any amino acid residue including for example a basic amino acid residue such as R, or modified form thereof, or an hydrophobic amino acid residue including an aliphatic amino acid residue such as V, or modified form thereof, or a small amino acid residue such as T, or modified form thereof, at position 6; a small amino acid residue such as P or S, or modified form thereof, at position 7; and any amino acid residue including for example a neutral/polar amino acid residue such as Q, or modified form thereof, or an acidic amino acid residue such as E, or modified form thereof, or a small amino acid residue such as A, or modified form thereof, at position 8, relative to the consensus numbering of FIG. 1B.

In some embodiments, a VN peptide comprises, consists or consists essentially of an about 19-residue sequence, as shown for example in FIG. 1C, or a sequence corresponding thereto. In non-limiting examples of this type, the VN peptide may comprise: V, or modified form thereof, at position 1; D, or modified form thereof, at position 2; A, or modified form thereof, at position 3; A, or modified form thereof, at position 4; an hydrophobic amino acid residue including an aliphatic amino acid residue such as L, or modified form thereof, or an aromatic amino acid residue such as F, or modified form thereof, at position 5; A, or modified form thereof, at position 6; L, or modified form thereof, at position 7; P, or modified form thereof, at position 8; A, or modified form thereof, at position 9; H, or modified form thereof, at position 10; any amino acid residue including for example a small amino acid residue such as S, or modified form thereof, or a neutral/polar amino acid residue such as N, or modified form thereof, or a basic amino acid residue such as R, or modified form thereof, at position 11; an hydrophobic amino acid residue including an aromatic amino acid residue such as Y or F, or modified form thereof, at position 12; a small amino acid residue such as S, or modified form thereof, or a neutral/polar amino acid residue such as N, or modified form thereof; at position 13; G, or modified form thereof, at position 14; R, or modified form thereof, at position 15; E, or modified form thereof, at position 16; R, or modified form thereof, at position 17; V, or modified form thereof, at position 18; and Y, or modified form thereof, at position 19, relative to the consensus numbering of FIG. 1C.

In some embodiments, a VN peptide comprises, consists or consists essentially of an about 19-residue sequence, as shown for example in FIG. 1D, or a sequence corresponding thereto. In illustrative examples of this type, the VN peptide may comprise: K, or modified form thereof, at position 1; G, or modified form thereof, at position 2; a charged amino acid residue including a basic amino acid residue such as K, or modified form thereof, or an acidic amino acid residues such as D, or modified forms thereof, or a neutral/polar amino acid residue such as N, or modified form thereof, at position 3; a neutral polar amino acid residue such as Q, or modified form thereof, or a basic amino acid residue such as H or K, or modified form thereof, at position 4; Y, or modified form thereof, at position 5; W, or modified form thereof, at position 6; E, or modified form thereof, at position 7; Y, or modified form thereof, at position 8; any amino acid residue including for example a neutral/polar amino acid residue such as Q, or modified form thereof, or an hydrophobic amino acid residue including an aliphatic amino acid residue such as V, or modified form thereof, or an acidic amino acid residue such as E, or modified form thereof, at position 9; F, or modified form thereof, at position 10; Q, or modified form thereof, at position 11; a basic amino acid residue such as H, or modified form thereof, or a neutral/polar amino acid residue such as Q, or modified form thereof, at position 12; Q, or modified form thereof, at position 13; P, or modified form thereof, at position 14; S, or modified form thereof, at position 15; a neutral/polar amino acid residue such as Q, or modified form thereof, or a basic amino acid residue such as R, or modified form thereof, at position 16; E, or modified form thereof, at position 17; an acidic amino acid residue such as E or D, or modified form thereof, at position 18; and C, or modified form thereof, at position 19, relative to the consensus numbering of FIG. 1D.

In some embodiments, a VN peptide comprises, consists or consists essentially of an about 25-residue sequence, as shown for example in FIG. 1E, or a sequence corresponding thereto. In representative examples of this type, the VN peptide may comprise: F, or modified form thereof, at position 1; a charged amino acid residue including an acidic amino acid residue such as E, or modified form thereof, or a basic amino acid residue such as K or modified form thereof, or a small amino acid residue such as A, or modified form thereof, at position 2; H, or modified form thereof, at position 3; F, or modified form thereof, at position 4; A, or modified form thereof, at position 5; an hydrophobic amino acid residue including an aliphatic amino acid residue such as M or L, or modified form thereof, at position 6; an hydrophobic amino acid residue including an aliphatic amino acid residue such as M or L, or modified form thereof, at position 7; a neutral/polar amino acid residue such as Q, or modified form thereof, or a basic amino acid residue such H, or modified form thereof, at position 8; R, or modified form thereof, at position 9; D, or modified form thereof, at position 10; S, or modified form thereof, at position 11; W, or modified form thereof, at position 12; an acidic amino acid residue such as E, or modified form thereof, or an hydrophobic amino acid residue including an aliphatic amino acid residue such as V, or modified form thereof, at position 13; an acidic amino acid residue such as D, or modified form thereof, or a neutral/polar amino acid residue such as N, or modified form thereof, at position 14; I, or modified form thereof, at position 15; F, or modified form thereof, at position 16; a charged amino acid residue including a basic amino acid residue such as R or K or modified form thereof, or an acidic amino acid residue such as E, or modified form thereof, at position 17; L, or modified form thereof, at position 18; L, or modified form thereof, at position 19; F, or modified form thereof, at position 20; W, or modified form thereof, at position 21; a small amino acid residues such as G or S, or modified form thereof, at position 22; a basic amino acid residue such R or H, or modified form thereof, or a small amino acid residue such as G, or modified form thereof, at position 23; a small amino acid residue such as T, S or P, or modified form thereof, at position 24, and a small amino acid residue such as S, or modified form thereof, or an hydrophobic amino acid residue including an aromatic amino acid residue such as F or Y, or modified form thereof, at position 25, relative to the consensus numbering of FIG. 1E.

In some embodiments, a VN peptide comprises, consists or consists essentially of an about 22-residue sequence, as shown for example in FIG. 1F, or a sequence corresponding thereto. In non-limiting examples of this type, the VN peptide may comprise: a small amino acid residue such as G or S, or modified form thereof, at position 1; a basic amino acid residue such as R or H, or modified form thereof, or a small amino acid residue such as G, or modified form thereof, at position 2; a small amino acid residue such as T, S or P, or modified form thereof, at position 3; a small amino acid residue such as S, or modified form thereof, or an hydrophobic amino acid residue including an aromatic amino acid residue such as F or Y, or modified form thereof, at position 4; a small amino acid residue such as A or G, or modified form thereof, or an acidic amino acid residue such as D, or modified form thereof, at position 5; G, or modified form thereof, at position 6; a small amino acid residue such as T or A, or modified form thereof, at position 7; any amino acid residue including for example a basic amino acid residue such as R or K, or modified form thereof, or an hydrophobic amino acid residue including an aliphatic amino acid residue such as I, or modified form thereof, or a small amino acid residue such as G, or modified form thereof, at position 8; any amino acid residue including for example a neutral/polar amino acid residue such as Q, or modified form thereof, or an acidic amino acid residue such E, or modified form thereof, or a small amino acid residue such as G, or modified form thereof, at position 9; P, or modified form thereof, at position 10; a neutral/polar amino acid residue such as Q, or modified form thereof, or a basic amino acid residue such R, or modified form thereof, at position 11; an hydrophobic amino acid residue including an aromatic amino acid residue such as F, or modified form thereof, or an aliphatic amino acid residue such as V or L, or modified form thereof, at position 12; I, or modified form thereof, at position 13; S, or modified form thereof, at position 14; a basic amino acid residue such R, or modified form thereof, or a neutral/polar amino acid residue such as Q, or modified form thereof, at position 15; an acidic amino acid residue such D, or modified form thereof neutral polar amino acid residues such as N, or modified forms thereof, at position 16; W, or modified form thereof, at position 17; a basic amino acid residue such as H, or modified form thereof, or an hydrophobic amino acid residue including an aliphatic amino acid residue such as L, or modified form thereof, or an aromatic amino acid residue such as F, or modified form thereof, at position 18; G, or modified form thereof, at position 19; an hydrophobic amino acid residue including an aliphatic amino acid residue such as V or L, or modified form thereof, at position 20; P, or modified form thereof, at position 21; and a small amino acid residue such as G, or modified form thereof, or an acidic amino acid residue such E, or modified form thereof, at position 22, relative to the consensus numbering of FIG. 1F.

In some embodiments, a VN peptide comprises, consists or consists essentially of an about 22-residue sequence, as shown for example in FIG. 1G, or a sequence corresponding thereto. In non-limiting examples of this type, the VN peptide may comprise: an hydrophobic amino acid residue including an aliphatic amino acid residue such as L, or modified form thereof or an aromatic amino acid residue such as W, or modified form thereof, at position 1; an hydrophobic amino acid residue including an aliphatic amino acid residue such as L, or modified form thereof or an aromatic amino acid residue such as F, or modified form thereof, at position 2; S, or modified form thereof, at position 3; S, or modified form thereof, at position 4; E, or modified form thereof, at position 5; E, or modified form thereof, at position 6; a small amino acid residue such as S or T, or modified form thereof, or an hydrophobic amino acid residue including an aliphatic amino acid residue such as L or V, or modified form thereof, at position 7; a small amino acid residue such as G or S, or modified form thereof, or a neutral/polar amino acid residue such as N, or modified form thereof, at position 8; a small amino acid residue such as P, or modified form thereof, or an hydrophobic amino acid residue including an aliphatic amino acid residue such as L, or modified form thereof, at position 9; G, or modified form thereof, at position 10; a small amino acid residue such as P, A, G or T, or modified form thereof, at position 11; any amino acid residue including for example a neutral/polar amino acid residue such as N, or modified form thereof, or an acidic amino acid residue such as D, or modified form thereof, or an hydrophobic amino acid residue including an aromatic amino acid residue such as Y, or modified form thereof, at position 12; N, or modified form thereof, at position 13; no amino acid residue or a neutral/polar amino acid residue such as N, or modified form thereof, or an hydrophobic amino acid residue including an aromatic amino acid residue such Y, or modified form thereof, at position 14; an acidic amino acid residue such as E or D, or modified form thereof, or an hydrophobic amino acid residue including an aromatic amino acid residue such as Y, or modified form thereof, at position 15; any amino acid residue including for example an acidic amino acid residue such as D, or modified form thereof, or a neutral/polar amino acid residue such as N, or modified form thereof, or a small amino acid residue such as S, or modified form thereof, at position 16; an hydrophobic amino acid residue including an aromatic amino acid residue such as Y or F, or modified form thereof, at position 17; a charged amino acid residue including a basic amino acid residue such as K or R, or modified form thereof, or an acidic amino acid residue such as E or D, or modified form thereof, at position 18; an hydrophobic amino acid residue including an aliphatic amino acid residues such as M, or modified form thereof, or a small amino acid residue such as T, or modified form thereof, at position 19; any amino acid residue including for example an acidic amino acid residue such as D, or modified form thereof, or a small amino acid residue such as S, or modified form thereof, or a neutral/polar amino acid residue such as N, or modified forms thereof, at position 20; W, or modified form thereof, at position 21; and L, or modified form thereof, at position 22, relative to the consensus numbering of FIG. 1G.

In some embodiments, a VN peptide comprises, consists or consists essentially of an about 19-residue sequence, as shown for example in FIG. 1H, or a sequence corresponding thereto. In illustrative examples of this type, the VN peptide may comprise: R, or modified form thereof, at position 1; V, or modified form thereof, at position 2; N, or modified form thereof, at position 3; L, or modified form thereof, at position 4; R, or modified form thereof, at position 5; T, or modified form thereof, at position 6; a basic amino acid residue such as R, or modified form thereof, or a neutral/polar amino acid residue such as Q, or modified form thereof, at position 7; R, or modified form thereof, at position 8; V, or modified form thereof, at position 9; D, or modified form thereof, at position 10; a small amino acid residue such as S, A or T, or modified form thereof, at position 11; V, or modified form thereof, at position 12; any amino acid residue including for example an acidic amino acid residue such as D, or modified form thereof, or a small amino acid residue such as T, or modified form thereof, or a neutral/polar amino acid residue such as N, or modified form thereof, or an hydrophobic amino acid residue including an aliphatic amino acid residue such as I, or modified form thereof, at position 13; P, or modified form thereof, at position 14; P, or modified form thereof, at position 15; Y, or modified form thereof, at position 16; P, or modified form thereof, at position 17; R, or modified form thereof, at position 18; S, and modified form thereof, at position 19; relative to the consensus numbering of FIG. 1H.

The present invention also contemplates VN peptide antagonists that are variants of reference VN peptide antagonists, defined for example above. Such "variant" peptides include peptides derived from the reference VN peptide antagonists by deletion (so-called truncation) of one or more amino acids to their N-terminal and/or C-terminal ends; or by substitution, addition or deletion of one or more amino acids in the reference VN peptide antagonists. In some embodiments, variant VN peptide antagonists may have as much as 1, 2, 3, 4, or 5 amino acids deleted from their N-terminal and/or C-terminal ends. In some embodiments, variant VN peptide antagonists may comprise at least 1, 2, 3, 4, 5, 6, 7, 8, 9, 10, 11, 12, 13, 14, 15, 16, 17, 18, 19, 20, 21, 22, 23, 24, 25, 26, 28, 29, 30, 31, 32, 33, 34, 35, 36, 37, 38, 39, 40, 41, 42, 43, 44, 45, 46, 47, 48, 49, 50 or more upstream (i.e. extending from the N-terminus of a reference peptide) and/or downstream (i.e. extending from the C-terminus of a reference peptide) amino acids. In some embodiments, variant VN peptide antagonists may have as much as 1, 2, 3, 4, or 5 amino acids deleted in a reference VN peptide. In some embodiments, variant VN peptide antagonists may have as much as 1, 2, 3, 4, or 5 amino acids inserted in a reference VN peptide. Suitably, these variant peptides have no less than about 20%, 30%, 40%, 50%, 60%, 70% or 80% of at least one of the activities or characteristics (i.e., (1) to (7) defined above) of a reference VN peptide.

Accordingly, a VN peptide may be altered in various ways including amino acid substitutions, deletions, truncations, and insertions. Methods for such manipulations are generally known in the art. For example, amino acid sequence variants of reference VN peptide antagonists can be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol.*, 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of a peptide or protein of interest may be found in the model of Dayhoff et al., (1978) Atlas of Protein Sequence and Structure (Natl. Biomed. Res. Found., Washington, D.C.). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of VN peptide antagonists. Recursive ensemble mutagenesis (REM), a technique which enhances the frequency of functional mutants in the libraries, can be used in combination with the screening assays to identify VN peptide variants (Arkin and Yourvan (1992) *Proc. Natl. Acad. Sci. USA* 89: 7811-7815; Delgrave et al., (1993) *Protein Engineering*, 6: 327-331). Conservative substitutions, such as exchanging one amino acid with another having similar properties, may be desirable as discussed in more detail below.

Variant VN peptide antagonists may contain conservative amino acid substitutions at various locations along their sequence, as compared to a reference VN amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., (1978), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (1992, *Science*, 256(5062): 14430-1445), however, include proline in the same group as glycine, serine, alanine and threonine. Accordingly, for the purposes of the present invention, proline is classified as a "small" amino acid.

The degree of attraction or repulsion required for classification as polar or non-polar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table 3.

TABLE 3

AMINO ACID SUB-CLASSIFICATION

| SUB-CLASSES | AMINO ACIDS |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Nonpolar/neutral | Alanine, Glycine, Isoleucine, Leucine, Methionine, Phenylalanine, Proline, Tryptophan, Valine |
| Polar/neutral | Asparagine, Histidine, Glutamine, Cysteine, Serine, Threonine, Tyrosine |
| Polar/negative | Aspartic acid, Glutamic acid |
| Polar/positive | Lysine, Arginine |
| Polar/large | Asparagine, Glutamine |
| Polar | Arginine, Asparagine, Aspartic acid, Cysteine, Glutamic acid, Glutamine, Histidine, Lysine, Serine, Threonine, Tyrosine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional VN peptide can readily be determined by assaying its activity (e.g., an activity selected from activities (1) to (7) as defined above). Conservative substitutions are shown in Table 4 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 4

EXEMPLARY AND PREFERRED AMINO ACID SUBSTITUTIONS

| ORIGINAL RESIDUE | EXEMPLARY SUBSTITUTIONS | PREFERRED SUBSTITUTIONS |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm. C. Brown Publishers (1993).

Thus, a predicted non-essential amino acid residue in a VN peptide is typically replaced with another amino acid residue from the same side chain family. Alternatively, mutations can be introduced randomly along all or part of a coding sequence for a reference VN peptide, such as by saturation mutagenesis, and the resultant mutants can be screened for an activity of the reference VN peptide to identify mutants which retain that activity. Following mutagenesis of the coding sequences, the encoded peptide can be expressed recombinantly or synthesized chemically and its activity determined. A "non-essential" amino acid residue is a residue that can be altered from a reference sequence of an embodiment peptide without abolishing or substantially altering one or more of its activities. Suitably, the alteration does not substantially alter one of these activities, for example, the activity is at least 20%, 30%, 40%, 50%, 60%, 70% or 80% of the reference peptide. Illustrative non-essential amino acid residues include any one or more of the amino acid residues that differ at the same position (e.g., residues $X_1$-$X_5$ of formula I as defined supra, residues $X_1$-$X_6$ of formula II as defined supra, residues $X_1$-$X_4$ of formula III as defined supra, residues $X_1$-$X_6$ of formula IV as defined supra, residues $X_1$-$X_{11}$ of formula V as defined supra, residues $X_1$-$X_{15}$ of formula VI as defined supra, residues $X_1$-$X_{14}$ of formula VII as defined supra, or residues $X_1$-$X_3$ of formula VIII as defined supra) between the wild-type sequences corresponding to the VN peptide antagonists shown in FIG. 1A-H.

By contrast, an "essential" amino acid residue is a residue that, when altered from the wild-type sequence of a reference VN peptide, results in abolition of an activity of the parent molecule such that less than 20% of the wild-type activity is present. For example, such essential amino acid residues include those that are conserved in VN peptide antagonists across different species, e.g., (1) C, or modified form thereof, at position 1; Q, or modified form thereof, at position 2; C, or modified form thereof, at position 3; D, or modified form thereof, at position 4; E, or modified form thereof, at position 5; L, or modified form thereof, at position 6; C, or modified form thereof, at position 7; Y, or modified form thereof, at position 9; Y, or modified form thereof, at position 10; Q, or modified form thereof, at position 11; S, or modified form thereof, at position 12; C, or modified form thereof, at position 13; C, or modified form thereof, at position 14; or D, or modified form thereof, at position 16 (relative to the consensus numbering of FIG. 1A) of peptides according to formula I; (2) T, or modified form thereof, at position 1; or G, or modified form thereof, at position 5 (relative to the consensus numbering of FIG. 1B) of peptides according to formula II; (3) V, or modified form thereof, at position 1; D, or modified form thereof, at position 2; A, or modified form thereof, at position 3; A, or modified form thereof, at position 4; A, or modified form thereof, at position 6; L, or modified form thereof, at position 7; P, or modified form thereof, at position 8; A, or modified form thereof, at position 9; H, or modified form thereof, at position 10; G, or modified form thereof, at position 14; R, or modified form thereof, at position 15; E, or modified form thereof, at position 16; R, or modified form thereof, at position 17; V, or modified form thereof, at position 18; or Y, or modified form thereof, at position 19 (relative to the consensus numbering of FIG. 1C) of peptides according to formula III; (4) K, or modified form thereof, at position 1; G, or modified form thereof, at position 2; Y, or modified form thereof, at position 5; W, or modified form thereof, at position 6; E, or modified form thereof, at position 7; Y, or modified form thereof, at position 8; F, or modified form thereof, at position 10; Q, or modified form thereof, at position 11; Q, or modified form thereof, at position 13; P, or modified form thereof, at position 14; S, or modified form thereof, at position 15; or E, or modified form thereof, at position 17; or C, or modified form thereof at position 19 (relative to the consensus numbering of FIG. 1D) of peptides according to formula IV; (5) F, or modified form thereof, at position 1; H, or modified form thereof, at position 3; F, or modified form thereof, at position 4; A, or modified form thereof, at position 5; R, or modified form thereof, at position 9; D, or modified form thereof, at position 10; S, or modified form thereof, at position 11; W, or modified form thereof, at position 12; I, or modified form thereof, at position 15; F, or modified form thereof, at position 16; L, or modified form thereof, at position 18; L, or modified form thereof, at position 19; F, or modified form thereof, at position 20; or W, or modified form thereof, at position 21 (relative to the consensus numbering of FIG. 1E) of peptides according to formula V; (6) G, or modified form thereof, at position 6; P, or modified form thereof, at position 10; I, or modified form thereof, at position 13; S, or modified form thereof, at position 14; W, or modified form thereof, at position 17; G, or modified form thereof, at position 19; or P, or modified form thereof, at position 21 (relative to the consensus numbering of FIG. 1F) of peptides according to formula VI; (7) S, or modified form thereof, at position 3; S, or modified form thereof, at position 4; E, or modified form thereof, at position 5; E, or modified form thereof, at position 6; G, or modified form thereof, at position 10; N, or modified form thereof, at position 13; W, or modified form thereof, at position 21; or L, or modified form thereof, at position 22 (relative to the consensus numbering of FIG. 1G) of peptides according to formula VII; (8) R, or modified form thereof, at position 1; V, or modified form thereof, at position 2; N, or modified form thereof, at position 3; L, or modified form thereof, at position 4; R, or modified form thereof, at position 5; T, or modified form thereof, at position 6; R, or modified form thereof, at position 8; V, or modified form thereof, at position 9; D, or modified form thereof, at position 10; V, or modified form thereof, at position 12; P, or modified form thereof, at position 14; P, or modified form thereof, at position 15; Y, or modified form thereof, at position 16; P, or modified form thereof, at position 17; R, or modified form thereof, at position 18; or S, or modified form thereof, at position 19; (relative to the consensus numbering of FIG. 1H) of peptides according to formula VIII.

Accordingly, the present invention also contemplates as VN peptide antagonists, variants of the naturally-occurring VN peptide sequences, wherein the variants are distinguished from the naturally-occurring sequence by the addition, deletion, or substitution of one or more amino acid residues. In general, variants will display at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% similarity to a parent or reference VN peptide sequence as, for example, set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110 or 112, as determined by sequence alignment programs described elsewhere herein using default parameters. Desirably, variants will have at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to a parent VN peptide sequence as, for example, set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110 or 112, as determined by sequence alignment programs described elsewhere herein using default parameters. Variants of a wild-type VN peptide, which fall within the scope of a variant peptide, may differ from the wild-type peptide generally by as much 15, 14, 13, 12, or 11 amino acid residues or suitably by as few as 10, 9, 8, 7, 6, 5 4, 3, 2, or 1 amino acid residue(s). In some embodiments, a variant peptide differs from the corresponding sequences as set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110 or 112 by at least 1 but by less than or equal to 10, 9, 8, 7, 6, 5, 4, 3 or 2 amino acid residues. In other embodiments, it differs from the corresponding sequence as set forth in any one of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110 or 112 by at least 1% but less than or equal to 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3% or 2% of the residues. If the sequence comparison requires alignment, the sequences are typically aligned for maximum similarity or identity. "Looped" out sequences from deletions or insertions, or mismatches, are generally considered differences. The differences are, suitably, differences or changes at a non-essential residue or a conservative substitution, as discussed above.

The VN peptide antagonists of the present invention also encompass VN peptide antagonists comprising amino acids with modified side chains, incorporation of unnatural amino acid residues and/or their derivatives during peptide, polypeptide or protein synthesis and the use of cross-linkers and other methods which impose conformational constraints on the peptides, portions and variants of the invention. Examples of side chain modifications include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with NaBH$_4$; reductive alkylation by reaction with an aldehyde followed by reduction with NaBH$_4$; and trinitrobenzylation of amino groups with 2, 4, 6-trinitrobenzene sulfonic acid (TNBS).

The carboxyl group may be modified by carbodiimide activation via O-acylisourea formation followed by subsequent derivatization, by way of example, to a corresponding amide.

The guanidine group of arginine residues may be modified by formation of heterocyclic condensation products with reagents such as 2,3-butanedione, phenylglyoxal and glyoxal.

Sulfhydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulfides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulfonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in Table 5.

TABLE 5

NON-CONVENTIONAL AMINO ACIDS
Non-Conventional Amino Acids

| | |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carboxy-1-(2,2-diphenyl-ethyl amino)cyclopropane | |

Variant VN peptide antagonists also encompass: (1) peptides whose amino group at the N-terminal amino acid residue (e.g., methionine residue) is protected with a protecting group (e.g., a $C_{1-6}$ acyl group such as a $C_{1-6}$ alkanoyl group, e.g., formyl group, acetyl group, etc.); (2) peptides whose N-terminal region is cleaved in vivo and the glutamyl group thus formed is pyroglutaminated; (3) peptides whose substituents (e.g., —OH, —SH, amino group, imidazole group, indole group, guanidino group, etc.) on the side chains of amino acids in the molecule are protected with suitable protecting groups (e.g., a $C_{16}$ acyl group such as a $C_{1-6}$ alkanoyl group, e.g., formyl group, acetyl group, etc.), (4) peptides whose carboxyl group at the C-terminal amino acid residue is protected by a protecting group (e.g., an ester or ketone-forming alkyl groups, such as lower ($C_1$ to $C_6$) alkyl groups, for example methyl, ethyl and propyl, and amide-forming amino groups, such as primary amines (—NH$_2$), and mono- and di-alkylamino groups, such as methylamino, ethylamino, dimethylamino, diethylamino, methylethylamino, and the like); (5) peptides whose C-terminus comprises a descarboxylated amino acid analogue; (6) peptides whose side chains have been modified to include a carbohydrate, polyethylene glycol (PEG) or other polymer; or (7) cyclic peptides having an intramolecular (e.g., covalent or non-covalent) bond between two non-adjacent amino acids (e.g., through backbone to backbone, side-chain to backbone or side-chain to side-chain bonds); etc.

The VN peptide antagonists of the present invention also include peptides that are encoded by polynucleotides that hybridize under stringency conditions as defined herein, especially medium or high stringency conditions, to VN-encoding polynucleotide sequences, or the non-coding strand thereof, as described below. Illustrative VN polynucleotide sequences are set forth in SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109 or 111, or their complements. These nucleotide sequences are presented in Table 8 infra.

In some embodiments, calculations of sequence similarity or sequence identity between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 30%, usually at least 40%, more usually at least 50%, 60%, and even more usually at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. For amino acid sequence comparison, when a position in the first sequence is occupied by the same or similar amino acid residue (i.e., conservative substitution) at the corresponding position in the second sequence, then the molecules are similar at that position.

The percent identity between the two sequences is a function of the number of identical amino acid residues shared by the sequences at individual positions, taking into account the number of gaps, and the length of each gap, which need to be introduced for optimal alignment of the two sequences. By contrast, the percent similarity between the two sequences is a function of the number of identical and similar amino acid residues shared by the sequences at individual positions, taking into account the number of gaps, and the length of each gap, which need to be introduced for optimal alignment of the two sequences.

The comparison of sequences and determination of percent identity or percent similarity between sequences can be accomplished using a mathematical algorithm. In certain embodiments, the percent identity or similarity between amino acid sequences is determined using the Needleman and Wunsch, (1970, *J. Mol. Biol.* 48: 444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In specific embodiments, the percent identity between nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. An non-limiting set of parameters (and the one that should be used unless otherwise specified) includes a Blossum 62 scoring matrix with a gap penalty of 12, a gap extend penalty of 4, and a frameshift gap penalty of 5.

In some embodiments, the percent identity or similarity between amino acid or nucleotide sequences can be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to 53010 nucleic acid molecules of the invention. BLAST protein searches can be performed with the XBLAST program, score=50, wordlength=3 to obtain amino acid sequences homologous to 53010 protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

Variants of a reference VN peptide can be identified by screening combinatorial libraries of mutants, e.g., truncation mutants, of a VN peptide. Libraries or fragments e.g., N terminal, C terminal, or internal fragments, of a VN-coding sequence can be used to generate a variegated population of fragments for screening and subsequent selection of variants of a reference VN peptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of VN peptide antagonists.

The VN peptide antagonists of the present invention may be prepared by any suitable procedure known to those of skill in the art. For example, the VN peptide antagonists may be synthesized by chemical synthesis, e.g., using solution synthesis or solid phase synthesis as described, for example, in Chapter 9 of Atherton and Shephard (supra) and in Roberge et al., (1995, *Science*, 269: 202). Alternatively, the VN peptide antagonists may be prepared by recombinant techniques. For example, the VN peptide antagonists of the invention may be prepared by a procedure including the steps of: (a) preparing a construct comprising a polynucleotide sequence that encodes a VN peptide and that is operably linked to a regulatory element; (b) introducing the construct into a host cell; (c) culturing the host cell to express the polynucleotide sequence to thereby produce the encoded VN peptide; and (d) isolating the VN peptide from the host cell. In illustrative examples, the nucleotide sequence encodes any one of the sequences set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110 or 112, or a variant thereof. Recombinant VN peptide antagonists can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

The present invention also contemplates VN peptide antagonist chimeric or fusion proteins. As used herein, a VN peptide antagonist "chimeric protein" or "fusion protein" includes a VN peptide antagonist peptide linked to a non-VN peptide antagonist peptide or polypeptide. A "non-VN peptide antagonist peptide or polypeptide" refers to a peptide or polypeptide having an amino acid sequence corresponding to a protein which is different from a VN peptide antagonist peptide and which is derived from the same or a different organism. The non-VN peptide antagonist peptide or polypeptide can be fused to the N-terminus or C-terminus of the VN peptide antagonist peptide. In specific embodiments, the chimeric or fusion protein is a synthetic chimeric or fusion protein.

The fusion protein can include a moiety which has a high affinity for a ligand. For example, the fusion protein can be a GST-VN peptide antagonist peptide fusion protein in which the VN peptide antagonist peptide sequence is fused to the C-terminus of the GST sequence. Such fusion proteins can facilitate the purification of recombinant VN peptide antagonist peptides. Alternatively, the fusion protein can be a VN peptide antagonist peptide containing a heterologous signal sequence at its N-terminus. In certain host cells (e.g., mammalian host cells), expression and/or secretion of VN peptide antagonist peptides can be increased through use of a heterologous signal sequence. In some embodiments, fusion proteins may include all or a part of a serum protein, e.g., an IgG constant region, or human serum albumin.

The invention also contemplates variants of the VN peptide-encoding nucleotide sequences. Nucleic acid variants can be naturally-occurring, such as allelic variants (same locus), homologs (different locus), and orthologs (different organism) or can be non naturally-occurring. Naturally-occurring nucleic acid variants (also referred to herein as polynucleotide variants) such as these can be identified with the use of well-known molecular biology techniques, as, for example, with polymerase chain reaction (PCR) and hybridization techniques as known in the art. Non-naturally occurring polynucleotide variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference VN peptide. Variant nucleotide sequences also include synthetically derived nucleotide sequences, such as those generated, for example, by using site-directed mutagenesis but which still encode a VN peptide. Generally, variants of a particular VN peptide coding sequence will have at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to that particular nucleotide sequence as determined by sequence alignment programs described elsewhere herein using default parameters. In some embodiments, the VN peptide coding sequence displays at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to a nucleotide sequence selected from any one of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109 or 111, or their complements.

VN peptide-coding sequences can be used to isolate corresponding sequences and alleles from other organisms, particularly other mammals. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other VN peptide-coding sequences present in a population of cloned genomic DNA fragments or cDNA fragments (i.e., genomic or cDNA libraries) from a chosen organism (e.g., a mammal). Accordingly, the present invention also contemplates polynucleotides that hybridize to reference VN peptide-coding sequences, or to their complements, (e.g., SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109 or 111, or their complements) under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, a VN peptide as described herein is encoded by a polynucleotide that hybridizes to a disclosed nucleotide sequence under very high stringency conditions. One embodiment of very high stringency conditions includes hybridizing 0.5 M sodium phosphate, 7% SDS at 65° C., followed by one or more washes at 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the T$_m$ for formation of a DNA-DNA hybrid. It is well known in the art that the T$_m$ is the melting temperature, or temperature at which two complementary polynucleotide sequences dissociate. Methods for estimating T$_m$ are well known in the art (see Ausubel et al., supra at page 2.10.8). In general, the T$_m$ of a perfectly matched duplex of DNA may be predicted as an approximation by the formula:

$$T_m = 81.5 + 16.6 \ (\log_{10} M) + 0.41 \ (\% \ G+C) - 0.63 \ (\% \ \text{formamide}) - (600/\text{length})$$

wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The T$_m$ of a duplex DNA decreases by approximately 1° C. with every increase of 1% in the number of randomly mismatched base pairs. Washing is generally carried out at T$_m$-15° C. for high stringency, or T$_m$-30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% Ficoll™, 0.1% polyvinylpyrrolidone and 0.1% bovine serum albumin), 0.1% SDS and 200 mg/mL denatured salmon sperm DNA) containing labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

4. Biological Assays

VN peptide antagonists of the present invention may be characterized in a variety of ways well-known to one of skill in the art. In particular, VN peptide antagonists of may be assayed for the ability to:

(1a) bind to an IGF (e.g., IGF-I or IGF-II);

(1b) bind to one or more IGFBP selected from IGFBP-1, IGFBP-2, IGFBP-3, IGFBP-4 and IGFBP-5 (e.g., IGFBP-3 or IGFBP-5);

(2a) inhibit binding of VN to one or more IGFBP selected from IGFBP-1, IGFBP-2, IGFBP-3, IGFBP-4 and IGFBP-5 (e.g., IGFBP-3 or IGFBP-5);

(2b) inhibit binding of VN to IGF-II;

(3a) inhibit formation of a complex comprising IGF-I, an IGFBP selected from IGFBP-1, IGFBP-2, IGFBP-3, IGFBP-4 and IGFBP-5 (e.g., IGFBP-3 or IGFBP-5) and VN (also referred to herein as a "trimeric complex");

(3b) inhibit formation of a complex comprising IGF-II and VN (also referred to herein as a "dimeric complex");

(4) inhibit proliferation of a hyperproliferative cell (e.g., a non-neoplastic cell or a neoplastic cell such as an epithelial cancer cell), (5) inhibit migration of a hyperproliferative cell (e.g., a neoplastic cell such as an epithelial cancer cell);

(6) inhibit invasion of a hyperproliferative cell (e.g., a neoplastic cell such as an epithelial cancer cell);

(7) inhibit survival or viability of a hyperproliferative cell (e.g., a non-neoplastic cell or a neoplastic cell such as an epithelial cancer cell); and (8) treat or prevent a hyperproliferative cell disorder (e.g., non-neoplastic disorder or a neoplastic disorder such as an epithelial cancer).

The VN peptide antagonists of the invention may be assayed for specific binding to a cognate binding partner (e.g., an IGF or an IGFBP) by any method known in the art. Immunoassays which can be used to analyze specific binding include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well-known in the art (see, e.g., Ausubel et al., eds., 1994, Current Protocols in Molecular Biology, Vol. 1, John Wiley & Sons, Inc., New York, which is incorporated by reference herein in its entirety). In some embodiments, a putative VN peptide antagonist is assayed for binding to a cognate binding partner using ELISA. In illustrative examples of this type, a putative VN peptide antagonist is contacted to a microtitre plate whose bottom surface has been coated with a target VN-binding partner, e.g., a limiting amount of the target. The plate is washed with buffer to remove non-specifically bound peptide. Then the amount of the binding peptide bound to the target on the plate is determined by probing the plate with an antibody that can recognize the binding peptide, e.g., a tag or constant portion of the binding peptide. The antibody is linked to a detection system (e.g., an enzyme such as alkaline phosphatase or horse radish peroxidase (HRP) which produces a colorimetric product when appropriate substrates are provided).

In other embodiments, the ability of a candidate VN peptide antagonist to bind a target VN binding partner is analyzed using an homogenous assay, i.e., after all components of the assay are added, additional fluid manipulations are not required. For example, fluorescence resonance energy transfer (FRET) can be used as a homogenous assay (see, e.g., U.S. Pat. No. 5,631,169; and U.S. Pat. No. 4,868,103). A fluorophore label on the first molecule (e.g., the candidate VN peptide antagonist) is selected such that its emitted fluorescent energy can be absorbed by a fluorescent label on a second molecule (e.g., the target VN-binding partner) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means, e.g., using a fluorimeter. By titrating the amount of the first or second binding molecule, a binding curve can be generated to estimate the equilibrium binding constant.

In other embodiments, the interaction between a candidate VN peptide antagonist and a target VN binding partner is analyzed using Surface Plasmon Resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether, 1988. *Surface Plasmons Springer Verlag*; Sjolander and Urbaniczky, 1991. *Anal. Chem.* 63:2338-2345; Szabo et al., 1995. *Cum Opin. Struct. Biol.* 5:699-705 and on-line resources provide by BIAcore International AB (Uppsala, Sweden).

VN peptide antagonists, or compositions of the invention are suitably tested in vitro and/or in vivo for the desired therapeutic or prophylactic activity prior to use in humans. For example, assays which can be used to determine whether administration of a specific pharmaceutical composition is indicated include cell culture assays in which a patient tissue sample is grown in culture and exposed to, or otherwise contacted with, a pharmaceutical composition, and the effect of such composition upon the tissue sample is observed. The tissue sample can be obtained by biopsy from the patient. This test allows the identification of the therapeutically most effective therapy (e.g., prophylactic or therapeutic agent) for each individual patient. In various specific embodiments, in vitro assays can be carried out with representative cells of cell types involved a particular hyperproliferative cell disorder to determine if a pharmaceutical composition of the invention has a desired effect upon such cell types. For example, in vitro assay can be carried out with cell lines.

VN peptide antagonists, compositions, or combination therapies of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the therapies (e.g., prophylactic and/or therapeutic agents) whether such therapies are administered separately or as an admixture, and the frequency of administration of the therapies.

Animal models can be used to assess the efficacy of the VN peptide antagonists, compositions, or combination therapies of the invention for treating, managing, preventing, or ameliorating a particular hyperproliferative cell disorder or one or more symptoms thereof.

The administration of VN peptide antagonists, compositions, or combination therapies according to the methods of the invention can be tested for their ability to decrease the time course of a particular hyperproliferative cell disorder by at least 25%, suitably at least 50%, at least 60%, at least 75%, at least 85%, at least 95%, or at least 99%. The VN peptide antagonists, compositions, or combination therapies of the invention can also be tested for their ability to increase the survival period of humans suffering from a particular disorder by at least 25%, preferably at least 50%, at least 60%, at least 75%, at least 85%, at least 95%, or at least 99%. Further, VN peptide antagonists, compositions, or combination therapies of the invention can be tested for their ability reduce the hospitalization period of humans suffering from hyperproliferative cell disorders by at least 60%, preferably at least 75%, at least 85%, at least 95%, or at least 99%. Techniques known to those of skill in the art can be used to analyze the function of the antibodies, compositions, or combination therapies of the invention in vivo.

The toxicity and/or efficacy of the prophylactic and/or therapeutic protocols of the instant invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in mammals, including humans. The dosage of such agents lies suitably within a range of circulating concentrations that include the ED50 with little or no toxicity. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5. Pharmaceutical Compositions

In accordance with the present invention, it is proposed that the VN peptide antagonists of the invention are useful as actives for (1) binding to at least one vitronectin-binding partner selected from an IGF (e.g., IGF-I and IGF-II) and an IGFBP (e.g., IGFBP-3 and IGFBP-5); (2) inhibiting binding of a vitronectin to at least one vitronectin-binding partner selected from an IGF (e.g., IGF-I and IGF-II) and an IGFBP (e.g., IGFBP-3 and IGFBP-5); (3) inhibiting formation of a complex comprising a vitronectin and at least one vitronectin-binding partner selected from an IGF (e.g., IGF-I and IGF-II) and an IGFBP (e.g., IGFBP-3 and IGFBP-5); (4) inhibiting proliferation of a hyperproliferative cell (e.g., a non-neoplastic cell or a neoplastic cell such as an epithelial cancer cell); (5) inhibiting migration of a hyperproliferative cell (e.g., a neoplastic cell such as an epithelial cancer cell); (6) inhibiting invasion of a hyperproliferative cell (e.g., a neoplastic cell such as an epithelial cancer cell); and/or (7) inhibiting survival or viability of a hyperproliferative cell (e.g., a non-neoplastic cell or a neoplastic cell such as an epithelial cancer cell). Thus, VN peptide antagonist compounds, in accordance with the present invention, are useful, suitably in pharmaceutical compositions, for treating or preventing conditions that benefit from or are ameliorable with any one or more of these activities, including hyperproliferative cell disorders. In specific embodiments, therefore, the present invention contemplates pharmaceutical compositions for treating, preventing and/or relieving the symptoms of a hyperproliferative cell disorder, wherein the compositions comprise an effective amount of at least one VN peptide antagonist and a pharmaceutically acceptable carrier and/or diluent. In specific embodiments, the term "pharmaceutically acceptable" means approved by a regulatory agency of the Federal or a state government or listed in a generally recognized pharmacopeia for use in animals, and more particularly in mammals, including humans. The term "carrier" refers to a diluent, adjuvant (e.g., Freund's adjuvant (complete and incomplete)), excipient, or vehicle with which the therapeutic is contained in or administered. Such pharmaceutical carriers can be sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Any VN peptide antagonist can be used in the compositions and methods of the present invention, provided that the antagonist is pharmaceutically active. A "pharmaceutically active" VN peptide antagonist is in a form that results in a reduction, impairment or abrogation in the proliferation, migration, invasion, survival or viability of a hyperproliferative cell and/or in the treatment and/or prevention of a hyperproliferative cell disorders, including the prevention of incurring a symptom, holding in check such symptoms or treating existing symptoms associated with the hyperproliferative cell disorders, when administered to an individual in need thereof.

Modes of administration, amounts of VN peptide antagonist administered, and VN peptide antagonist compositions, for use in the methods of the present invention, are routine and within the skill of practitioners in the art. Whether a hyperproliferative cell disorder has been treated is determined by measuring one or more diagnostic parameters indicative of the course of the disease, compared to a suitable control. In the case of an animal experiment, a "suitable control" is an animal not treated with the VN peptide antagonist, or treated with the pharmaceutical composition without the VN peptide antagonist. In the case of a human subject, a "suitable control" may be the individual before treatment, or may be a human (e.g., an age-matched or similar control) treated with a placebo. In accordance with the present invention, the treatment of a hyperproliferative cell disorder includes and encompasses without limitation: (i) preventing or reducing proliferation, migration, invasion, survival or viability of a hyperproliferative cell in a patient i.e., arresting its development; (ii) treating or preventing a hyperproliferative cell disorder experienced by a subject which may be predisposed to the condition but has not yet been diagnosed with the condition and, accordingly, the treatment constitutes prophylactic treatment for the pathologic condition; or (iii) causing regression of a hyperproliferative cell disorder.

The compositions and methods of the present invention are thus suitable for treating an individual who has been diagnosed with a hyperproliferative cell disorder, who is suspected of having a hyperproliferative cell disorder, who is known to be susceptible and who is considered likely to develop a hyperproliferative cell disorder, or who is considered likely to develop a recurrence of a previously treated hyperproliferative cell disorder.

In some embodiments, and dependent on the intended mode of administration, the VN peptide antagonist-containing compositions will generally contain about 0.000001% to 90%, about 0.0001% to 50%, or about 0.01% to about 25%, by weight of VN peptide antagonist, the remainder being suitable pharmaceutical carriers or diluents etc. The dosage of the VN peptide antagonist can depend on a variety of factors, such as mode of administration, the species of the affected subject, age, sex, weight and general health condition, and can be easily determined by a person of skill in the art using standard protocols. The dosages will also take into consideration the binding affinity of the VN peptide antagonist to its target molecule, its bioavailability and its in vivo and pharmacokinetic properties. In this regard, precise amounts of the agents for administration can also depend on the judgment of the practitioner. In determining the effective amount of the agents to be administered in the treatment or prevention of a hyperproliferative cell disorder, the physician or veterinarian may evaluate the progression of the disease or condition over time. In any event, those of skill in the art may readily determine suitable dosages of the agents of the invention without undue experimentation. The dosage of the actives administered to a patient should be sufficient to effect a beneficial response in the patient over time such as impairment or abrogation in the proliferation, migration, invasion, survival or viability of hyperproliferative cells and/or in the treatment and/or prevention of a hyperproliferative cell disorder. The dosages may be administered at suitable intervals to ameliorating the symptoms of the hematologic malignancy. Such intervals can be ascertained using routine procedures known to persons of skill in the art and can vary depending on the type of active agent employed and its formulation. For example, the interval may be daily, every other day, weekly, fortnightly, monthly, bimonthly, quarterly, half-yearly or yearly.

For any compound used in the method of the invention, the therapeutically effective dose can be estimated initially from cell culture assays. For example, a dose can be formulated in animal models to achieve a circulating concentration range that includes the IC50 as determined in cell culture (e.g., the concentration of an active agent, which achieves a half-maximal inhibition in (a) binding of VN to at least one VN-binding partner selected from an IGF and an IGFBP or (b) formation of a complex comprising VN and at least one VN-binding partner selected from an IGF and an IGFBP). Such information can be used to more accurately determine useful doses in mammals, including humans.

Dosage amount and interval may be adjusted individually to provide plasma levels of the active agent, which are sufficient to maintain VN peptide antagonist-inhibitory effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

The VN peptide antagonist may be administered concurrently with at least one ancillary therapy that treats or ameliorates the symptoms or reverses or inhibits the development or progression of the hyperproliferative disorder in the subject. The antagonist may be used therapeutically after the ancillary therapy or may be used before the therapy is administered or together with the therapy. Accordingly, the present invention contemplates combination therapies, which employ a VN peptide antagonist and concurrent administration of an ancillary therapy (e.g., medical treatment), non-limiting examples of which include radiotherapy, surgery, chemotherapy, hormone abalation therapy, pro-apoptosis therapy and immunotherapy.

5.1 Radiotherapy

Radiotherapies include radiation and waves that induce DNA damage for example, γ-irradiation, X-rays, UV irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half life of the isotope, the strength and type of radiation emitted, and the uptake by the neoplastic cells.

Non-limiting examples of radiotherapies include conformal external beam radiotherapy (50-100 Grey given as fractions over 4-8 weeks), either single shot or fractionated, high dose rate brachytherapy, permanent interstitial brachytherapy, systemic radio-isotopes (e.g., Strontium 89). In some embodiments the radiotherapy may be administered in combination with a radiosensitizing agent. Illustrative examples of radiosensitizing agents include but are not limited to efaproxiral, etanidazole, fluosol, misonidazole, nimorazole, temoporfin and tirapazamine.

5.2 Chemotherapy

Chemotherapeutic agents may be selected from any one or more of the following categories:

(i) antiproliferative/antineoplastic drugs and combinations thereof, as used in medical oncology, such as alkylating agents (e.g., cis-platin, carboplatin, cyclophosphamide, nitrogen mustard, melphalan, chlorambucil, busulphan and nitrosoureas); antimetabolites (e.g., antifolates such as fluoropyridines like 5-fluorouracil and tegafur, raltitrexed, methotrexate, cytosine arabinoside and hydroxyurea); antitumor antibiotics (e.g., anthracyclines like adriamycin, bleomycin, doxorubicin, daunomycin, epirubicin, idarubicin, mitomycin-C, dactinomycin and mithramycin); antimitotic agents (e.g., vinca alkaloids like vincristine, vinblastine, vindesine and vinorelbine and taxoids like paclitaxel and docetaxel; and topoisomerase inhibitors (e.g., epipodophyllotoxins like etoposide and teniposide, amsacrine, topotecan and camptothecin);

(ii) cytostatic agents such as antioestrogens (e.g., tamoxifen, toremifene, raloxifene, droloxifene and iodoxyfene), oestrogen receptor down regulators (for example fulvestrant), antiandrogens (e.g., bicalutamide, flutamide, nilutamide and cyproterone acetate), UH antagonists or LHRH agonists (e.g., goserelin, leuprorelin and buserelin), progestogens (e.g., megestrol acetate), aromatase inhibitors (e.g., as anastrozole, letrozole, vorazole and exemestane) and inhibitors of 5α-reductase such as finasteride;

(iii) agents which inhibit cancer cell invasion (e.g., metalloproteinase inhibitors like marimastat and inhibitors of urokinase plasminogen activator receptor function);

(iv) inhibitors of growth factor function, for example such inhibitors include growth factor antibodies, growth factor receptor antibodies (e.g., the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example other inhibitors of the epidermal growth factor family (for example other EGFR family tyrosine kinase inhibitors such as N-(3-chloro-4-fluorophenyl)-7-methoxy-6-(3-morpholinopropoxy)quinazolin-4-    -amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazoli-n-4-amine (CI 1033)), for example inhibitors of the platelet-derived growth factor family and for example inhibitors of the hepatocyte growth factor family;

(v) anti-angiogenic agents such as those which inhibit the effects of vascular endothelial growth factor, (e.g., the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (e.g., linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense; and (viii) gene therapy approaches, including for example approaches to replace aberrant genes such as aberrant p53 or aberrant GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

5.3 Immunotherapy

Immunotherapy approaches, include for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies. These approaches generally rely on the use of immune effector cells and molecules to target and destroy cancer cells. The immune effector may be, for example, an antibody specific for some marker on the surface of a malignant cell. The antibody alone may serve as an effector of therapy or it may recruit other cells to actually facilitate cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a malignant cell target. Various effector cells include cytotoxic T cells and NK cells.

5.4 Other Therapies

Examples of other cancer therapies include phototherapy, cryotherapy, toxin therapy or pro-apoptosis therapy. One of skill in the art would know that this list is not exhaustive of the types of treatment modalities available for cancer and other hyperplastic lesions.

It is well known that chemotherapy and radiation therapy target rapidly dividing cells and/or disrupt the cell cycle or cell division. These treatments are offered as part of the treating several forms of cancer, aiming either at slowing their progression or reversing the symptoms of disease by means of a curative treatment. However, these ancillary treatments may lead to an immunocompromised state and ensuing pathogenic infections and thus the present invention also extends to combination therapies, which employ the VN peptide antagonist, ancillary treatment(s) and an anti-infective agent that is effective against an infection that develops or that has an increased risk of developing from an immunocompromised condition resulting from the ancillary treatment. The anti-infective drug is suitably selected from antimicrobials, which include without limitation compounds that kill or inhibit the growth of microorganisms such as viruses, bacteria, yeast, fungi, protozoa, etc. and thus include antibiotics, amebicides, antifungals, antiprotozoals, antimalarials, antituberculotics and antivirals. Anti-infective drugs also include within their scope anthelmintics and nematocides. Illustrative antibiotics include quinolones (e.g., amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; and garenoxacin), tetracyclines, glycylcyclines and oxazolidinones (e.g., chlortetracycline, demeclocycline, doxycycline, lymecycline, methacycline, minocycline, oxytetracycline, tetracycline, tigecycline; linezolide, eperozolid), glycopeptides, aminoglycosides (e.g., amikacin, arbekacin, butirosin, dibekacin, fortimicins, gentamicin, kanamycin, meomycin, netilmicin, ribostamycin, sisomicin, spectinomycin, streptomycin, tobramycin), β-lactams (e.g., imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g., azithromycin, clarithromycin, erythromycin, oleandomycin, rokitamycin, rosaramicin, roxithromycin, troleandomycin), ketolides (e.g., telithromycin, cethromycin), coumermycins, lincosamides (e.g., clindamycin, lincomycin) and chloramphenicol.

Illustrative antivirals include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine.

Non-limiting examples of amebicides or antiprotozoals include atovaquone, chloroquine hydrochloride, chloroquine phosphate, metronidazole, metronidazole hydrochloride, and pentamidine isethionate. Anthelmintics can be at least one selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. Non-limiting examples of antimalarials include chloroquine hydrochloride, chloroquine phosphate, doxycycline, hydroxychloroquine sulfate, mefloquine hydrochloride, primaquine phosphate, pyrimethamine, and pyrimethamine with sulfadoxine. Antituberculotics include but are not restricted to clofazimine, cycloserine, dapsone, ethambutol hydrochloride, isoniazid, pyrazinamide, rifabutin, rifampin, rifapentine, and streptomycin sulfate.

As noted above, the present invention encompasses co-administration of an VN peptide antagonist in concert with an additional agent. It will be understood that, in embodiments comprising administration of the VN peptide antagonist with other agents, the dosages of the actives in the combination may on their own comprise an effective amount and the additional agent(s) may further augment the therapeutic or prophylactic benefit to the patient. Alternatively, the VN peptide antagonist and the additional agent(s) may together comprise an effective amount for preventing or treating the hematological malignancy. It will also be understood that effective amounts may be defined in the context of particular treatment regimens, including, e.g., timing and number of administrations, modes of administrations, formulations, etc. In some embodiments, the VN peptide antagonist and optionally the ancillary treatment are administered on a routine schedule. Alternatively, the ancillary treatment may be administered as symptoms arise. A "routine schedule" as used herein, refers to a predetermined designated period of time. The routine schedule may encompass periods of time which are identical or which differ in length, as long as the schedule is predetermined. For instance, the routine schedule may involve administration of the VN peptide antagonist on a daily basis, every two days, every three days, every four days, every five days, every six days, a weekly basis, a monthly basis or any set number of days or weeks there-between, every two months, three months, four months, five months, six months, seven months, eight months, nine months, ten months, eleven months, twelve months, etc. Alternatively, the predetermined routine schedule may involve concurrent administration of the VN peptide antagonist and the ancillary therapy on a daily basis for the first week, followed by a monthly basis for several months, and then every three months after that. Any particular combination would be covered by the routine schedule as long as it is determined ahead of time that the appropriate schedule involves administration on a certain day.

Generally, the ingredients of the compositions of the invention are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The VN peptides of the present invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Various delivery systems are known and can be used to administer one or more prophylactic or therapeutic agents of the present invention (e.g., one or more VN peptide antagonists or the combination of one or more VN peptide antagonists and an ancillary agent that is useful for preventing, managing, treating, or ameliorating a hyperproliferative cell disorder or one or more symptoms thereof), including for example, encapsulation in liposomes, microparticles, microcapsules, recombinant cells capable of expressing a VN peptide antagonist, receptor-mediated endocytosis (see, e.g., Wu and Wu, 1987. *J. Biol. Chem.* 262:4429-4432), construction of a nucleic acid as part of a retroviral or other vector, etc. Methods of administering a prophylactic or therapeutic agent of the present invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903. In one embodiment, a VN peptide antagonist of the invention, combination therapy, or a composition of the invention is administered using Alkermes AIR™ pulmonary drug delivery technology (Alkermes, Inc., Cambridge, Mass.). In specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In specific embodiments, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel™), or collagen matrices. In one embodiment, an effective amount of one or more antibodies of the invention antagonists is administered locally to the affected area to a subject to prevent, treat, manage, and/or ameliorate a disorder or a symptom thereof. In other embodiments, an effective amount of one or more VN peptide antagonists of the invention is administered locally to the affected area in combination with an effective amount of one or more therapies (e.g., an ancillary treatment as described for example above) to prevent, treat, manage, and/or ameliorate a hyperproliferative cell disorder or one or more symptoms thereof.

In other embodiments, the prophylactic or therapeutic agent can be delivered in a controlled release or sustained release system. In illustrative examples of this type, a pump is used to achieve controlled or sustained release (see, Langer, 1990. *Science* 249:1527-1533; Sefton, 1987. *CRC Crit. Ref. Biomed. Eng.* 14:20; Buchwald et al., 1980. *Surgery* 88:507; Saudek et al., 1989. *N. Engl. J. Med.* 321:574). In other illustrative examples, polymeric materials can be used to achieve controlled or sustained release of the therapies of the invention (see, e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983. *J., Macromol. Sci. Rev. Macromol. Chem.* 23:61; see, also Levy et al., 1985. *Science* 228:190; During et al., 1989. *Ann. Neurol.* 25:351; Howard et al., 1989. *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In some embodiments, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, supra). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698. Ning et al., 1996. *Radiotherapy & Oncology* 39:179-189, Song et al., 1995. *PDA Journal of Pharmaceutical Science & Technology* 50:372-397, Cleek et al., 1997. *Pro. Int'l. Symp. Control. Rel. Bioact. Mater.* 24:853-854, and Lam et al., 1997. *Proc. Int'l Symp. Control Rel. Bioact. Mater.* 24:759-760.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the methods of the invention comprise intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the methods of the invention comprise oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinized maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The methods of the invention comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR™ pulmonary drug delivery technology (Alkermes, Inc., Cambridge, Mass.).

The methods of the invention may comprise administration of compositions formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is/are packaged in a hermetically sealed container such as an ampoule or sachet indicating the quantity of the agent. In some embodiments, one or more of the prophylactic or therapeutic agents, or pharmaceutical compositions of the invention is/are supplied as a dry sterilized lyophilized powder or water free concentrate in a hermetically sealed container and can be reconstituted (e.g., with water or saline) to the appropriate concentration for administration to a subject. Suitably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is/are supplied in liquid form in a hermetically sealed container indicating the quantity and concentration of the agent. Suitably, the liquid form of the administered composition is supplied in a hermetically sealed container at least 0.25 mg/mL, more preferably at least 0.5 mg/mL, at least 1 mg/mL, at least 2.5 mg/mL, at least 5 mg/mL, at least 8 mg/mL, at least 10 mg/mL, at least 15 mg/kg, at least 25 mg/mL, at least 50 mg/mL, at least 75 mg/mL or at least 100 mg/mL. The liquid form should be stored at between 2° C. and 8° C. in its original container.

Generally, the ingredients of the compositions of the invention are derived from a subject that is the same species origin or species reactivity as recipient of such compositions. Thus, in specific embodiments, human VN peptide antagonists are administered to a human patient for therapy or prophylaxis.

The present invention provides methods for treating, preventing, and managing a hyperproliferative cell disorder through the administration to a subject in need thereof of an effective amount of a VN peptide antagonist, composition or combination therapy of the present invention. The subject is suitably a mammal such as a non-primate mammal or a primate mammal. In specific embodiments, the subject is a human. Exemplary hyperproliferative cell disorders encompass a variety of conditions wherein cell division is deregulated including neoplastic disorders, illustrative examples of which include neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells.

In specific embodiments, the hyperproliferative cell disorder is a cancer. Non-limiting cancers include: bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas; leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America)

In specific embodiments, the cancer that is treated, prevented or managed is of an epithelial origin. Non-limiting examples of such epithelial cancers include cancer of the lung, colon, prostate, ovary, breast, and skin. In particularly preferred embodiments, the epithelial cancer is a breast cancer.

In particular embodiments, the methods of the present invention can be used to treat and/or prevent metastasis from primary tumors.

In other embodiments, the invention provides methods of treating, preventing and managing non-neoplastic hyperproliferative cell disorders, including but not limited to, hyperproliferative epithelial cell disorders, illustrative examples of which include asthma, chromic obstructive pulmonary disorder (COPD), lung fibrosis, bronchial hyper responsiveness, psoriasis, seborrheic dermatitis and cystic fibrosis, etc.; and non-neoplastic hyperproliferative endothelial cell disorders illustrative examples of which include restenosis, hyperproliferative vascular disease, Behcet's Syndrome, atherosclerosis, macular degeneration as well as scarring disorder, non-limiting examples of which include scarring disorders such as post-operative scarring, hypertrophic scarring, keloid (e.g., keratinocyte) scarring and glial (e.g., astrocyte) scarring.

The methods, compositions and combination therapies as defined herein comprise the administration of one or more VN peptide antagonists of the invention to subjects/patients suffering from or expected to suffer from a hyperproliferative cell disorder, e.g., have a genetic predisposition for a particular hyperproliferative cell disorder, have been exposed to an agent (e.g., carcinogen) that stimulates the development of a particular hyperproliferative cell disorder (e.g., cancer), or are in remission from a particular hyperproliferative cell disorder (e.g., cancer). Such patients may or may not have been previously treated for the hyperproliferative cell disorder (e.g., cancer). The methods and compositions of the invention may be used as a first line or second line treatment of the hyperproliferative cell disorder (e.g., cancer). Included in the invention is also the treatment of patients undergoing other therapies for a hyperproliferative cell disorder and the methods and compositions of the invention can be used before any adverse effects or intolerance of these other therapies occurs. The invention also encompasses methods for administering one or more VN peptide antagonists of the invention to treat or ameliorate symptoms in refractory patients. In certain embodiments in which a hyperproliferative cell disorder (e.g., cancer) is "refractory" to a therapy, this means that at least some significant portion of the hyperproliferative cells (e.g., cancer cells) are not killed or their cell division arrested. The determination of whether the hyperproliferative cells are refractory can be made either in vivo or in vitro by any method known in the art for assaying the effectiveness of treatment on cancer cells, using the art-accepted meanings of "refractory" in such a context. In various embodiments, a hyperproliferative cell disorder is refractory where the number of hyperproliferative cells has not been significantly reduced, or has increased. The invention also encompasses methods for administering one or more VN peptide antagonists to prevent the onset or recurrence of a hyperproliferative cell disorder in patients predisposed to having the hyperproliferative cell disorder.

In alternate embodiments, the invention provides methods for treating patients' hyperproliferative cell disorder (e.g., cancer) by administering one or more VN peptide antagonists of the invention in combination with any other treatment or to patients who have proven refractory to other treatments but are no longer on these treatments. In certain embodiments in which the hyperproliferative cell disorder is cancer, the patients being treated by the methods of the invention are patients already being treated with chemotherapy, radiation therapy, hormonal therapy, or biological therapy/immunotherapy. Among these patients are refractory patients and those with cancer despite treatment with existing cancer therapies. In other embodiments, the patients have been treated and have no disease activity and one or more VN peptide antagonists of the invention are administered to prevent the recurrence of cancer.

In other embodiments in which the hyperproliferative cell disorder is cancer, patients with a pre-malignant cancer are administered VN peptide antagonists of the invention to treat the disorder and decrease the likelihood that it will progress to malignant cancer. In illustrative examples of this type, the pre-malignant cancer is high-grade prostatic intraepithelial neoplasia (PIN), ductal carcinoma of the breast in, or compound nevi.

In order that the invention may be readily understood and put into practical effect, particular preferred embodiments will now be described by way of the following non-limiting examples.

EXAMPLES

Example 1

VN-Peptide Array Detection of Novel and Unique Peptides Involved in Binding of IGF-II, IGFBP-3 and IGFBP-5 to VN

Members of the IGF family have been shown to play critical roles in normal growth and development, as well as in tumour biology. The IGF system is complex and the biological effects of the IGFs are determined by their diverse interactions between many molecules, including their interactions with ECM proteins. Studies have demonstrated that IGFs associate with the ECM protein vitronectin (VN) through IGF-binding proteins (IGFBP) and that this interaction modulates IGF-stimulated biological functions, namely cell migration and cell survival through the cooperative involvement of the IGF-1R and VN-binding integrins. To date, it has been demonstrated that IGF-I binds to ECM protein VN via IGFBP-2, -3, -4 and -5 to form a trimeric complex, whereas IGF-II binds directly to VN forming a dimeric complex (Kricker et al., 2003; Upton et al., 1999). The trimeric complex has been shown to mediate in vitro cell migration, invasion, proliferation and 3D cell survival of transformed as well as non-transformed breast cells (Hollier et al., 2008; Kashyap et al., 2011). In addition, the dimeric complex (IGF-II:VN) has been shown to stimulate breast cell proliferation and migration (Noble et al., 2003). The study described herein aimed to describe the effects of IGF:VN interactions on breast cell function in order to dissect the molecular mechanisms underlying IGF:VN-induced responses with the ultimate goal being to design inhibitors to block the effects of such interactions.

The present studies focus on investigating novel strategies to prevent the association of the IGF-I:IGFBP:VN trimeric complexes by essentially targeting the interactions between IGFBP and VN. This is the first study to report the putative binding sites for IGF-II, IGFBP-3 and IGFBP-5 within VN, with a common binding site reported to be located at the C-terminal end within the HX-2 domain of VN. Moreover, this study also demonstrated that the peptides designed to this site were shown to significantly inhibit the trimeric complex-induced breast cancer cell migration.

The approach taken by the inventors was to target ligand accessibility to the tumorigenic receptors of the IGF system and VN receptors (i.e., integrins) in order to develop novel small molecule antagonists of the IGF system in hyperproliferative cell disorders including cancers such as breast cancer. The particular advantage of identifying inhibitors using this approach is the potential to block the activation of all the tumorigenic receptors within the IGF system, namely, IGF-1R, IR-A and Hybrid-Receptors, and at the same time allow for the normal insulin signalling to occur through the IR-B receptor. This can be achieved if the inhibition is mediated at the ligand level; i.e., with therapies directed at targeting the accessibility of ligands, IGF-I and IGF-II, to the receptors. This approach offers the advantage of potentially blocking only the tumorigenic receptors, without the metabolic liability of blocking insulin and/or the IR-B receptor.

The inventors designed small-molecule VN-peptides that could potentially disrupt the formation of the IGF-I:IGFBP:VN trimeric or the IGF-II:VN dimeric complexes by binding to the IGFBPs and/or IGF-II and preventing their association with VN within the complex. To design peptides, the binding sites of IGFBP-3/-5 and IGF-II on VN were first determined using VN-peptide arrays. The entire VN protein sequence, excluding the signal peptide (residues 1-19), was divided into overlapping 16-mer peptides with 3AA frameshift/offset (for peptide sequences refer to Table 6) and immobilized onto cellulose membranes (peptide spotting was outsourced to PepMetric Technologies Inc). For a schematic of the arrangement of VN peptides and controls refer to FIG. 2. The resultant peptide arrays were incubated either with IGFBP-3, IGFBP-5 or IGF-II ligands, probed with the respective antibodies, the membranes developed using ECL, and imaged using the ChemiDoc™ XRS system (BioRad). The spots on the membrane were analysed using TotalLab array quantification software (TotalLab Ltd, Newcastle, England) identifying positive peptide spots by comparing each spot to the combined intensities of the negative controls.

TABLE 6

AMINO ACID SEQUENCE OF VN-PEPTIDES SPOTTED ONTO PEPTIDE ARRAY

| Grid No. | Peptide Sequence |
| --- | --- |
| 1 | DQESCKGRCTEGFNVD |
| 2 | SCKGRCTEGFNVDKKC |
| 3 | GRCTEGFNVDKKCQCD |
| 4 | TEGFNVDKKCQCDELC |
| 5 | FNVDKKCQCDELCSYY |
| 6 | DKKCQCDELCSYYQSC |
| 7 | CQCDELCSYYQSCCTD |
| 8 | DELCSYYQSCCTDYTA |
| 9 | CSYYQSCCTDYTAECK |
| 10 | YQSCCTDYTAECKPQV |
| 11 | CCTDYTAECKPQVTRG |
| 12 | DYTAECKPQVTRGDVF |
| 13 | AECKPQVTRGDVFTMP |
| 14 | KPQVTRGDVFTMPEDE |
| 15 | VTRGDVFTMPEDEYTV |
| 16 | GDVFTMPEDEYTVYDD |
| 17 | FTMPEDEYTVYDDGEE |
| 18 | PEDEYTVYDDGEEKNN |
| 19 | EYTVYDDGEEKNNATV |
| 20 | VYDDGEEKNNATVHEQ |
| 21 | DGEEKNNATVHEQVGG |
| 22 | EKNNATVHEQVGGPSL |
| 23 | NATVHEQVGGPSLTSD |
| 24 | VHEQVGGPSLTSDLQA |
| 25 | QVGGPSLTSDLQAQSK |
| 26 | GPSLTSDLQAQSKGNP |
| 27 | LTSDLQAQSKGNPEQT |

TABLE 6-continued

AMINO ACID SEQUENCE OF VN-PEPTIDES SPOTTED ONTO PEPTIDE ARRAY

| Grid No. | Peptide Sequence |
|---|---|
| 28 | DLQAQSKGNPEQTPVL |
| 29 | AQSKGNPEQTPVLKPE |
| 30 | KGNPEQTPVLKPEEEA |
| 31 | PEQTPVLKPEEEAPAP |
| 32 | TPVLKPEEEAPAPEVG |
| 33 | LKPEEEAPAPEVGASK |
| 34 | EEEAPAPEVGASKPEG |
| 35 | APAPEVGASKPEGIDS |
| 36 | PEVGASKPEGIDSRPE |
| 37 | GASKPEGIDSRPETLH |
| 38 | KPEGIDSRPETLHPGR |
| 39 | GIDSRPETLHPGRPQP |
| 40 | SRPETLHPGRPQPPAE |
| 41 | ETLHPGRPQPPAEEEL |
| 42 | HPGRPQPPAEEELCSG |
| 43 | RPQPPAEEELCSGKPF |
| 44 | PPAEEELCSGKPFDAF |
| 45 | EEELCSGKPFDAFTDL |
| 46 | LCSGKPFDAFTDLKNG |
| 47 | GKPFDAFTDLKNGSLF |
| 48 | FDAFTDLKNGSLFAFR |
| 49 | FTDLKNGSLFAFRGQY |
| 50 | LKNGSLFAFRGQYCYE |
| 51 | GSLFAFRGQYCYELDE |
| 52 | FAFRGQYCYELDEKAV |
| 53 | RGQYCYELDEKAVRPG |
| 54 | YCYELDEKAVRPGYPK |
| 55 | ELDEKAVRPGYPKLIR |
| 56 | EKAVRPGYPKLIRDVW |
| 57 | VRPGYPKLIRDVWGIE |
| 58 | GYPKLIRDVWGIEGPI |
| 59 | KLIRDVWGIEGPIDAA |
| 60 | RDVWGIEGPIDAAFTR |
| 61 | WGIEGPIDAAFTRINC |
| 62 | EGPIDAAFTRINCQGK |
| 63 | IDAAFTRINCQGKTYL |
| 64 | AFTRINCQGKTYLFKG |
| 65 | RINCQGKTYLFKGSQY |
| 66 | CQGKTYLFKGSQYWRF |
| 67 | KTYLFKGSQYWRFEDG |
| 68 | LFKGSQYWRFEDGVLD |
| 69 | GSQYWRFEDGVLDPDY |
| 70 | YWRFEDGVLDPDYPRN |
| 71 | FEDGVLDPDYPRNISD |
| 72 | GVLDPDYPRNISDGFD |
| 73 | DPDYPRNISDGFDGIP |
| 74 | YPRNISDGFDGIPDNV |
| 75 | NISDGFDGIPDNVDAA |
| 76 | DGFDGIPDNVDAALAL |
| 77 | DGIPDNVDAALALPAH |
| 78 | PDNVDAALALPAHSYS |
| 79 | VDAALALPAHSYSGRE |
| 80 | ALALPAHSYSGRERVY |
| 81 | LPAHSYSGRERVYFFK |
| 82 | HSYSGRERVYFFKGKQ |
| 83 | SGRERVYFFKGKQYWE |
| 84 | ERVYFFKGKQYWEYQF |
| 85 | YFFKGKQYWEYQFHQ |
| 86 | KGKQYWEYQFHQPSQ |
| 87 | QYWEYQFHQPSQEEC |
| 88 | EYQFHQPSQEECEGS |
| 89 | FQHQPSQEECEGSSLS |
| 90 | QPSQEECEGSSLSAVF |
| 91 | QEECEGSSLSAVFEHF |
| 92 | CEGSSLSAVFEHFAMM |
| 93 | SSLSAVFEHFAMMQRD |
| 94 | SAVFEHFAMMQRDSWE |
| 95 | FEHFAMMQRDSWEDIF |
| 96 | FAMMQRDSWEDIFELL |
| 97 | MQRDSWEDIFELLFWG |
| 98 | DSWEDIFELLFWGRTS |
| 99 | EDIFELLFWGRTSAGT |
| 100 | FELLFWGRTSAGTRQP |
| 101 | LFWGRTSAGTRQPQFI |
| 102 | GRTSAGTRQPQFISRD |

TABLE 6-continued

AMINO ACID SEQUENCE OF VN-PEPTIDES SPOTTED ONTO PEPTIDE ARRAY

| Grid No. | Peptide Sequence |
|---|---|
| 103 | SAGTRQPQFISRDWHG |
| 104 | TRQPQFISRDWHGVPG |
| 105 | PQFISRDWHGVPGQVD |
| 106 | ISRDWHGVPGQVDAAM |
| 107 | DWHGVPGQVDAAMAGR |
| 108 | GVPGQVDAAMAGRIYI |
| 109 | GQVDAAMAGRIYISGM |
| 110 | DAAMAGRIYISGMAPR |
| 111 | MAGRIYISGMAPRPSL |
| 112 | RIYISGMAPRPSLAKK |
| 113 | ISGMAPRPSLAKKQRF |
| 114 | MAPRPSLAKKQRFRHR |
| 115 | RPSLAKKQRFRHRNRK |
| 116 | LAKKQRFRHRNRKGYR |
| 117 | KQRFRHRNRKGYRSQR |
| 118 | FRHRNRKGYRSQRGHS |
| 119 | RNRKGYRSQRGHSRGR |
| 120 | KGYRSQRGHSRGRNQN |
| 121 | RSQRGHSRGRNQNSRR |
| 122 | RGHSRGRNQNSRRPSR |
| 123 | SRGRNQNSRRPSRATW |
| 124 | RNQNSRRPSRATWLSL |
| 125 | NSRRPSRATWLSLFSS |
| 126 | RPSRATWLSLFSSEES |
| 127 | RATWLSLFSSEESNLG |
| 128 | WLSLFSSEESNLGANN |
| 129 | LFSSEESNLGANNYDD |
| 130 | SEESNLGANNYDDYRM |
| 131 | SNLGANNYDDYRMDWL |
| 132 | GANNYDDYRMDWLVPA |
| 133 | NYDDYRMDWLVPATCE |
| 134 | DYRMDWLVPATCEPIQ |
| 135 | MDWLVPATCEPIQSVF |
| 136 | LVPATCEPIQSVFFFS |
| 137 | ATCEPIQSVFFFSGDK |
| 138 | EPIQSVFFFSGDKYYR |
| 139 | QSVFFFSGDKYYRVNL |
| 140 | FFFSGDKYYRVNLRTR |
| 141 | SGDKYYRVNLRTRRVD |
| 142 | KYYRVNLRTRRVDTVD |
| 143 | RVNLRTRRVDTVDPPY |
| 144 | LRTRRVDTVDPPYPRS |
| 145 | RRVDTVDPPYPRSIAQ |
| 146 | DTVDPPYPRSIAQYWL |
| 147 | DPPYPRSIAQYWLGCP |
| 148 | YPRSIAQYWLGCPAPG |

Figure 2:
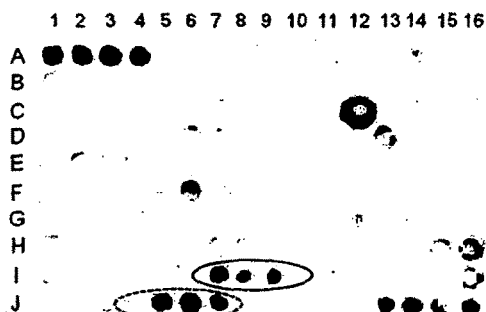
FIG. 2 is a diagrammatic representation showing arrangement of VN-peptides and controls on a peptide array.
Figure 3:
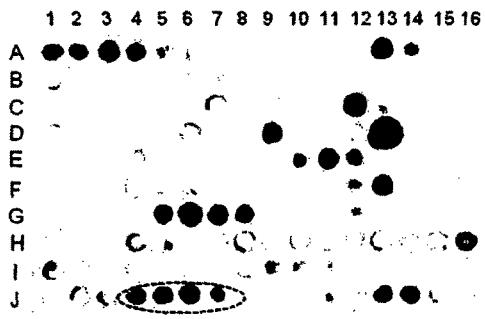
FIG. 3 is a photographic representation of VN peptide arrays identifying sites on VN involved in the binding of IGF-II, IGFBP-3 and IGFBP-5. VN peptide arrays were prepared (PepMetric Technologies Inc.) by spotting the entire VN sequence divided into overlapping 16-mer peptides with 3 amino acid frameshifts in a 10×16 grid onto cellulose sheets. These membranes were incubated overnight with IGF-II, IGFBP-3 or IGFBP-5 ligands, which are known to bind VN. Membranes were then probed with their corresponding antibodies (anti-IGF-II, anti-IGFBP-3 and anti-IGFBP-5, respectively). All membranes were probed with their respective secondary antibodies and developed using enhanced chemiluminescence. Positive spots are indicated by dark colored opaque circles. The peptide arrays were spotted with positive and negative controls (A1-4 and J13-16=positives; A5-6, J11-12=negatives). Circled spots indicate the regions towards which the VN-peptides were designed for further peptide-based inhibition studies. Hashed lined circles indicate peptide spots which came up positive for all the proteins tested and solid lined circles indicate peptides spots that were specific for IGF-II binding to VN.
Figure 3:
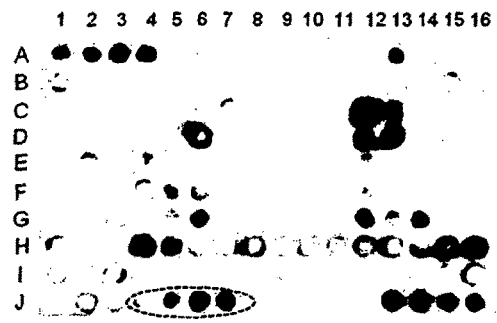

The universal binding peptides tested by the manufacturer to be positive for antibodies from goat, mouse, rabbit and chicken (positive controls) were confirmed to react with all the arrays tested; grid numbers A1-4 and J13-16 (FIG. 3). Furthermore, non-binding peptides and BSA (negative controls; grid numbers A5-6 and J11-12) did not hybridize with the arrays tested. TotalLab software was used to identify the positive hybridizing targets (positive hits). Each VN-peptide that came up with a stronger spot intensity than the negative controls was deemed a positive hit. Several positive VN-peptides were detected. Unique spots were evident for each ligand in addition to candidate VN-peptides that bound all the three IGF-II, IGFBP-3 and IGFBP-5 ligands, in common. For IGF-II, positive hybridizations were detected at five different positions: A14; F5 and 6; G12; 17, 8 and 9; and J4, 5, 6 and 7 (FIG. 2). For IGFBP-3, spots were detected at seven different positions: A13 and 14; C12 and 13; F6; F12 and 13; G5, 6, 7 and 8; G12 and 14; and J4, 5, 6 and 7 (FIG. 2). For IGFBP-5, spots were detected at five different positions: A13; C12 and 13; F5 and 6; G12, 13 and 14; and J4, 5, 6 and 7 (FIG. 3). The spots common to all the three ligands were A13 and 14; and J4, 5, 6 and 7 (FIG. 3). The procedures used to spot peptides in row H may not have been the most optimal, given a ring of non-specific binding was observed around each spot (H4-16) in all four peptide arrays tested. In most cases, instead of a single peptide spot, a string of spots (2 up to 4 consecutive spots) were detected as positive, potentially constituting overlapping ligand-binding motif (6 up to 12 amino acids long) within VN.

From these peptide arrays the inventors were able to confirm that the three ligands tested, IGF-II, IGFBP-3, and IGFBP-5 interact with VN at sites that were both shared and unique to the ligands. This is the first instance where such interacting sites within VN have been identified for IGFBPs and IGF-II.

Example 2

Novel Binding Sites of IGF-II, IGFBP-3, IGFBP-5 to VN

The peptide array experiments outlined above identified peptide sequences both uniquely and commonly supporting the binding of IGF-II, IGFBP-3 and/or IGFBP-5 to VN. By performing ECL on the peptide arrays, ligands that bound to the VN-peptides could be identified as dark opaque circular spots (FIG. 3). However, the peptide sequence and the location of these peptides within the VN-sequence were not identified. Therefore the next step was to identify the sequence of these peptides and to spatially align these binding motifs within the VN sequence. The sequence of each ligand-binding peptide was identified by cross-referencing the grid location of the peptide spot with the amino acid sequence of the peptide corresponding to that grid number, as reported by the manufacturer. Once the sequences of the ligand-binding peptides were identified, they were subjected to bioinformatics analysis to identify which region within the native VN polypeptide they each ligand tested, but more importantly, in identifying sites within VN that were common to all the three ligands. It was seen that several binding sites (circled motifs 1, 3, 4 and 8) were shared by all the three IGF-II, IGFBP-3 and IGFBP-5 ligands (designated: ALL). Motif 1 was identified to be in the acidic SMB domain. Motifs 3 and 8 were localized within the HX-1 and HX-2 domains, respectively. Site 6 was detected to be within the region before the HBD domain of HX-2.

The sequence and ligand-binding parameters are also outlined in Table 7.

TABLE 7

SUMMARY OF IGF-II, IGFBP-3 AND IGFBP-5 BINDING TO VN ON VN-PEPTIDE ARRAY.

| Pep# | Grid# | Residue# | Region | Sequence | Charge | Hydro | Intensity (against -ve control) |
|---|---|---|---|---|---|---|---|
| 1A | A13 | 20 | SMB | CQCDELCSYYQSCCTD | -3.2 | -0.1 | 10-BP3, 11-BP5 |
| 1B | A14 | 23 | | DELCSYYQSCCTDYTA | -3.1 | -0.2 | 12-IGFII |
| 2A | C12 | 113 | CON | KPEGIDSRPETLHPGR | +0.1 | +0.9 | 4-BP3, 5-BP5 |
| 2B | C13 | 116 | | GIDSRPETLHPGRPQP | +0.1 | +0.5 | 2-BP3, 7-BP5 |
| 3A | F5 | 236 | HX-1 | VDAALALPAHSYSGRE | -0.9 | 0 | 1-BP3, 3-BP5, 5-IGFII |
| 3B | F6 | 239 | | ALALPAHSYSGRERVY | +1.1 | -0.1 | 1-BP3, 3-BP5, 10-IGFII |
| 4A | F12 | 257 | HX-1 | KGKQYWEYQFQHQPSQ | +1.1 | 0 | 6-BP3 |
| 4B | F13 | 260 | | QYWEYQFQHQPSQEEC | -3 | 0.1 | 12-BP3 |
| 5A | G5 | 284 | HX-2 | FEHFAMMQRDSWEDIF | -2.9 | -0.1 | 1.5-BP3 |
| 5B | G6 | 287 | | FAMMQRDSWEDIFELL | -3 | -0.1 | 4.5-BP3 |
| 5C | G7 | 290 | | MQRDSWEDIFELLFWG | -3 | -0.2 | 4.5-BP3 |
| 5D | G8 | 293 | | DSWEDIFELLFWGRTS | -3 | -0.1 | 2.5-BP3 |
| 6A | G12 | 305 | HX-2 | GRTSAGTRQPQFISRD | +2 | +0.5 | 2-BP3, 7-BP5, 12-IGFII |
| 6B | G13 | 308 | | SAGTRQPQFISRDWHG | +1.1 | +0.1 | 1-BP3, 1.5-BP5, 0-IGFII |
| 6C | G14 | 311 | | TRQPQFISRDWHGVPG | +1.1 | 0 | 1.5-BP3, 5-BP5, 1.5-IGFII |
| 7A* | I7 | 386 | HBD/ | LFSSEESNLGANNYDD | -4 | +0.3 | 17-IGF-II |
| 7B* | I8 | 389 | HX-2 | SEESNLGANNYDDYRM | -3 | +0.5 | 18-IGF-II |
| 7C* | I9 | 392 | | SNLGANNYDDYRMDWL | -2 | 0 | 12-IGF-II |
| 8A# | J4 | 422 | HX-2 | KYYRVNLRTRRVDTVD | +3 | +0.6 | 5-BP3, 3-BP5, 5-IGFII |
| 8B# | J5 | 425 | | RVNLRTRRVDTVDPPY | +2 | +0.5 | 7-BP3, 7-BP5, 17-IGFII |
| 8C# | J6 | 428 | | LRTRRVDTVDPPYPRS | +2 | +0.6 | 10-BP3, 9-BP5, 13-IGFII |
| 8D# | J7 | 431 | | RRVDTVDPPYPRSIAQ | +1 | +0.5 | 4-BP3, 8-BP5, 11-IGFII | belonged. Each peptide sequence was aligned with the entire VN-sequence using BLASTP (NIH) and their location within VN, identified. This in turn provided an indication of the regions/motifs within VN that were involved in the interactions with IGF-II, IGFBP-3 and IGFBP-5.

Figure 4:
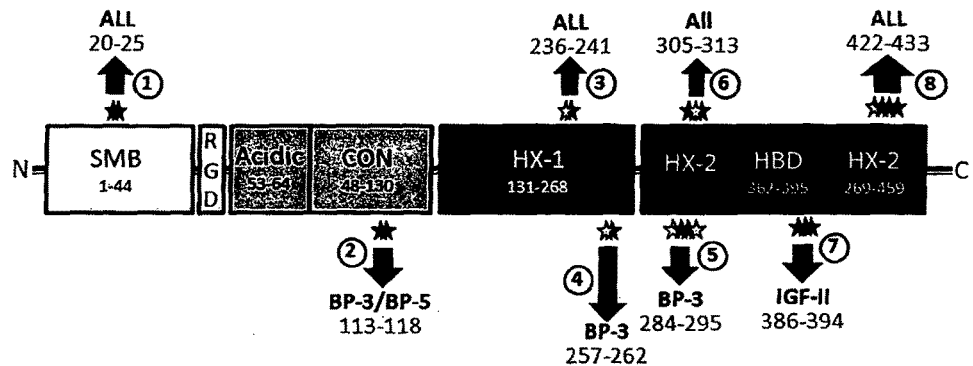
FIG. 4 is a schematic representation for the binding of IGF-II, IGFBP-3 and IGFBP-5 to VN. Graphical representation of VN is indicated in this figure with boxes specifying the VN domains. Stars indicate ligand binding position within the VN sequence. Number of stars indicates number of spots on peptide array detected as positive with shades indicating intensity of the spots. Breadths of arrows indicate the relative collective spot intensities. Ligands for which positive spots were detected and the ligand binding position of the positive spots are indicated below the respective arrowheads. The arrows marked 7 and 8 indicate regions from where peptides were designed for further experiments. ALL=positive for IGFBP-3, IGFBP-5 and IGF-II; BP=IGFBP; SMB=somatomedin B domain; RGD=Arginine-Glycine-Aspartic acid motif; CON=connecting linker domain; HX=Hemopexin-like domain; HBD=Heparin Binding Domain within HX.

Several IGF-II/IGFBP-3/IGFBP-5 binding motifs (indicated by a circled number) were identified and are graphically represented in FIG. 4. Several binding sites unique to each ligand were detected in the VN sequence (motifs 2, 4, 5 and 7). Motifs 4 and 5, localized within the HX-1 and HX-2 domains of VN, respectively, were detected to uniquely bind IGFBP-3. Motif 2, within the connecting-linker domain of VN, binds both IGFBP-3 and IGFBP-5. In addition, a unique binding site for IGF-II was detected within the HBD region of VN (motif 7). The inventors were interested in identifying sites that were not only unique for Legend for Table 7: * correspond to the solid line circles in FIG. 3; # correspond to the hashed lined circles in FIG. 3. Abbreviations used in this table are as follows: BP=IGFBP; SMB=somatomedin B domain; RGD=Arginine-Glycine-Aspartic acid motif; CON=connecting-linker domain; HX=Hemopexin-like domain and HBD=Heparin Binding Domain.

Table 7 summarizes the binding of IGF-II, IGFBP-3 and IGFBP-5 to VN and identifies the positions and the regions within VN sequence in which the peptides were detected as positive. The peptide numbers corresponding to the circled numbers in FIG. 4 and its corresponding location on the peptide array (Grid #), as per FIG. 3, is also included in Table 7. This table further summarizes the charge and the hydrophobicity associated with each peptide. In addition to these parameters, this table includes the relative intensity of each spot (last column; calculated using TotalLab software as fold-change in spot intensity compared to the average intensity of its corresponding negative controls) and were used for comparative analysis purposes. By comparing spot intensities outlined in Table 7 for all the ligand binding regions within VN and from a visual inspection of the spots on the peptide array (FIG. 3), it can be seen that the most prominent and consistent binding was seen for motifs 1 (A13-14) and 8 (J4-7). Furthermore, it was seen that in addition to binding motif 8, IGF-II also bound with high affinity to region 7. These intensity values for IGF-II binding to motif 7 of VN ranged from 17, 18 and 12 for spots 17, 18 and 19, respectively (Table 7).

These data reveal for the first time, not only the potential binding sites on VN for IGF-II, IGFBP-3 and IGFBP-5, but also identify key sites that could be targeted to disrupt the binding of such proteins to VN, thereby altering the functional consequences of the interactions between VN and IGFBP-3/-5, or VN and IGF-II.

Example 3

VN-Peptides Block IGF-I:IGFBP:VN Trimeric Complex-Induced Breast Cancer Cell Migration Two motifs (motifs 1 and 8) within native VN, deemed potentially significant in supporting the binding of IGF-II, IGFBP-3 and IGFBP-5, were identified as outlined in the previous section. After preliminary in silico analyses motif 8 (J4-7) was deemed as potentially the most significant region within native VN supporting binding interactions of all the three IGF-II, IGFBP-3 and IGFBP-5 proteins and was chosen for the initial analyses. The VN-peptide covering the sequences of motif 8 was designed such that it covered all the 3AA frameshift sets that contributed to a positive spot within the motif 8 (see, FIG. 3 and Table 7). The sequence of this peptide is RVNLRTRRVDTVDPPYPRS [SEQ ID NO:100] and is designated P8. Apart from the motif with the potential to bind all the three IGF-related proteins, the present inventors were also interested in designing peptides that could uniquely inhibit IGF-II from binding to VN, and thereby prevent the formation of the dimeric IGF-II:VN complex. Hence, another peptide was designed to mimic motif 7, which was shown to uniquely bind IGF-II (FIG. 2 and Table 7). The sequence of that peptide is LFSSEESNLGANNYDDYRMDWL [SEQ ID NO:86] and is designated P7. A negative control peptide was also designed spanning a region within VN that did not show any binding to the ligands tested (KTYLFKGSQYWRFEDG [SEQ ID NO:113]; Neg). The functional effects of these peptides on IGF-I:IGFBP:VN-stimulated breast cancer cell migration were investigated using Transwell® assays. Transwells® were pre-bound with VN, either alone or in combination with IGF-I and IGFBP-5 (TRI). Treatment with TRI supplemented with increasing concentrations of peptides P7 and/or P8 were assayed. TRI supplemented with Anlg or Neg peptide were included as positive and negative controls of migration inhibition, respectively. All unbound proteins were removed with washing and MCF-7 cell migration was assessed over 15 hours.

Figure 5:
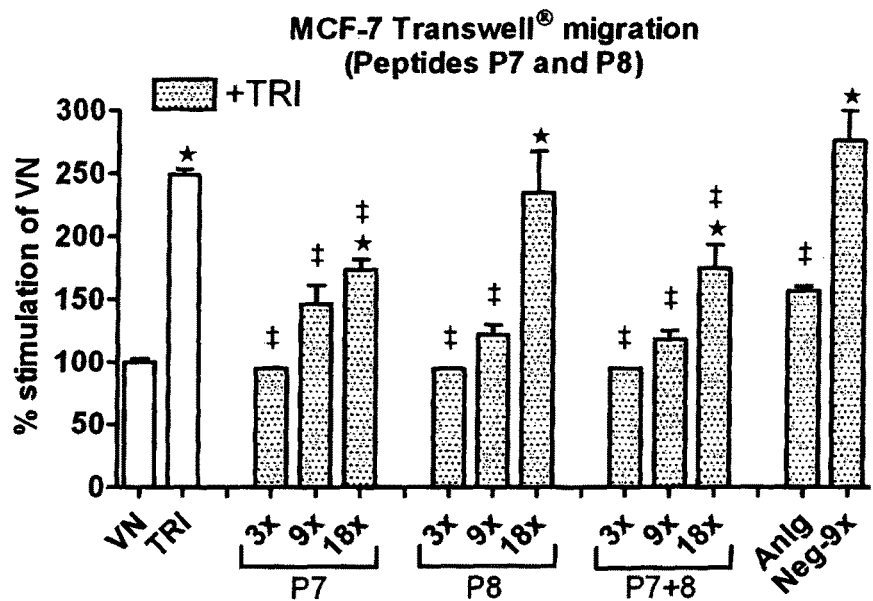
FIG. 5 is a graphical representation showing the effects of target VN-peptides on IGF-I+IGFBP-5+VN trimeric complex-stimulated MCF-7 cell migration. MCF-7 cells were seeded into Transwells® pre-coated with VN or IGF-I+IGFBP-5+VN trimeric complex (TRI) either alone or supplemented with increasing concentrations of either peptide P7, peptide P8 or a combination of peptides P7 and P8 (3× to 18× molar concentration of IGFBP-5). Trimeric complex supplemented with an inhibitor of trimeric complex-stimulated breast cancer migration (Anlg) and non-binding peptide (Neg) formed the positive and negative control treatments, respectively, for inhibition of migration. Cells were allowed to migrate for 15 hours and levels of migration assessed using crystal violet staining. The number of cells migrating through the Transwell® membrane in response to each treatment was then expressed as a percentage of those that migrated in response to VN only controls. Data are pooled from two independent experiments with treatments tested in triplicate wells in each replicate experiment. The asterisks indicate treatments which significantly increased migration above VN only (control) treatment ($p<0.05$). Supplementing the peptides (P7, P8 or P7+8) into the trimeric complex treatments reduced TRI-stimulated MCF-7 cell migration (‡($p<0.05$)). Error bars indicate SEM. TRI=IGF-I+IGFBP-5+VN trimeric complex; P7=IGF-II only binding-peptide (amino acid sequence: LFSSEESNLGANNYDDYRMDWL [SEQ ID NO:86]); P8=IGF-II and IGFBP-3/-5 binding-peptide (amino acid sequence: RVNLRTRRVDTVDPPYPRS [SEQ ID NO:100]); Neg=non-binding negative control VN-peptide (amino acid sequence: KTYLFKGSQYWRFEDG [SEQ ID NO:113]).

A significant increase (*, P<0.05) in the migration of MCF-7 cells was seen in response to TRI (249.1±4.6% of VN) compared to VN controls (FIG. 5). However, when peptides P7 and P8 were substituted within the complex, TRI-stimulated migration was significantly reduced (‡, p<0.05) at peptide molar concentrations of 3× and 9×. TRI-stimulated MCF-7 cell migration was significantly inhibited (‡, p<0.05) by a peptide molar concentration of 3×. Migration was reduced from 249.1±4.6% in response to the TRI treatment, to 94.7±0.2% in response to P7, 94.4±1% in response to peptide P8, and 94.5±1% when both P7 and P8 were supplemented into the TRI complex (FIG. 5). Similar trends were noted in the inhibition of TRI-stimulated migration at peptide concentrations of 9×, being reduced to 146±14% for P7, 121.7±8% for P8, and 118±7% for P7+P8. However, in the presence of peptide concentrations of 18×, a significant increase (*, p<0.05) in cell migration was recorded compared to VN controls (FIG. 4). This result suggests that the peptides at such a high concentration have no inhibitory effects on TRI-stimulated migration.

The non-binding peptide (Neg) did not affect TRI-stimulated migration but rather supported cell migration (276±24% of VN) similar to that induced by the TRI complex (FIG. 4). As previously noted, when Anlg (3×) was substituted into the TRI complex (TRI+Anlg) a significant decrease (‡, p<0.05) in cell migration was observed compared to the native TRI complex. Interestingly, the reduction in migration mediated by the peptides (~94% of VN), especially at concentrations of 3×, were even greater (p<0.01) than that mediated by the Anlg (p<0.05). This highlights the effectiveness of the specific inhibition mediated by these peptides.

Taken together, these data demonstrate that the peptides used in this study, mimicking key sites within the VN sequence that bind IGFBP-5, prevent the increased migration stimulated by the IGF-I+IGFBP-5+VN complex. Indeed, by preventing the association of IGFBP:VN, these peptides prevent the formation of the IGF-I:IGFBP-5:VN complex, thereby inhibiting its downstream effects.

Of note, the arrays show that IGF-II binds to P7 but does not bind IGFBP-3,-5. On the basis of the array results, the inventors had no expectation that P7 would disrupt the VN:BP-3,-5:IGF-I complex and thus show an inhibitory effect on MCF7 cell migration (FIG. 5). The primary objective of the migration experiments was to select peptides based on spots that were positive for IGF-II and BP-3,-5 signal, such as P1 and P8. That way both VN:IGF-II and VN:BP:IGF-I forms of the complex would be antagonized. At the onset of the experiments, P7 was only considered as a possible disruptor of the VN:IGF-II complex. Experimentally, the inventors wanted to see whether adding P7 and P8 peptides together would have any synergistic effects and used P7 alone as a control. Although not evident from the array experiment, the migration assay suggests that P7 may be binding IGFBP-5 and disrupting the VN:IGFBP association.

Conclusions

The use of whole-proteins for downstream therapeutic applications has certain demerits. These include: (1) poor oral bioavailability, (2) inadequate stability and shelf life, (3) immunogenicity, (4) short plasma half-life, and (5) poor penetration across biological membranes. However, bioactive peptides of fewer than 50 amino acids designed to interact with specific proteins within specific tissue microenvironments represent a rich class of candidate molecules that are good candidates for the treatment of cancer. Among the biological compounds tested pre-clinically and clinically, peptides are advantageous because they are small, less immunogenic, and can be modified to avoid degradation and improve bioavailability. Furthermore, with the advent of combinatorial peptide libraries, peptide arrays, peptide aptamer and phage-display methods to screen for a large number of peptides that bind specific proteins, the use of peptides as therapeutic inhibitors has gained immense popularity.

Experimental work described herein defined peptides that could bind IGFBP-3, IGFBP-5 or IGF-II at sites critical to VN binding. These peptides have particular function in inhibiting or disrupting the IGF-I:IGFBP:VN or IGF-II:VN complex, thereby inhibiting IGF-mediated functions. However, due to the lack of literature on the binding sites of IGFBP-3, IGFBP-5 or IGF-II for VN, peptide arrays were constructed consisting of VN-peptides and were used to identify the sites at which these proteins interact with VN. The method employs Fmoc (9-fluorenylmethoxycarbonyl) protection chemistry whereby the peptides are delivered automatically to discrete spots on the membranes. The resulting array can be screened directly in the solid phase using an appropriately labeled target protein to identify peptides that bind the target with increased affinity.

The interactions of IGFBP-3, IGFBP-5 and/or IGF-II with the SPOT immobilized VN-peptides were determined by overlaying the peptide array membranes with 10 µg/mL recombinant protein. Interacting peptides hybridized to the cognate peptide motifs immobilized on the membranes. In addition to the unique binding sites within VN, a common VN-motif (motif 8; FIG. 4) was shared by all the three ligands (IGF-II, IGFBP-3 and IGFBP-5). This motif is located in the C-terminal end and was seen to be localized within the Hemopexin-type domain-2 (HX-2) of native VN (FIG. 4). HX domains, consisting of hemopexin-like repeats, are found in several matrix metalloproteinases (MMPs) and in VN. HX domains fulfill functions in the activation and inhibition of MMPs, assist in dimerization of proteins, and facilitate binding of substrates to proteins containing HX domains which is especially true for the HX domains in VN. Proteins such as type-I collagen and heparin have been reported to bind specifically to the HX-2 domain of VN. A theoretical 3D structural model of the complete VN protein generated by Lynn et al. (2005) suggests that the HX-2 domain forms the major lobe of the bi-lobed VN tertiary structure and that the residues within this domain are highly accessible to other proteins. Indeed, this fits well with the observation that several proteins are known to bind to this region, including heparin. Herein, the inventors report for the first time that IGF-II, IGFBP-3 and IGFBP-5 also bind to this 'highly accessible' HX-2 domain of VN between amino acid residues 425-433 (motif 8; FIG. 4). Furthermore, IGF-II was also seen to uniquely bind the HX-2/HBD domain within VN between residues 386-394 (motif 7; FIG. 4).

Given that critical sites for IGFBP and VN interactions were identified, a peptide inhibition strategy was employed to disrupt this association. Two peptides (P7 and P8) were designed to mimic the two IGF-II, IGFBP-3 and IGFBP-5 binding-motifs (motif 7 and 8) of VN. As outlined above, the aim was to allow for the peptides to bind these ligands at sites of VN-binding, thereby preventing their subsequent interaction with VN.

On substitution of the IGF-I:IGFBP-5:VN trimeric complex with VN-peptides P7 and P8, (alone and in combination), a significant reduction in the trimeric complex-stimulated MCF-7 cell migration was observed (FIG. 5). The most significant inhibition was observed at near-equimolar concentrations (3× molar concentration of IGFBP-5; 3×=43 ng/mL for P7 and 38 ng/mL for P8) of peptides tested. At peptide concentrations of 9×, the inhibition in migration was not as profound; nevertheless, these differences were not significant. At the highest peptide concentration (18×) inhibition of cell migration was not observed, which may be due to aggregation of the peptides at such high doses. The present inventors believe that at concentrations as high as 18× (≥770 ng/mL), peptides diluted in serum-free medium of physiological pH (pH 7.2) have the tendency to precipitate or aggregate. This may have rendered the peptides unable to bind the IGFBP-5. The inhibitory effects observed with these peptides were specific to the peptides P7 and P8 (motif-7 and motif-8 mimics); no inhibition of migration was observed when a non-binding negative peptide (Neg) was substituted into the trimeric complex (FIG. 5). The negative peptide design was based on the sequence of VN to which no binding of either IGF-II or IGFBP-3/-5 was detected in the peptide array studies. The inability of this peptide to inhibit cell migration indirectly suggests it lacks the ability to disrupt the trimeric complex and affect the corresponding downstream effects. However, most strikingly, at 3× concentrations, the inhibition of cell migration observed with peptide P7 and P8 were significantly less than that induced by even Anlg at the same molar concentration (3×) (FIG. 5). This suggests that these small and specific peptides, at low doses, are highly efficient at antagonizing the IGF-I:IGFBP-5:VN-mediated breast cancer cell migration responses, above that mediated by the positive control.

From evidence acquired so far, the inventors consider that the mode of action of these peptides is through the disruption of the association of the IGFBP and VN by binding to IGFBP at sites critical for VN-binding. By preventing this association, the unbound IGF-I:IGFBP, removed after the washing step involved in the assay, results in minimal IGF-I being present to stimulate both the receptor activation and the potential cross-talk with VN-binding integrins. The peptides identified herein can specifically disrupt IGFBP and VN interactions and have minimal effects on IGF-I:IGFBP interactions, since indirect evidence exists on separate binding sites being present on IGFBP for VN and IGF-I.

Experimental Methods and Materials

Materials

Human vitronectin (VN) was purchased from Promega. Human receptor grade IGF-I, IGFBP-5, IGFBP-3, IGF-II and anti-IGFBP-5 antibody were purchased from GroPep. Fraction V BSA was purchased from HyClone. IGF-II antibody was from Abcam and anti-IGFBP-3 polyclonal antibody was a kind gift from Dr Robert Baxter (Kolling Institute of Medical Research, Australia). Peptide arrays with VN-peptides spotted onto it were obtained from PepMetric Technologies Inc. (British Columbia, Canada). Individual peptides were obtained from Mimotopes (Clayton, VIC, Australia). Transwells® were purchased from Corning Inc.

Cell Lines and Cell Culture

The breast cell lines MCF-7 and the MCF10A were used in this study. MCF-7 cells are a breast cancer cell line with a luminal epithelial cell type. MCF10A cells non-tumorigenic mammary epithelial cell line. The MCF-7 human breast carcinoma (Cat no. HTB-22) and MCF10A transformed normal mammary epithelial (Cat no. CRL-10317) were obtained from the American Type Culture Collection (ATCC, Manassas, Va.). MCF-7 cells were grown in Dulbecco's Modified Eagle's Medium/Ham's F12 (DMEM/F12) medium (1:1) (Life Technologies) containing 15 mM HEPES, 10% FCS (HyClone, VIC, Australia), 1% Penicillin+Streptomycin (Life Technologies) and 0.01% Gentamycin (Life Technologies). MCF10A cells were maintained in DMEM/F12 (1:1) containing 15 mM HEPES, 5% horse serum (HS) (Life Technologies), 1% Penicillin+Streptomycin, 0.01% Gentamycin, 10 µg/mL bovine insulin, 20 ng/mL EGF, 50 ng/mL cholera enterotoxin and 0.5 µg/mL hydrocortisone. The identity of the breast cell lines was authenticated using short STR profiling. All cultures were passaged regularly every 2-3 days using trypsin-EDTA detachment and stocks of cells were maintained by freezing $2 \times 10^6$ cells in liquid nitrogen suspended in cryopreservation medium (growth medium+40% FCS+10% DMSO).

Pre-Binding of Proteins

The Transwell® inserts were prepared by pre-binding the lower chamber and the under-surface of the 8-µm pore membranes with proteins as described below. For all 2D functional assays described throughout this study, including Transwell® the treatments for the pre-binding steps were VN, IGF-I+IGFBP-5+VN (TRI) complex, either alone or in combination with respective controls or VN-peptides. The concentrations of the proteins added into the culture wells were VN, 1 µg/mL; IGF-I, 30 ng/mL and IGFBP-5, 90 ng/mL, unless otherwise stated. The concentration of VN-peptides used are indicated where appropriate.

Pre-Binding VN, IGF-I, IGFBPs and IGF-II to Transwells®

Optimal IGF-I:IGFBP-5:VN-mediated attachment and migration of MCF-7 cells in multiwell plates is obtained by pre-binding human native-IGF-I and/or IGFBP-5 and VN at concentrations of 30 ng/mL, 90 ng/mL and 1 µg/mL per well, respectively, to the lower chambers and under surfaces of Transwells®. Hence, similar concentrations of these proteins were used for the experiments reported in this study. For Anlg, concentrations varying from 30 ng/mL to 300 ng/mL were used.

Transwells® were prepared by pre-binding the test proteins, either alone or in combinations, to the lower chambers and under-surfaces of Transwells® following procedures previously described (Kricker et al., 2003). Briefly, 0.5 mL DMEM/F12 serum-free phenol-red free medium (SFM) containing 1 µg/mL VN was added to the lower chambers of 24-well, 8-µm pore Transwell® plates and incubated for 3 hours at 37° C. Unbound VN was removed and the wells were washed twice with 0.5 mL SFM+0.5% BSA following which 0.5 mL of SFM+0.5% BSA was placed in the lower chamber to block surfaces with no protein bound. To pre-bind growth factors, 0.5 mL SFM+0.05% BSA containing native IGF-I (30 ng/mL), IGFBP-5 (90 ng/mL) or Anlg, either alone or in combination, were added to the lower chambers of the Transwells® and incubated overnight at 4° C. The solution containing unbound growth factors was removed and the wells were washed twice with SFM+0.05% BSA and replaced with 0.5 mL of SFM+0.05% BSA. Throughout the pre-binding procedure care was taken to keep the upper surface of the Transwell® inserts dry.

Transwell® Migration Assays

Migration assays were essentially performed following protocols described previously in Leavesley et al 1993, J Cell Biol. 121:163-70. The cells in culture flasks were split 1:1, 24 hours prior to performing the migration assay. The cells were serum-starved for 4 hours and a cell suspension containing $6 \times 10^4$ cells in 200 µL SFM+0.05% BSA was seeded onto the upper-surface of the pre-coated Transwell® inserts and incubated for 15 hours at 37° C., 5% $CO_2$ (refer to above for proteins pre-bound and concentrations used). Un-migrated cells from the upper-surface were removed using cotton-swabs. Cells that migrated to the lower-surface of the Transwell® membranes were fixed in 3.7% paraformaldehyde (20 mins) and stained with 0.01% Crystal Violet-PBS solution (20 mins). The Transwell® inserts were washed to remove excess stain and the relative number of cells that migrated to the lower-surface of the membranes were quantified by extracting the stain in 10% acetic acid (10 mins) and determining the optical density of the extracted stain at 595 nm using a 96-well plate spectrophotometer (Benchmark Plus, BioRad). Transwells® suspended without cells in SFM+0.05% BSA were used as blanks.

Peptide Arrays

VN peptide arrays were designed to map the critical binding sites of VN to IGF-II, IGFBP-3 or IGFBP-5. These binding sites were used to design VN-based peptides that could competitively bind IGFBP-3/IGFBP-5 and prevent them from binding to VN thereby preventing the formation of the proliferation- and migration-inducing VN+IGFBP+IGF-I trimeric complexes.

Peptide Array Design

The entire VN protein sequence, excluding the signal peptide (residues 1-19), was divided into overlapping 16-mer peptides with 3 amino acid (AA) frameshift/offset. This yielded 148 overlapping peptides covering the entire VN sequence (residues 20-478) (Table 6) with a resolution of 3 AA. Peptide synthesis and spotting onto a cellulose membrane were outsourced to PepMetric Technologies Inc. (Richmond, BC, Canada). For a diagrammatic illustration of the strategy used to divide an example amino acid sequence into peptides and to spot them onto the membrane, please refer to http://www.pepmetric.com/html/Pep-Overlap.html. The VN-overlapping peptides were generated using FMOC (9-fluorenylmethoxycarbonyl) Solid-Phase SPOT synthesis onto PEG-grafted amine-functionalized cellulose membrane (Whatman® 540 filter paper). The peptides were spotted onto the cellulose membrane in a 10×16 grid with each peptide being 10~50 nM in concentration with >70% purity. Finally, these membranes were acetylated in order to cap the free ends of the spotted peptides preventing them from degradation during shipping and storage.

Along with the VN-peptides these membranes were also spotted with a positive control (i.e., universal binding peptides tested by the manufacturer to be positive for antibodies from goat, mouse, rat and chicken) and a negative control (ie. non-binding peptides as well as BSA) controls. For a schematic of the arrangement of VN-peptides and controls refer to FIG. 2 and for the sequence of each peptide corresponding to the grid number refer to Table 6. Four such replicate membranes were prepared and stored at room temperature in a clip sealed plastic bag. Long-term storage was at −20° C.

Protocol for Ligand Binding and Detection Using Immunoblotting and ECL

Membrane Activation and Blocking

Methanol or ethanol was used to enhance the rehydration of peptide spots that might be hydrophobic. The peptides spotted onto the membranes were activated by incubating in 3 mL of 70% ethanol for five mins. The membranes were subsequently washed three times, 10 minutes each, in 10 mL TBS (Tris Buffered Saline; 8 g NaCl, 0.2 g KCl and 6.1 g Tris Base into 1000 mL of milliQ water, pH 7) with gentle rocking. Membrane blocking was performed by incubating in 10 mL casein-based membrane blocking buffer (MBS; Sigma-Aldrich) overnight at 4° C. The following day, the membranes were washed twice, 10 minutes each, in 10 mL TBS-T (TBS+0.05% Tween-20; pH 7).

Ligand Binding

Ligands used to test binding to VN-peptides were IGFBP-3, IGFBP-5 and IGF-II. For ligand binding, four separate solutions of 1 µg/mL ligand in 10 mL MBS buffer were prepared and each membrane was incubated in one of the four ligand solutions overnight at 4° C., with gentle rocking. Hence VN-peptide membranes for IGFBP-3, IGFBP-5 or IGF-II ligands, were prepared. The following day, the membranes were washed three times, 10 minutes each, in 10 mL TBS-T.

Membrane Immunoblotting

The binding of the ligands to peptides within the membrane was detected using immunoblotting. The membranes were incubated overnight at 4° C. with 10 mL primary antibody solution (in MBS buffer) targeting the respective ligands. The antibodies used were anti-IGFBP-3 (1:10,000), anti-IGFBP-5 (1:10,000) and anti-IGF-II (1:5000) to detect IGFBP-3, IGFBP-5 and IGF-II respectively. The following day, the membranes were washed three times, 10 minutes each, in 10 mL TBS-T and incubated with 10 mL HRP-conjugated secondary IgG antibody diluted 1:15,000 in MBS buffer for 1 hour at room temperature.

Following a further three washes of 10 minutes each, the peptide spots were visualized using ECL. The membranes were exposed onto x-ray films and developed using a film processor (AGFA CP 1000), or were imaged directly using the ChemiDoc™ XRS system (BioRad).

Membrane Regeneration/Stripping

Care was taken to keep the membranes wet at all times after the ECL step. The membranes were washed three times for 10 minutes each in 20 mL milliQ $H_2O$. The membranes were then incubated overnight at 42° C. in 20 mL stripping buffer A (8M Urea, 0.1% SDS and 0.5% 2-mercaptoethanol in PBS; pH 7.0) following which the membranes were washed in 20 mL stripping buffer B (10% acetic acid, 50% ethanol in milliQ $H_2O$) three times, 10 minutes each. Finally, the membranes were washed three times for 10 minutes each in 20 mL 70% ethanol and either blocked with the MBS buffer to be reused immediately or air-dried for storage.

Example 4

MCF-7 Cell Migration and Growth in Response to VN Peptides

The above examples demonstrate that VN peptides inhibit IGF-I:IGFBP:VN trimeric complex-stimulated increased cell migration. This examples provides additional evidence to support the cell migration data and also provides evidence for the ability of VN peptides to reduce trimeric complex-mediated growth of tumor spheroids in a three-dimensional (3D) growth assay.

Figure 6:
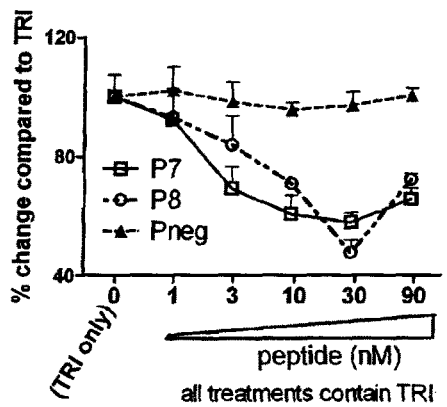
FIG. 6 is a graphical representation showing MCF-7 cell migration in response to VN peptides. MCF-7 cells were seeded onto the upper-surface of a Transwell inserts coated on the under-surface with treatments containing IGF-I+IGFBP-3+VN (TRI; 10 nM) with or without increasing concentrations of either peptide P7, P8 or Pneg. Migration was assessed after 15 hours. Data is represented as percentage of change in migration compared to the TRI only control. Error bars indicate standard error mean.

Migration assays were carried out and a dose dependent inhibition of cell migration was observed when VN peptides P7 and P8 (open square and circle, respectively) were added to the trimeric complex (TRI; 10 nM) (FIG. 6). Most significant inhibition occurred at the 30 nM peptide dose (FIG. 6), wherein cell migration returned to the 'VN only' treatment levels (data not shown). Importantly, no inhibition of cell migration was observed when increasing concentrations of a non-binding negative peptide (Pneg) were added to the trimeric complex (FIG. 6), indicating the specific nature of P7 and P8. This assay has been repeated three times with treatments tested in triplicate wells in each replicate experiment.

Figure 7:
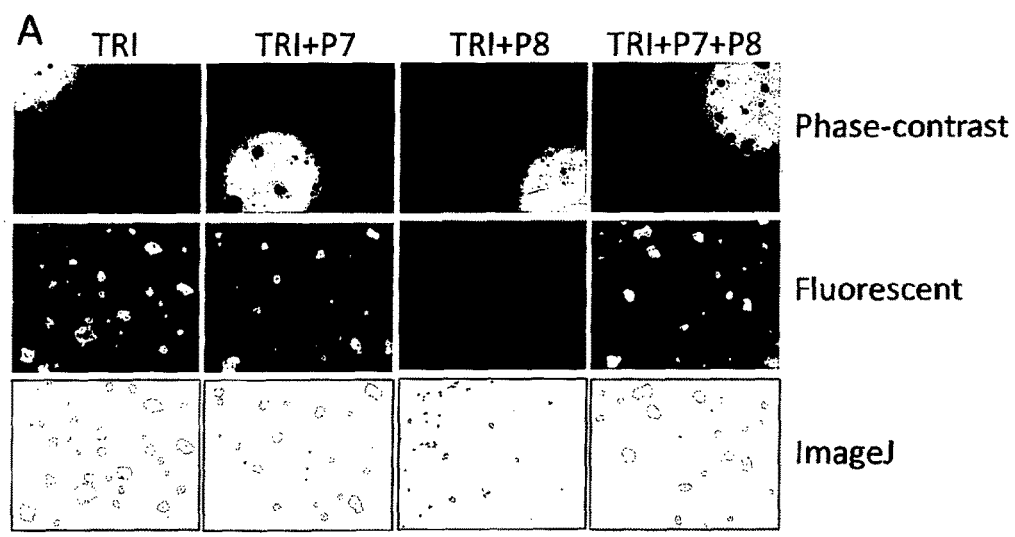
FIG. 7 is a photographic and graphical representation showing MCF-7 3D cell growth in response to peptide antagonists. MCF-7 cells suspended in media containing 1% serum and 2.5% Matrigel (Matrigel media) were layered onto a thin layer of 100% Matrigel. Spheroids were allowed to form in Matrigel media containing VN, TRI or TRI supplemented with peptides P7 and P8. Cells were allowed to grow for 14 days with media+proteins changed every 3 days. (A) Phase contrast and fluorescence microscopy was used to obtain images of the spheroids treated with 90 nM P7, P8 or P7+8. The fluorescent images were subjected to analysis using Image J to calculate spheroid sizes. The images post-ImageJ analyses are depicted in the bottom panel of A. All the images depicted are representative images obtained from triplicate experiments with treatments tested in duplicates in each replicate experiment. Scale bar denotes 100 μm. (B) Scatter plot depicts mean spheroid size ($\mu m^2$) at Day 14 for each treatment, calculated using Image-J (90 nM peptide treatments are depicted here). Each data point in the graph is the average size of all spheroids present in a single field of view at 40× magnification. ** denotes $p<0.01$ and * denotes $p<0.05$. (C) To measure cell viability/proliferation the 3D culture was treated on Day 14 with 5% Alamar Blue dye for 4 hours and fluorescence intensities were recorded. Error bars indicate SEM. ** denotes $p<0.01$ Vs TRI and * denotes $p<0.05$ Vs TRI. The experiment was repeated twice with treatments tested in duplicate wells in each replicate experiment. TRI=IGF-I:IGFBP-5:VN trimeric complex (equimolar at 10 nM concentrations).
Figure 7:
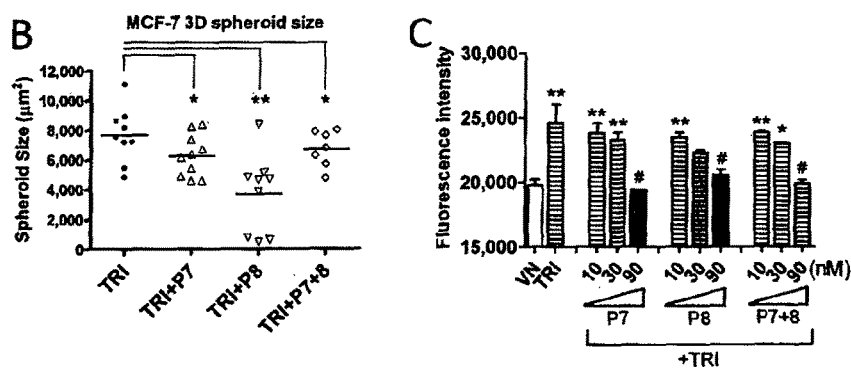

MCF-7 cells were also cultured in Matrigel to form tumor spheroids and were treated with IGF-I:IGFBP-3:VN trimeric complex (TRI) with or without increasing concentrations of VN peptides (P7, P8 or P7+8). Upon observing the morphology of TRI-treated tumor spheroids using phase-contrast microscopy the size of the tumor spheroids was seen to decrease with increasing concentrations of the peptides used. This was observed for both P7 and P8 as well as for P7+8 (FIG. 7A); representative images of peptide treatments at concentrations of 90 nM are depicted in this figure. These 3D Matrigel cultures were then fluorescently stained using the actin-binding dye phalloidin (FIG. 7A, middle panel) and were subsequently subjected to analysis using Image J to calculate spheroid sizes (images post-ImageJ analyses are depicted in the bottom panel of FIG. 7A). Spheroid size calculations using ImageJ revealed that the spheroids in treatments containing the peptides were significantly smaller than those in the control TRI treatments, with peptide P8 demonstrating the highest inhibitory effects (FIG. 7B). Furthermore, when assessed for their viability using the metabolic dye AlamarBlue it was seen that the peptides P7 (*, $p<0.05$) and P8 (**, $p<0.01$) at 90 nM were able to significantly inhibit TRI-stimulated cell viability (FIG. 7C). Importantly, the cell viability in the 3D culture observed for this treatment was similar to that observed for VN only control treatment (FIG. 7C). This indicates that the peptides may be able to block the access of IGF-I to VN/ECM proteins and thereby block IGF-stimulated effects.

In summary, the above data suggest that VN peptides are able to inhibit the growth and viability of breast cancer epithelial cells in an environment (Matrigel) that very closely mimics the in vivo tumor micro-environment.

Methods

Migration Assay:

The breast cancer epithelial cell line MCF-7 was used for this assay. Migration was assessed by measuring relative number of cells migrating through 8-µm pore Transwell membranes in response to substrate-bond proteins complexes. IGFBP-3 was allowed to bind either peptide P7, P8 or a combination of P7 and P8 for 2 hours. IGF-I was later added to this protein mix which was then added to Transwells pre-coated with VN. Post-overnight incubation, unbound proteins were removed, Transwells washed twice and cells seeded onto the upper chamber. Cells migrated to the under-surface over 15 hours were indirectly quantified using crystal violet staining.

3D Growth Assay:

To closely mimic in vivo conditions, cells were grown in a 3D matrix (Matrigel) closely resembling in vivo extracellular matrix physiology. MCF-7 cells suspended in growth media containing 1% serum and 2.5% Matrigel (Matrigel media) were layered onto a thin layer of 100% Matrigel. Tumor spheroids were allowed to form for 3 days after which spent media was replenished with Matrigel media containing VN only, trimeric complex, or trimeric complex supplemented with increasing concentrations of peptides (P7, P8 or P7+P8). Cells were allowed to grow for additional 11 days with media+proteins changed every 3 days. Spheroid morphology was assessed using phase-contrast microscopy and cell viability was measured using AlamarBlue, a fluorescent metabolic dye.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

Annunziata et al., 2011. The IGF system. *Acta Diabetologica.* 48:1-9.

Beattie et al., 2010. Cross-talk between the insulin-like growth factor (IGF) axis and membrane integrins to regulate cell physiology. *J Cell Physiol.* 224:605-11.

Blum et al., 2003. Development of new insulin-like growth factor-1 receptor kinase inhibitors using catechol mimics. *J Biol Chem.* 278:40442-54.

Bonneterre et al., 1990. Prognostic significance of insulin-like growth factor 1 receptors in human breast cancer. *Cancer Res.* 50:6931-5.

Boone, D. N., and A. V. Lee. 2012. Targeting the insulin-like growth factor receptor: developing biomarkers from gene expression profiling. *Crit Rev Oncog.* 17:161-73.

Creighton et al 2008. Insulin-like growth factor-I activates gene transcription programs strongly associated with poor breast cancer prognosis. *J Clin Oncol.* 26:4078-85.

Dupont, J., and D. LeRoith. 2001. Insulin and insulin-like growth factor I receptors: similarities and differences in signal transduction. *Horm Res.* 55 Suppl 2:22-6.

Fox et al., 2011. A kinome-wide screen identifies the insulin/IGF-I receptor pathway as a mechanism of escape from hormone dependence in breast cancer. *Cancer Res.* 71:6773-84.

Garcia-Echeverria et al., 2004. In vivo antitumor activity of NVP-AEW541-A novel, potent, and selective inhibitor of the IGF-IR kinase. *Cancer Cell.* 5:231-9.

Gombos et al., 2012. Clinical development of insulin-like growth factor receptor-1 (IGF-1R) inhibitors: At the crossroad? *Invest New Drugs.*

Haluska et al., 2006. In vitro and in vivo antitumor effects of the dual insulin-like growth factor-I/insulin receptor inhibitor, BMS-554417. *Cancer Res.* 66:362-71.

Haluska et al., Gualberto, A. A. Adjei, and J. S. de Bono. 2007. Phase I dose escalation study of the anti insulin-like growth factor-I receptor monoclonal antibody CP-751, 871 in patients with refractory solid tumors. *Clin Cancer Res.* 13:5834-40.

Hollier et al., 2008. Substrate-bound insulin-like growth factor (IGF)—I-IGF binding protein-vitronectin-stimulated breast cell migration is enhanced by coactivation of the phosphatidylinositide 3-Kinase/AKT pathway by alphav-integrins and the IGF-I receptor. *Endocrinology.* 149:1075-90.

Huang et al., 2009. The mechanisms of differential sensitivity to an insulin-like growth factor-1 receptor inhibitor (BMS-536924) and rationale for combining with EGFR/HER2 inhibitors. *Cancer Res.* 69:161-70.

Kashyap et al., 2011. Insulin-Like Growth Factor-I:Vitronectin Complex-Induced Changes in Gene Expression Effect Breast Cell Survival and Migration. *Endocrinology.* 152:1388-401.

Key et al., 2010. Insulin-like growth factor 1 (IGF1), IGF binding protein 3 (IGFBP3), and breast cancer risk: pooled individual data analysis of 17 prospective studies. *Lancet Oncol.* 11:530-42.

Kricker et al., 2003. Structural and functional evidence for the interaction of insulin-like growth factors (IGFs) and IGF binding proteins with vitronectin. *Endocrinology.* 144:2807-15.

Munshi et al., 2003. Structure of apo, unactivated insulin-like growth factor-1 receptor kinase at 1.5 A resolution. *Acta Crystallogr D Biol Crystallogr.* 59:1725-30.

Nielsen et al., 2004. Expression of the insulin-like growth factor I receptor and urokinase plasminogen activator in breast cancer is associated with poor survival: potential for intervention with 17-allylamino geldanamycin. *Cancer Res.* 64:286-91.

Pandini et al., 2002. Insulin/insulin-like growth factor I hybrid receptors have different biological characteristics depending on the insulin receptor isoform involved. *J Biol Chem.* 277:39684-95.

Sachdev et al., 2003. A chimeric humanized single-chain antibody against the type I insulin-like growth factor (IGF) receptor renders breast cancer cells refractory to the mitogenic effects of IGF-I. *Cancer Res.* 63:627-35.

Sachdev et al., 2004. A dominant negative type I insulin-like growth factor receptor inhibits metastasis of human cancer cells. *J Biol Chem.* 279:5017-24.

Schillaci et al., 2006. Immunization with murine breast cancer cells treated with antisense oligodeoxynucleotides to type I insulin-like growth factor receptor induced an antitumoral effect mediated by a CD8+ response involving Fas/Fas ligand cytotoxic pathway. *J Immunol.* 176:3426-37.

Shimizu et al., Expression of insulin-like growth factor 1 receptor in primary breast cancer: immunohistochemical analysis. *Hum Pathol.* 35:1537-42.

Upton, Z et al., 1999. Identification of vitronectin as a novel insulin-like growth factor-II binding protein. *Endocrinology.* 140:2928-31.

Weroha, S. J., and P. Haluska. 2008. IGF-1 receptor inhibitors in clinical trials—early lessons. *J Mammary Gland Biol Neoplasia.* 13:471-83.

TABLE 8

| NUCLEOTIDE SEQUENCES ENCODING SPECIFIC EMBODIMENTS OF THE VN ANTAGONIST PEPTIDES OF THE INVENTION | | |
|---|---|---|
| VN Peptide Sequence | Nt SED ID NO | Nucleotide sequence of peptide sequence |
| P1 | | |
| CQCDELCSYYQSCCTDYTA (SEQ ID NO: 2, human) | SEQ ID NO: 1 (encoding SEQ ID NO: 2) | TGCCAGTGCGACGAGCTGTGCAGCTACTACCAGAGCTGCTGCACCGACTA CACCGCC |

TABLE 8-continued

NUCLEOTIDE SEQUENCES ENCODING SPECIFIC EMBODIMENTS OF THE VN ANTAGONIST PEPTIDES OF THE INVENTION

| VN

TABLE 8-continued

NUCLEOTIDE SEQUENCES ENCODING SPECIFIC EMBODIMENTS OF THE VN ANTAGONIST PEPTIDES OF THE INVENTION

| VN Peptide Sequence | Nt SED ID NO | Nucleotide sequence of peptide sequence |
|---|---|---|
| KGNHYWEYVFQQQPSQEDC (SEQ ID NO: 48, bovine) | SEQ ID NO: 47 (encoding SEQ ID NO: 48), | AAGGGCAACCACTACTGGGAGTACGTGTTCCAGCAGCAGCCCAGCCAGGA GGACTGC |
| KGNHYWEYVFQQQPSREEC (SEQ ID NO: 50, goat) | SEQ ID NO: 49 (encoding SEQ ID NO: 50), | AAGGGCAACCACTACTGGGAGTACGTGTTCCAGCAGCACCCCAGCCGCGA GGAGTGC |
| KGKQYWEYEFQQQPSQEEC (SEQ ID NO: 52, mouse) | SEQ ID NO: 51 (encoding SEQ ID NO: 52), | AAGGGCAAGCAGTACTGGGAGTACGAGTTCCAGCAGCAGCCCAGCCAGGA GGAGTGC |
| KGDKYWEYQFQQQPSQEEC (SEQ ID NO: 54, rabbit) | SEQ ID NO: 53 (encoding SEQ ID NO: 54) | AAGGGCGACAAGTACTGGGAGTACCAGTTCCAGCAGCAGCCCTCCCAGGA GGAGTGC |
| KGKQYWEYEFQQQPSQEEC (SEQ ID NO: 56, rat) | SEQ ID NO: 55 (encoding SEQ ID NO: 56); | AAGGGCAAGCAGTACTGGGAGTACGAGTTCCAGCAGCAGCCCAGCCAGGA GGAGTGC |

P5

| VN Peptide Sequence | Nt SED ID NO | Nucleotide sequence of peptide sequence |
|---|---|---|
| FEHFAMMQRDSWEDIFELLFWGRTS (SEQ ID NO: 58, human) | SEQ ID NO: 57 (encoding SEQ ID NO: 58), | TTCGAGCACTTCGCCATGATGCAGAGGGACAGCTGGGAGGACATCT TCGAGCTGCTGTTCTGGGGCAGGACCAGC |
| FAHFALMQRDSWEDIFRLLFWSHSF (SEQ ID NO: 60, pig) | SEQ ID NO: 59 (encoding SEQ ID NO: 60), | TTCGCCCACTTCGCCCTGATGCAGCGCGACAGCTGGGAGGACATCT TCCGCCTGCTGTTCTGGAGCCACAGCTTC |
| FKHFALMQRDSWVDIFRLLFWGGSY (SEQ ID NO: 62, bovine) | SEQ ID NO: 61 (encoding SEQ ID NO: 62), | TTCAAGCACTTCGCCCTGATGCAGAGGGACAGCTGGGTGGACATCT TCAGGCTGCTGTTCTGGGGCGGCAGCTAC |
| FKHFALMQRDSWEDIFRLLFWGGSF (SEQ ID NO: 64, goat) | SEQ ID NO: 63 (encoding SEQ ID NO: 64), | TTCAAGCACTTCGCCCTGATGCAGCGCGACAGCTGGGAGGACATC TTCCGCCTGCTGTTCTGGGGCGGCAGCTTC |
| FEHFALLQRDSWENIFELLFWGRSS (SEQ ID NO: 66, mouse) | SEQ ID NO: 65 (encoding SEQ ID NO: 66), | TTCGAGCACTTCGCCCTGCTGCAGAGGGACAGCTGGGAGAACATC TTCGAGCTGCTGTTCTGGGGCAGGAGCAGC |
| FEHFAMLHRDSWEDIFKLLFWGRPS (SEQ ID NO: 68, rabbit) | SEQ ID NO: 67 (encoding SEQ ID NO: 68) | TTCGAGCACTTCGCCATGCTGCACCGCGACTCCTGGGAGGACATC TTCAAGCTGCTGTTCTGGGGCCGCCCCTCC |
| FEHFALLQRDSWENIFELLFWGRSS (SEQ ID NO: 70, rat) | SEQ ID NO: 69 (encoding SEQ ID NO: 70); | TTCGAGCACTTCGCCCTGCTGCAGAGGGACAGCTGGGAGAACATC TTCGAGCTGCTGTTCTGGGGCAGGAGCAGC |

P6

| VN Peptide Sequence | Nt SED ID NO | Nucleotide sequence of peptide sequence |
|---|---|---|
| GRTSAGTRQPQFISRDWHGVPG (SEQ ID NO: 72, human) | SEQ ID NO: 71 (encoding SEQ ID NO: 72) | GGCAGGACCAGCGCCGGCACCAGGCAGCCCCAGTTCATCAGCAGGG |
| SHSFGGAIEPRVISQDWLGLPE (SEQ ID NO: 74, pig) | SEQ ID NO: 73 (encoding SEQ ID NO: 74) | AGCCACAGCTTCGGCGGCGCCATCGAGCCCCGCGTGATCAGCCAGGACT GGCTGGGCCTGCCCGAG |
| GGSYGGAGQPQLISRNWFGLPG (SEQ ID NO: 76, bovine) | SEQ ID NO: 75 (encoding SEQ ID NO: 76) | GGCGGCAGCTACGGCGGCGCCGGCCAGCCCCAGCTGATCAGCAGGAA CTGGTTCGGCCTGCCCGGC |
| GGSFGGAGQPQLISRDWFGLPG (SEQ ID NO: 78, goat) | SEQ ID NO: 77 (encoding SEQ ID NO: 78) | GGCGGCAGCTTCGGCGGCGCCGGCCAGCCCCAGCTGATCAGCCGCGA CTGGTTCGGCCTGCCCGGC |
| GRSSDGAREPQFISRNWHGVPG (SEQ ID NO: 80, mouse) | SEQ ID NO: 79 (encoding SEQ ID NO: 80) | GGCAGGAGCAGCGACGGCGCCAGGGAGCCCCAGTTCATCAGCAGGAA CTGGCACGGCGTGCCCGGC |
| GRPSGGARQPQFISRDWHGVPG (SEQ ID NO: 82, rabbit) | SEQ ID NO: 81 (encoding SEQ ID NO: 82) | GGCCGCCCCTCCGGCGGCGCCCGCCAGCCCCAGTTCATCTCCCGCGA CTGGCACGGCGTGCCCGGC |
| GRSSDGAKGPQFISRDWHGVPG (SEQ ID NO: 84, rat) | SEQ ID NO: 83 (encoding SEQ ID NO: 84) | GGCAGGAGCAGCGACGGCGCCAAGGGCCCCCAGTTCATCAGCAGGGA CTGGCACGGCGTGCCCGGC |

P7

| VN Peptide Sequence | Nt SED ID NO | Nucleotide sequence of peptide sequence |
|---|---|---|
| LFSSEESNLGANNYDDYRMDWL (SEQ ID NO: 86, human) | SEQ ID NO: 85 (encoding SEQ ID NO: 86) | CTGTTCAGCAGCGAGGAGAGCAACCTGGGCGCCAACAACTACGACGAC TACAGGATGGACTGGCTG |
| WFSSEETGPGGYNYDDYKMDWL (SEQ ID NO: 88, pig) | SEQ ID NO: 87 (encoding SEQ ID NO: 88) | TGGTTCAGCAGCGAGGAGACCGGCCCCGGCGGCTACAACTACGACGAC TACAAGATGGACTGGCTG |
| WLSSEELGLGANNYDSFEMDWL (SEQ ID NO: 90 bovine) | SEQ ID NO: 89 (encoding SEQ ID NO: 90) | TGGCTGAGCAGCGAGGAGCTGGGCCTGGGCGCCAACAACTACGACAGC TTCGAGATGGACTGGCTG |

TABLE 8-continued

NUCLEOTIDE SEQUENCES ENCODING SPECIFIC EMBODIMENTS OF THE VN ANTAGONIST PEPTIDES OF THE INVENTION

| VN Peptide Sequence | Nt SED ID NO | Nucleotide sequence of peptide sequence |
|---|---|---|
| WFSSEELGLGADNYDNYEMDWL (SEQ ID NO: 92, goat) | SEQ ID NO: 91 (encoding SEQ ID NO: 92) | TGGTTCAGCAGCGAGGAGCTGGGCCTGGGCGCCGACAACTACGACAAC TACGAGATGGACTGGCTG |
| LFSSEESGLGTYNNYDYDMDWL (SEQ ID NO: 94, mouse) | SEQ ID NO: 93 (encoding SEQ ID NO: 94) | CTGTTCAGCAGCGAGGAGAGCGGCCTGGGCACCTACAACAACTACGACT ACGACATGGACTGGCTG |
| WFSSEEVSLGPYNYEDYETSWL (SEQ ID NO: 96, rabbit) | SEQ ID NO: 95 (encoding SEQ ID NO: 96) | TGGTTCTCCTCCGAGGAGGTGTCCCTGGGCCCCTACAACTACGAGGACT ACGAGACCTCCTGGCTG |
| LLSSEESGLGTYNYDYDMNWL (SEQ ID NO: 98, rat) | SEQ ID NO: 97 (encoding SEQ ID NO: 98) | CTGCTGAGCAGCGAGGAGAGCGGCCTGGGCACCTACAACTACGACTACGA CATGAACTGGCTG |
| P8 | | |
| RVNLRTRRVDTVDPPYPRS (SEQ ID NO: 100, human) | SEQ ID NO: 99 (encoding SEQ ID NO: 100) | AGGGTGAACCTGAGGACCAGGAGGGTGGACACCGTGGACCCCCCCTACCC CAGGAGC |
| RVNLRTQRVDTVTPPYPRS (SEQ ID NO: 102, pig) | SEQ ID NO: 101 (encoding SEQ ID NO: 102) | CGCGTGAACCTGCGCACCCAGCGCGTGGACACCGTGACCCCCCCCTACCC CCGCAGC |
| RVNLRTRRVDAVIPPYPRS (SEQ ID NO: 104, bovine) | SEQ ID NO: 103 (encoding SEQ ID NO: 104) | AGGGTGAACCTGAGGACCAGGAGGGTGGACGCCGTGATCCCCCCCTACC CCAGGAGC |
| RVNLRTRRVDSVIPPYPRS (SEQ ID NO: 106, goat) | SEQ ID NO: 105 (encoding SEQ ID NO: 106) | CGCGTGAACCTGCGCACCCGCCGCGTGGACAGCGTGATCCCCCCCTACCC CCGCAGC |
| RVNLRTRRVDSVNPPYPRS (SEQ ID NO: 108, mouse) | SEQ ID NO: 107 (encoding SEQ ID NO: 108) | AGGGTGAACCTGAGGACCAGGAGGGTGGACAGCGTGAACCCCCCCTACCC CAGGAGC |
| RVNLRTQRVDTVNPPYPRS (SEQ ID NO: 110, rabbit) | SEQ ID NO: 109 (encoding SEQ ID NO: 110) | CGCGTGAACCTGCGCACCCAGCGCGTGGACACCGTGAACCCCCCCTACCC CCGCTCC |
| RVNLRTRRVDSVNPPYPRS (SEQ ID NO: 112, rat) | SEQ ID NO: 111 (encoding SEQ ID NO: 112) | AGGGTGAACCTGAGGACCAGGAGGGTGGACAGCGTGAACCCCCCCTACCC CAGGAGCACTGGCACGGCGTGCCCGGC |

What is claimed is:

1. A method for (1) binding to at least one vitronectin-binding partner selected from an insulin-like growth factor (IGF) and an IGF-binding protein (IGFBP); (2) inhibiting binding of a vitronectin to at least one vitronectin-binding partner selected from an IGF and an IGFBP; (3) inhibiting formation of a complex comprising a vitronectin and at least one vitronectin-binding partner selected from an IGF and an IGFBP, wherein the complex is selected from (i) a complex comprising, consisting or consisting essentially of vitronectin, IGF-I and an IGFBP, and (ii) a complex comprising, consisting or consisting essentially of vitronectin and IGF-II; (4) inhibiting proliferation of a hyperproliferative cell; (5) inhibiting migration of a hyperproliferative cell; (6) inhibiting invasion of a hyperproliferative cell; and (7) inhibiting survival or viability of a hyperproliferative cell, wherein the hyperproliferative cell defined in (4), (5), (6) and (7) overexpresses IGF-1R and expresses a vitronectin-binding integrin, the method comprising contacting the IGF or IGFBP defined in (1), (2) or (3), or an IGF or IGFBP in the extracellular environment of the hyperproliferative cell defined in (4), (5), (6) or (7), with a proteinaceous molecule which consists or consists essentially of an amino acid sequence represented by formula VIII:

$$\text{RVNLRTX}_1\text{RVDX}_2\text{VX}_3\text{PPYPRS (SEQ ID NO:120)} \quad \text{(VIII)}$$

wherein:
$X_1$ is a basic amino acid residue or a neutral/polar amino acid residue;
$X_2$ is selected from the group consisting of S, T, A, P and G; and
$X_3$ is any amino acid residue;
and wherein the proteinaceous molecule consists of 119 amino acids or less.

2. A method for (1) binding to at least one vitronectin-binding partner selected from an insulin-like growth factor (IGF) and an IGF-binding protein (IGFBP); (2) inhibiting binding of a vitronectin to at least one vitronectin-binding partner selected from an IGF and an IGFBP; (3) inhibiting formation of a complex comprising a vitronectin and at least one vitronectin-binding partner selected from an IGF and an IGFBP, wherein the complex is selected from (i) a complex comprising, consisting or consisting essentially of vitronectin, IGF-I and an IGFBP, and (ii) a complex comprising, consisting or consisting essentially of vitronectin and IGF-II; (4) inhibiting proliferation of a hyperproliferative cell; (5) inhibiting migration of a hyperproliferative cell; (6) inhibiting invasion of a hyperproliferative cell; and (7) inhibiting survival or viability of a hyperproliferative cell, wherein the hyperproliferative cell defined in (4), (5), (6) and (7) overexpresses IGF-1R and expresses a vitronectin-binding integrin, the method comprising contacting the IGF or IGFBP defined in (1), (2) or (3), or an IGF or IGFBP in the extracellular environment of the hyperproliferative cell defined in (4), (5), (6) or (7), with a proteinaceous molecule, wherein the proteinaceous molecule is represented by formula XVI:

$$Z_1\text{RVNLRTX}_1\text{RVDX}_2\text{VX}_3\text{PPYPRSZ}_2 \text{ (SEQ ID NO: 128)} \quad \text{(XVI)}$$

wherein:
$X_1$-$X_3$ are as defined in claim 1 for formula VIII;
$Z_1$ is absent or is selected from at least one of a proteinaceous moiety comprising from about 1 to about 50 amino acid residues and all integer values of amino acid residues therebetween, and a protecting moiety; and
$Z_2$ is absent or is a proteinaceous moiety comprising from about 1 to about 50 amino acid residues and all integer values of amino acid residues therebetween
and wherein the proteinaceous molecule consists of 119 amino acids or less.

3. The method according to claim 1, wherein the proteinaceous molecule consists or consists essentially of an amino acid sequence selected from the group consisting of:
(a) an amino acid sequence selected from: RVNLRTRRVDTVDPPYPRS (SEQ ID NO:100, from human vitronectin); RVNLRTQRVDTVTPPYPRS (SEQ ID NO:102, from pig vitronectin); RVNLRTRRVDAVIPPYPRS (SEQ ID NO:104, from bovine vitronectin); RVNLRTRRVDSVIPPYPRS (SEQ ID NO:106, from goat vitronectin); RVNLRTRRVDSVNPPYPRS (SEQ ID NO:108, C from mouse vitronectin); RVNLRTQRVDTVNPPYPRS (SEQ ID NO:110, from rabbit vitronectin); and RVNLRTRRVDSVNPPYPRS (SEQ ID NO:112, from rat vitronectin);
(b) an amino acid sequence that shares at least 95% sequence identity with the sequence set forth in any one of SEQ ID NO: 100, 102, 104, 106, 108, 110 or 112; or
(c) an amino acid sequence which is encoded by the nucleotide sequence set forth in any one of SEQ ID NO:99 (nucleotide sequence encoding SEQ ID NO:100), SEQ ID NO:101 (nucleotide sequence encoding SEQ ID NO:102), SEQ ID NO:103 (nucleotide sequence encoding SEQ ID NO:104), SEQ ID NO:105 (nucleotide sequence encoding SEQ ID NO:106), SEQ ID NO:107 (nucleotide sequence encoding SEQ ID NO:108), SEQ ID NO:109 (nucleotide sequence encoding SEQ ID NO:110) or SEQ ID NO:111 (nucleotide sequence encoding SEQ ID NO:112);
(d) an amino acid sequence which is encoded by a nucleotide sequence that shares at least 95% sequence identity with the sequence set forth in any one of SEQ ID NO: 99, 101, 103, 105, 107, 109 or 111, or a complement thereof; or (e) an amino acid sequence which is encoded by a nucleotide sequence that hybridizes under at least medium stringency conditions to the sequence set forth in any one of SEQ ID NO: 99, 101, 103, 105, 107, 109 or 111, or a complement thereof, wherein the amino acid sequence of (a), (b), (c), (d) or (e) has any one or more activities selected from the group consisting of: (1) binding to at least one vitronectin-binding partner selected from an IGF and an IGFBP; (2) inhibiting binding of a vitronectin to at least one vitronectin-binding partner selected from an IGF and an IGFBP; (3) inhibiting formation of a complex comprising a vitronectin and at least one vitronectin-binding partner selected from an IGF and an IGFBP, wherein the complex is selected from (i) a complex comprising, consisting or consisting essentially of vitronectin, IGF-I and an IGFBP, and (ii) a complex comprising, consisting or consisting essentially of vitronectin and IGF-II; (4) inhibiting proliferation of a hyperproliferative cell; (5) inhibiting migration of a hyperproliferative cell; (6) inhibiting invasion of a hyperproliferative cell; and (7) inhibiting survival or viability of a hyperproliferative cell.

4. The method according to claim 1, wherein the proteinaceous molecule comprises any one or more of the following: (1) at the N-terminal amino acid residue a protecting group; (2) an N-terminal region that is cleaved in vivo and a glutamyl group thus formed is pyroglutaminated; (3) substituents on the side chains of amino acids in the molecule, which are protected with protecting groups; (4) a carboxyl group at the C-terminal amino acid residue, which is protected by a protecting group; (5) a C-terminus that comprises a descarboxylated amino acid analogue; (6) at least one side chain that have been modified to include a carbohydrate, polyethylene glycol (PEG) or other polymer; or (7) a cyclic peptide having an intramolecular bond between two non-adjacent amino acids.

5. The method according to claim 1, further comprising contacting the IGF or IGFBP defined in (1), (2) or (3), or an IGF or IGFBP in the extracellular environment of the hyperproliferative cell defined in (4), (5), (6) or (7), with at least one other proteinaceous molecule, which consists or consists essentially of an amino acid sequence represented by any one of formulae VII and I-VI:

$$X_1X_2SSEEX_3X_4X_5GX_6X_7NX_8X_9X_{10}X_{11}X_{12}X_{13}X_{14}WL \text{ (SEQ ID NO:119)} \quad \text{(VII)}$$

wherein:
$X_1$ is a hydrophobic amino acid residue;
$X_2$ is a hydrophobic amino acid residue;
$X_3$ is selected from the group consisting of S, T, A, P and G or a hydrophobic amino acid residue;
$X_4$ is selected from the group consisting of S, T, A, P and G or is a neutral/polar amino acid residue;
$X_5$ is selected from the group consisting of S, T, A, P and G or is;
$X_6$ is selected from the group consisting of S, T, A, P and G;
$X_7$ is any amino acid residue;
$X_8$ is absent or is a neutral/polar amino acid residue or hydrophobic amino acid residue;
$X_9$ is an acidic amino acid residue or a hydrophobic amino acid residue;
$X_{10}$ is any amino acid residue;
$X_{11}$ is a hydrophobic amino acid residue;
$X_{12}$ is a charged amino acid residue or an acidic amino acid residue;
$X_{13}$ is a hydrophobic amino acid residue or is selected from the group consisting of S, T, A, P and G; and
$X_{14}$ is any amino acid residue, $$CQCDELCX_1YYQSCCX_2DX_3X_4X_5 \text{ (SEQ ID NO:113)} \quad \text{(I)}$$

wherein:
$X_1$ is selected from the group consisting of S, T, A, P and G;
$X_2$ is selected from the group consisting of S, T, A, P and G or is a hydrophobic amino acid residue;
$X_3$ is a hydrophobic amino acid residue;
$X_4$ is selected from the group consisting of S, T, A, P and G or is a hydrophobic amino acid residue; and
$X_5$ is selected from the group consisting of S, T, A, P and G or is an acidic amino acid residue, $$TX_1X_2X_3GX_4X_5X_6 \text{ (SEQ ID NO:114)} \quad \text{(II)}$$

wherein:
$X_1$ is any amino acid residue;
$X_2$ is a charged amino acid residue;
$X_3$ is any amino acid residue;
$X_4$ is any amino acid residue;
$X_5$ is selected from the group consisting of S, T, A, P and G; and
$X_6$ is any amino acid residue, $$VDAAX_1ALPAHX_2X_3X_4GRERVY \text{ (SEQ ID NO:115)} \quad \text{(III)}$$

wherein:
$X_1$ is a hydrophobic amino acid residue;
$X_2$ is any amino acid residue;
$X_3$ is a hydrophobic amino acid residue; and
$X_4$ is selected from the group consisting of S, T, A, P and G, $$KGX_1X_2YWEYX_3FQX_4QPSX_5EX_6C \text{ (SEQ ID NO:116)} \quad \text{(IV)}$$

wherein:
$X_1$ is a charged amino acid residue or a neutral/polar amino acid residue;
$X_2$ is a neutral/polar amino acid residue or basic amino acid residue;
$X_3$ is any amino acid residue;
$X_4$ is a basic amino acid residue or a neutral/polar amino acid residue;
$X_5$ is a neutral/polar amino acid residue or a basic amino acid residue; and
$X_6$ is an acidic amino acid residue, $$FX_1HFAX_2X_3X_4RDSWX_5X_6IFX_7LLFWX_8X_9X_{10}X_{11} \text{ (SEQ ID NO:117)} \quad \text{(V)}$$

wherein:
$X_1$ is a charged amino acid residue, a basic amino acid residue, or is selected from the group consisting of S, T, A, P and G;
$X_2$ is a hydrophobic amino acid residue;
$X_3$ is a hydrophobic amino acid residue;
$X_4$ is a neutral/polar amino acid residue or a basic amino acid residue;
$X_5$ is an acidic amino acid residues or a hydrophobic amino acid residue;
$X_6$ is an acidic amino acid residue or a neutral/polar amino acid residue;

X₇ is a charged amino acid residue or an acidic amino acid residue;
X₈ is selected from the group consisting of S, T, A, P and G;
X₉ is a basic amino acid residue or is selected from the group consisting of S, T, A, P and G;
X₁₀ is selected from the group consisting of S, T, A, P and G; and
X₁₁ is selected from the group consisting of S, T, A, P and G or is a hydrophobic amino acid residue, $$X_1X_2X_3X_4X_5GX_6X_7X_8PX_9X_{10}ISX_{11}X_{12}WX_{13}GX_{14}PX_{15} \quad \text{(SEQ ID NO:118)} \quad \text{(VI)}$$

wherein:
X₁ is selected from the group consisting of S, T, A, P and G;
X₂ is a basic amino acid residue or is selected from the group consisting of S, T, A, P and G;
X₃ is selected from the group consisting of S, T, A, P and G;
X₄ is selected from the group consisting of S, T, A, P and G or is a hydrophobic amino acid residue;
X₅ is selected from the group consisting of S, T, A, P and G or is an acidic amino acid residue;
X₆ is selected from the group consisting of S, T, A, P and G;
X₇ is any amino acid residue;
X₈ is any amino acid residue;
X₉ is a neutral/polar amino acid residue or a basic amino acid residue;
X₁₀ is a hydrophobic amino acid residue;
X₁₁ is a basic amino acid residue or a neutral/polar amino acid residue;
X₁₂ is an acidic amino acid residue or a neutral/polar amino acid residue;
X₁₃ is a basic amino acid residue or a hydrophobic amino acid residue;
X₁₄ is a hydrophobic amino acid residue; and
X₁₅ is selected from the group consisting of S, T, A, P and G or is an acidic amino acid residue.

6. The method of claim 1, wherein X₁ is an amino acid residue selected from the group consisting of R and Q.

7. The method of claim 1, wherein X₂ is an amino acid residue selected from the group consisting of S, A and T.

8. The method of claim 1, wherein X₃ is an amino acid residue selected from the group consisting of D, T, N, and I.

9. The method according to claim 5, wherein for formula VII:
X₁ is an amino acid selected from the group consisting of L and W;
X₂ is an amino acid selected from the group consisting of L and F;
X₃ is an amino acid selected from the group consisting of S, T, L, and V;
X₄ is an amino acid selected from the group consisting of G, S, and N;
X₅ is an amino acid selected from the group consisting of P and L;
X₆ is an amino acid selected from the group consisting of P, A, G and T;
X₇ is an amino acid selected from the group consisting of N, D, and Y;
X₈ is absent, or is an amino acid selected from the group consisting of N and Y;
X₉ is an amino acid selected from the group consisting of E, D, and Y;
X₁₀ is an amino acid selected from the group consisting of D, N, and S;
X₁₁ is an amino acid selected from the group consisting of Y and F;
X₁₂ is an amino acid selected from the group consisting of K, R, E and D;
X₁₃ is an amino acid selected from the group consisting of M and T; and/or
X₁₄ is an amino acid selected from the group consisting of D, S, and N,
and wherein for formula I:
X₁ is an amino acid selected from the group consisting of S and T;
X₂ is an amino acid selected from the group consisting of T, A, and V;
X₃ is an amino acid selected from the group consisting of Y and F;
X₄ is an amino acid selected from the group consisting of T, A, M, and V; and/or
X₅ is an amino acid selected from the group consisting of A and E,
and wherein for formula II:
X₁ is an amino acid selected from the group consisting of D, S, T, and L;
X₂ is an amino acid selected from the group consisting of H, D, and E;
X₃ is an amino acid selected from the group consisting of P, L, Q, and E;
X₄ is an amino acid selected from the group consisting of R, V, and T;
X₅ is an amino acid selected from the group consisting of P and S; and/or
X₆ is an amino acid selected from the group consisting of Q, E, and A,
and wherein for formula III:
X₁ is an amino acid selected from the group consisting of L and F;
X₂ is an amino acid selected from the group consisting of S, N, and R;
X₃ is an amino acid selected from the group consisting of Y and F; and/or
X₄ is an amino acid selected from the group consisting of S and N,
and wherein for formula IV:
X₁ is an amino acid selected from the group consisting of K, D, and N;
X₂ is an amino acid selected from the group consisting of Q, H, and K;
X₃ is an amino acid selected from the group consisting of Q, V, and E;
X₄ is an amino acid selected from the group consisting of H and Q;
X₅ is an amino acid selected from the group consisting of Q and R; and/or
X₆ is an amino acid selected from the group consisting of E and D,
and wherein for formula V:
X₁ is an amino acid selected from the group consisting of E, K, and A;
X₂ is an amino acid selected from the group consisting of M and L;
X₃ is an amino acid selected from the group consisting of M and L;
X₄ is an amino acid selected from the group consisting of Q and H;
X₅ is an amino acid selected from the group consisting of E and V;

$X_6$ is an amino acid selected from the group consisting of D and N;
$X_7$ is an amino acid selected from the group consisting of R, K, and E;
$X_8$ is an amino acid selected from the group consisting of G and S;
$X_9$ is an amino acid selected from the group consisting of R, H, and G;
$X_{10}$ is an amino acid selected from the group consisting of T, S, and P, and/or
$X_{11}$ is an amino acid selected from the group consisting of S, F, and Y,
and wherein for formula VI:
$X_1$ is an amino acid selected from the group consisting of G and S;
$X_2$ is an amino acid selected from the group consisting of R, H, and G;
$X_3$ is an amino acid selected from the group consisting of T, S, and P;
$X_4$ is an amino acid selected from the group consisting of S, F, and Y;
$X_5$ is an amino acid selected from the group consisting of A, G, and D;
$X_6$ is an amino acid selected from the group consisting of T and A;
$X_7$ is an amino acid selected from the group consisting of R, K, I, and G;
$X_8$ is an amino acid selected from the group consisting of Q, E, and G;
$X_9$ is an amino acid selected from the group consisting of Q and R;
$X_{10}$ is an amino acid selected from the group consisting of F, V, and L;
$X_{11}$ is an amino acid selected from the group consisting of R and Q;
$X_{12}$ is an amino acid selected from the group consisting of D and N;
$X_{13}$ is an amino acid selected from the group consisting of H, L and F;
$X_{14}$ is an amino acid selected from the group consisting of V and L; and/or
$X_{15}$ is an amino acid selected from the group consisting of G and E.

* * * * *